(12) United States Patent
Olsen et al.

(10) Patent No.: US 10,518,054 B2
(45) Date of Patent: Dec. 31, 2019

(54) RESPIRATORY MASK AND RELATED PORTIONS, COMPONENTS OR SUB-ASSEMBLIES

(71) Applicant: Fisher & Paykel Healthcare Limited, Auckland (NZ)

(72) Inventors: Gregory James Olsen, Auckland (NZ); Melissa Catherine Bornholdt, Auckland (NZ); Campbell Neil Addison Martin, Auckland (NZ); Tony William Spear, Auckland (NZ); Simon Mittermeier, Auckland (NZ); Hamish Joshua Rose, Auckland (NZ); Max Leon Betteridge, Auckland (NZ); Christopher Earl Nightingale, Auckland (NZ); Matthew James Pedersen, Auckland (NZ); Sophia Adele Johnson, Auckland (NZ); Mark John Arrowsmith, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 208 days.

(21) Appl. No.: 15/506,226

(22) PCT Filed: Aug. 25, 2015

(86) PCT No.: PCT/NZ2015/050119
§ 371 (c)(1),
(2) Date: Feb. 23, 2017

(87) PCT Pub. No.: WO2016/032343
PCT Pub. Date: Mar. 3, 2016

(65) Prior Publication Data
US 2018/0185598 A1 Jul. 5, 2018

Related U.S. Application Data

(60) Provisional application No. 62/096,481, filed on Dec. 23, 2014, provisional application No. 62/041,236, (Continued)

(51) Int. Cl.
*A61M 16/06* (2006.01)
*A62B 18/08* (2006.01)
*A61M 16/08* (2006.01)

(52) U.S. Cl.
CPC .... *A61M 16/0622* (2014.02); *A61M 16/0611* (2014.02); *A61M 16/0616* (2014.02);
(Continued)

(58) Field of Classification Search
CPC .......... A61M 16/0622; A61M 16/0616; A61M 16/0683
See application file for complete search history.

(56) References Cited

U.S. PATENT DOCUMENTS 301,111 A 7/1884 Genese
443,191 A 12/1890 Iling
(Continued)

FOREIGN PATENT DOCUMENTS

AU 744593 2/2002
AU 2003246441 12/2003
(Continued)

OTHER PUBLICATIONS

Extended European Search Report, Application No. PCT/NZ2015/050119, dated Mar. 5, 2018, 7 pages.
(Continued)

*Primary Examiner* — Bradley J Osinski
(74) *Attorney, Agent, or Firm* — Knobbe, Martens, Olson & Bear, LLP

(57) ABSTRACT

A respiratory mask for providing positive pressure therapy and a bias-flow venting system configured to reduce discernable draft generated by exhausted air are disclosed herein. The respiratory mask has a ball jointed elbow, one or more detachable forehead pieces and a headgear with a spacer fabric region. The elbow is configured to be removable when oriented to a predetermined position. The forehead pieces are provided in one or more sizes. The spacer fabric region having two or more layers wherein the raw edges are turned to the inside of the layers. The seal having improved seal performance and accommodating a wider variety of facial geometries. The bias-flow system having a tube and exhaust holes radially aligned on a bead of the tube. The bias-flow system also having an annular component exhaust holes and a shroud having a plenum chamber around the exhaust holes.

29 Claims, 41 Drawing Sheets

Related U.S. Application Data filed on Aug. 25, 2014, provisional application No. 62/041,262, filed on Aug. 25, 2014, provisional application No. 62/041,234, filed on Aug. 25, 2014.

(52) U.S. Cl.
CPC .... *A61M 16/0633* (2014.02); *A61M 16/0683* (2013.01); *A61M 16/0694* (2014.02); *A61M 16/0825* (2014.02); *A61M 16/0875* (2013.01); *A62B 18/08* (2013.01)

(56) References Cited

U.S. PATENT DOCUMENTS

| | | |
|---|---|---|
| 472,238 A | 4/1892 | Van Orden |
| 577,926 A | 3/1897 | Miller |
| 687,973 A | 12/1901 | Bohn |
| 718,470 A | 1/1903 | Jones |
| 751,091 A | 2/1904 | Linn |
| 770,013 A | 2/1904 | Moran |
| 804,272 A | 11/1905 | Schwarz |
| 1,229,050 A | 5/1917 | Donald |
| 1,445,010 A | 2/1923 | William |
| 1,635,545 A | 7/1927 | Drager |
| 1,710,160 A | 4/1929 | Gibbs |
| 2,126,755 A | 8/1938 | Dreyfus |
| 2,228,218 A | 1/1941 | Schwartz |
| 2,296,150 A | 9/1942 | Dockson et al. |
| 2,353,643 A | 7/1944 | Bulbulian |
| 2,359,506 A | 10/1944 | Battley et al. |
| 2,376,871 A | 5/1945 | Fink |
| 2,388,604 A | 11/1945 | Eisenbud |
| 2,403,046 A | 7/1946 | Bulbulian |
| 2,414,405 A | 1/1947 | Beckwith et al. |
| 2,415,846 A | 2/1947 | Francis |
| 2,444,417 A | 7/1948 | Bierman |
| 2,508,050 A | 5/1950 | Valente |
| 2,540,567 A | 2/1951 | Ray |
| 2,693,800 A | 11/1954 | Caldwell |
| 2,706,983 A | 4/1955 | Matheson et al. |
| 2,738,788 A | 3/1956 | Matheson et al. |
| 2,843,121 A | 7/1958 | Hudson |
| 2,858,828 A | 11/1958 | Matheson |
| 2,859,748 A | 11/1958 | Hudson |
| 2,874,693 A | 2/1959 | Matheson |
| 2,875,759 A | 3/1959 | Galleher |
| 2,881,444 A | 4/1959 | Fresh et al. |
| 2,893,387 A | 4/1959 | Gongoll et al. |
| 2,931,356 A | 4/1960 | Schwartz |
| 2,939,458 A | 6/1960 | Lundquist |
| 2,999,498 A | 9/1961 | Matheson |
| 3,027,617 A | 4/1962 | Gray |
| 3,037,501 A | 6/1962 | Miller |
| 3,040,741 A | 6/1962 | Carolan |
| 3,092,105 A | 6/1963 | Gabb |
| 3,117,574 A | 1/1964 | Replogle |
| 3,234,939 A | 2/1966 | Morton |
| 3,234,940 A | 2/1966 | Morton |
| 3,292,618 A | 12/1966 | Davis et al. |
| 3,295,529 A | 1/1967 | Corrigall et al. |
| 3,315,674 A | 4/1967 | Bloom et al. |
| 3,330,273 A | 7/1967 | Bennett |
| 3,330,274 A | 7/1967 | Bennett |
| 3,424,633 A | 1/1969 | Corrigall et al. |
| 3,490,452 A | 1/1970 | Greenfield |
| 3,530,031 A | 9/1970 | Leow |
| 3,545,436 A | 12/1970 | Holloway |
| 3,599,635 A | 8/1971 | Kenneth |
| 3,752,157 A | 8/1973 | Malmin |
| 3,850,171 A | 11/1974 | Ball et al. |
| 3,890,966 A | 6/1975 | Aspelin et al. |
| 3,936,914 A | 2/1976 | Mancini |
| 3,969,991 A | 7/1976 | Comstock et al. |
| 3,972,321 A | 8/1976 | Proctor |
| 3,977,432 A | 8/1976 | Vidal |
| 3,982,532 A | 9/1976 | Halldin et al. |
| 3,992,720 A | 11/1976 | Nicolinas |
| 4,069,516 A | 1/1978 | Watkins, Jr. |
| 4,090,510 A | 5/1978 | Segersten |
| D250,047 S | 10/1978 | Lewis et al. |
| D250,131 S | 10/1978 | Lewis et al. |
| 4,141,118 A | 2/1979 | Gudell |
| 4,150,464 A | 4/1979 | Tracy |
| D252,322 S | 7/1979 | Johnson |
| 4,167,185 A | 9/1979 | Lewis |
| 4,201,205 A | 5/1980 | Bartholomew |
| 4,258,710 A | 3/1981 | Reber |
| 4,263,908 A | 4/1981 | Mizerak |
| 4,266,540 A | 5/1981 | Panzik et al. |
| 4,278,082 A | 7/1981 | Blackmer |
| 4,354,488 A | 10/1982 | Bartos |
| 4,367,735 A | 1/1983 | Dali |
| 4,378,011 A | 3/1983 | Warncke et al. |
| 4,384,577 A | 5/1983 | Huber et al. |
| 4,437,462 A | 3/1984 | Piljay |
| 4,454,880 A | 6/1984 | Muto et al. |
| 4,470,413 A | 9/1984 | Warncke |
| 4,603,602 A | 8/1986 | Montesi |
| 4,621,632 A | 11/1986 | Bartels et al. |
| 4,641,379 A | 2/1987 | Martin |
| 4,675,919 A | 6/1987 | Heine et al. |
| 4,676,241 A | 6/1987 | Webb et al. |
| 4,706,683 A | 11/1987 | Chilton et al. |
| D293,613 S | 1/1988 | Wingler |
| 4,739,755 A | 4/1988 | White et al. |
| 4,753,233 A | 6/1988 | Grimes |
| 4,764,989 A | 8/1988 | Bourgeois |
| 4,770,169 A | 9/1988 | Schmoegner et al. |
| 4,782,832 A | 11/1988 | Trimble et al. |
| 4,836,200 A | 6/1989 | Clark et al. |
| 4,856,508 A | 8/1989 | Tayebi |
| 4,907,584 A | 3/1990 | McGinnis |
| 4,915,104 A | 4/1990 | Marcy |
| 4,915,105 A | 4/1990 | Lee |
| 4,919,128 A | 4/1990 | Kopala et al. |
| 4,938,209 A | 7/1990 | Fry |
| 4,941,467 A | 7/1990 | Takata |
| 4,944,310 A | 7/1990 | Sullivan |
| 4,947,488 A | 8/1990 | Ashinoff |
| D310,431 S | 9/1990 | Bellm |
| 4,960,121 A | 10/1990 | Nelson et al. |
| 4,971,051 A | 11/1990 | Toffolon |
| 4,974,586 A | 12/1990 | Wandel et al. |
| 4,986,269 A | 1/1991 | Hakkinen |
| 5,005,571 A | 4/1991 | Dietz |
| 5,010,925 A | 4/1991 | Atkinson et al. |
| 5,016,625 A | 5/1991 | Hsu et al. |
| 5,031,261 A | 7/1991 | Fenner |
| 5,042,478 A | 8/1991 | Kopala et al. |
| D320,677 S | 10/1991 | Kumagai et al. |
| D321,419 S | 11/1991 | Wallace |

(56) References Cited

U.S. PATENT DOCUMENTS

| | | |
|---|---|---|
| 5,062,421 A | 11/1991 | Burns et al. |
| 5,065,756 A | 11/1991 | Rapoport |
| D322,318 S | 12/1991 | Sullivan |
| 5,074,297 A | 12/1991 | Venegas |
| 5,094,236 A | 3/1992 | Tayebi |
| 5,113,857 A | 5/1992 | Dickerman et al. |
| 5,121,745 A | 6/1992 | Israel |
| 5,148,802 A | 9/1992 | Sanders et al. |
| 5,164,652 A | 11/1992 | Johnson et al. |
| 5,231,979 A | 8/1993 | Rose et al. |
| 5,243,971 A | 9/1993 | Sullivan et al. |
| 5,245,995 A | 9/1993 | Sullivan et al. |
| D340,317 S | 10/1993 | Cole |
| 5,259,377 A | 11/1993 | Schroeder |
| 5,269,296 A | 12/1993 | Landis |
| 5,323,516 A | 6/1994 | Hartmann |
| 5,349,949 A | 9/1994 | Schegerin |
| 5,353,789 A | 10/1994 | Schlobohm |
| 5,355,878 A | 10/1994 | Griffiths et al. |
| 5,366,805 A | 11/1994 | Fujiki et al. |
| D354,128 S | 1/1995 | Rinehart |
| D355,484 S | 2/1995 | Rinehart |
| 5,400,776 A | 3/1995 | Bartholomew |
| 5,429,683 A | 7/1995 | Le Mitouard |
| 5,438,981 A | 8/1995 | Starr et al. |
| 5,441,046 A | 8/1995 | Starr et al. |
| 5,449,206 A | 9/1995 | Lockwood |
| 5,449,234 A | 9/1995 | Gipp et al. |
| 5,458,202 A | 10/1995 | Fellows et al. |
| 5,477,852 A | 12/1995 | Landis et al. |
| 5,513,634 A | 5/1996 | Jackson |
| 5,517,986 A | 5/1996 | Starr et al. |
| 5,518,802 A | 5/1996 | Colvin et al. |
| 5,533,506 A | 7/1996 | Wood |
| 5,540,223 A | 7/1996 | Starr et al. |
| 5,542,128 A | 8/1996 | Lomas |
| 5,551,419 A | 9/1996 | Froehlich et al. |
| 5,558,090 A | 9/1996 | James |
| 5,560,354 A | 10/1996 | Berthon-Jones et al. |
| 5,570,689 A | 11/1996 | Starr et al. |
| 5,588,423 A | 12/1996 | Smith |
| 5,595,174 A | 1/1997 | Gwaltney |
| 5,601,078 A | 2/1997 | Schaller et al. |
| D378,610 S | 3/1997 | Reischel et al. |
| 5,647,355 A | 7/1997 | Starr et al. |
| 5,649,532 A | 7/1997 | Griffiths |
| 5,657,752 A | 8/1997 | Landis et al. |
| 5,662,101 A | 9/1997 | Ogden et al. |
| 5,664,566 A | 9/1997 | Mcdonald et al. |
| 5,690,097 A | 11/1997 | Howard et al. |
| 5,697,363 A | 12/1997 | Hart |
| 5,724,965 A | 3/1998 | Handke et al. |
| 5,746,201 A | 5/1998 | Kidd |
| 5,752,510 A | 5/1998 | Goldstein |
| 5,755,578 A | 5/1998 | Contant et al. |
| 5,758,642 A | 6/1998 | Choi |
| 5,806,727 A | 9/1998 | Joseph |
| 5,842,470 A | 12/1998 | Ruben |
| 5,857,460 A | 1/1999 | Popitz |
| 5,878,743 A | 3/1999 | Zdrojkowski et al. |
| 5,884,624 A | 3/1999 | Barnett et al. |
| 5,896,857 A | 4/1999 | Hely et al. |
| 5,904,278 A | 5/1999 | Barlow et al. |
| 5,921,239 A | 7/1999 | McCall et al. |
| 5,937,851 A | 8/1999 | Serowski |
| 5,941,245 A | 8/1999 | Hannah et al. |
| 5,943,473 A | 8/1999 | Levine |
| 5,953,763 A | 9/1999 | Gouget |
| 5,966,745 A | 10/1999 | Schwartz et al. |
| 6,006,748 A | 12/1999 | Hollis |
| 6,016,804 A | 1/2000 | Gleason et al. |
| 6,017,315 A | 1/2000 | Starr et al. |
| 6,019,101 A | 2/2000 | Cotner et al. |
| 6,021,528 A | 2/2000 | Jurga |
| 6,039,044 A | 3/2000 | Sullivan |
| 6,050,260 A | 4/2000 | Daniell et al. |
| 6,050,294 A | 4/2000 | Makowan |
| 6,112,746 A | 9/2000 | Kwok et al. |
| 6,116,235 A | 9/2000 | Walters et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,135,109 A | 10/2000 | Blasdell et al. |
| 6,135,432 A | 10/2000 | Hebblewhite et al. |
| 6,192,886 B1 | 2/2001 | Rudolph |
| 6,196,223 B1 * | 3/2001 | Belfer ............... A41D 13/1176 128/205.25 |
| D440,302 S | 4/2001 | Wolfe |
| 6,272,933 B1 | 8/2001 | Gradon et al. |
| 6,292,985 B1 | 9/2001 | Grunberger |
| 6,298,850 B1 | 10/2001 | Argraves |
| 6,302,105 B1 | 10/2001 | Wickham et al. |
| D453,247 S | 1/2002 | Lee |
| 6,338,342 B1 | 1/2002 | Fecteau et al. |
| 6,341,382 B1 | 1/2002 | Ryvin et al. |
| 6,341,606 B1 | 1/2002 | Bordewick et al. |
| 6,347,631 B1 | 2/2002 | Hansen et al. |
| 6,355,878 B1 | 3/2002 | Kim |
| D455,891 S | 4/2002 | Biedrzycki |
| 6,371,110 B1 | 4/2002 | Peterson et al. |
| 6,374,826 B1 | 4/2002 | Gunaratnam et al. |
| 6,398,197 B1 | 6/2002 | Dickinson et al. |
| 6,412,488 B1 | 7/2002 | Barnett et al. |
| 6,418,928 B1 | 7/2002 | Bordewick et al. |
| 6,422,238 B1 | 7/2002 | Lithgow |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,457,473 B1 | 10/2002 | Brostrom et al. |
| 6,460,539 B1 | 10/2002 | Japuntich et al. |
| 6,467,483 B1 | 10/2002 | Kopacko et al. |
| 6,470,886 B1 | 10/2002 | Kopacko |
| 6,478,026 B1 | 11/2002 | Wood |
| 6,484,725 B1 | 11/2002 | Chi et al. |
| 6,488,664 B1 | 12/2002 | Solomon et al. |
| 6,491,034 B1 | 12/2002 | Gunaratnam et al. |
| 6,513,526 B2 | 2/2003 | Kwok et al. |
| 6,526,978 B2 | 3/2003 | Dominguez |
| 6,530,373 B1 | 3/2003 | Patron |
| 6,557,555 B1 | 5/2003 | Hollis |
| 6,561,188 B1 | 5/2003 | Ellis |
| 6,561,190 B1 | 5/2003 | Kwok |
| 6,561,191 B1 | 5/2003 | Kwok |
| 6,581,594 B1 | 6/2003 | Drew et al. |
| 6,581,601 B2 | 6/2003 | Ziaee |
| 6,581,602 B2 | 6/2003 | Kwok et al. |
| 6,584,975 B1 | 7/2003 | Taylor |
| 6,584,977 B1 | 7/2003 | Serowski |
| 6,588,424 B2 | 7/2003 | Bardel |
| 6,595,214 B1 | 7/2003 | Hecker et al. |
| 6,598,271 B2 | 7/2003 | Nire |
| 6,598,272 B2 | 7/2003 | Nire |
| 6,606,767 B2 | 8/2003 | Wong |
| 6,615,832 B1 | 9/2003 | Chen |
| 6,629,531 B2 | 10/2003 | Gleason et al. |
| 6,631,718 B1 | 10/2003 | Lovell |
| 6,634,357 B1 | 10/2003 | Hamilton |
| 6,634,358 B2 | 10/2003 | Kwok et al. |
| 6,637,434 B2 | 10/2003 | Noble |
| 6,644,315 B2 | 11/2003 | Ziaee |
| 6,644,316 B2 | 11/2003 | Bowman et al. |
| 6,647,597 B2 | 11/2003 | Reiter |
| 6,651,658 B1 | 11/2003 | Hill et al. |
| 6,651,663 B2 | 11/2003 | Barnett et al. |
| 6,659,102 B1 | 12/2003 | Sico |
| 6,662,803 B2 | 12/2003 | Gradon et al. |
| 6,668,828 B1 | 12/2003 | Figley et al. |
| 6,679,257 B1 | 1/2004 | Robertson et al. |
| 6,679,265 B2 | 1/2004 | Strickland et al. |
| 6,691,707 B1 | 2/2004 | Gunaratnam et al. |
| 6,712,072 B1 | 3/2004 | Lang |
| D488,600 S | 4/2004 | Pecci |
| 6,729,333 B2 | 5/2004 | Barnett et al. |

(56) References Cited

U.S. PATENT DOCUMENTS

| | | |
|---|---|---|
| 6,736,139 B1 | 5/2004 | Wix |
| D490,950 S | 6/2004 | Pecci |
| 6,772,761 B1 | 8/2004 | Rucker, Jr. |
| 6,796,308 B2 | 9/2004 | Gunaratnam et al. |
| 6,817,362 B2 | 11/2004 | Gelinas et al. |
| 6,823,869 B2 | 11/2004 | Raje et al. |
| 6,851,425 B2 | 2/2005 | Jaffre et al. |
| 6,851,428 B2 | 2/2005 | Dennis |
| 6,883,177 B1 | 4/2005 | Ouellette et al. |
| 6,889,692 B2 | 5/2005 | Hollis |
| 6,892,729 B2 | 5/2005 | Smith et al. |
| 6,895,965 B2 | 5/2005 | Scarberry et al. |
| 6,907,882 B2 | 6/2005 | Ging et al. |
| 6,918,390 B2 | 7/2005 | Lithgow et al. |
| 6,951,218 B2 | 10/2005 | Gradon et al. |
| 6,953,354 B2 | 10/2005 | Edirisuriya et al. |
| 6,990,691 B2 | 1/2006 | Klotz et al. |
| 7,004,165 B1 | 2/2006 | Salcido |
| 7,007,696 B2 | 3/2006 | Palkon et al. |
| 7,021,311 B2 | 4/2006 | Gunaratnam et al. |
| D520,140 S | 5/2006 | Chaggares |
| 7,066,178 B2 | 6/2006 | Gunaratnam et al. |
| 7,066,179 B2 | 6/2006 | Eaton et al. |
| 7,077,126 B2 | 7/2006 | Kummer et al. |
| D526,094 S | 8/2006 | Chen |
| 7,089,939 B2 | 8/2006 | Walker et al. |
| 7,096,864 B1 | 8/2006 | Mayer et al. |
| 7,100,610 B2 | 9/2006 | Biener et al. |
| 7,111,624 B2 | 9/2006 | Thudor et al. |
| D533,269 S | 12/2006 | McAuley et al. |
| 7,152,602 B2 | 12/2006 | Bateman et al. |
| 7,174,893 B2 | 2/2007 | Walker et al. |
| 7,178,525 B2 | 2/2007 | Matula |
| 7,178,528 B2 | 2/2007 | Lau |
| 7,185,652 B2 | 3/2007 | Gunaratnam et al. |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,255,106 B2 | 8/2007 | Gallem et al. |
| 7,260,440 B2 | 8/2007 | Selim et al. |
| 7,287,528 B2 | 10/2007 | Ho et al. |
| 7,290,546 B2 | 11/2007 | Sprinkle et al. |
| 7,296,575 B1 | 11/2007 | Radney |
| 7,318,437 B2 | 1/2008 | Gunaratnam et al. |
| 7,320,323 B2 | 1/2008 | Lang et al. |
| D567,366 S | 4/2008 | Betz et al. |
| 7,353,826 B2 | 4/2008 | Sleeper et al. |
| 7,353,827 B2 | 4/2008 | Geist |
| 7,406,966 B2 | 8/2008 | Wondka et al. |
| 7,448,386 B2 | 11/2008 | Ho et al. |
| D582,546 S | 12/2008 | Fujiura et al. |
| D586,906 S | 2/2009 | Stallard et al. |
| 7,487,772 B2 | 2/2009 | Ging et al. |
| 7,509,958 B2 | 3/2009 | Amarasinghe et al. |
| 7,523,754 B2 | 4/2009 | Lithgow et al. |
| D595,841 S | 7/2009 | McAuley et al. |
| 7,556,043 B2 | 7/2009 | Ho et al. |
| 7,562,658 B2 | 7/2009 | Madaus et al. |
| 7,568,482 B2 | 8/2009 | Jaffre et al. |
| 7,597,100 B2 | 10/2009 | Ging et al. |
| 7,658,189 B2 | 2/2010 | Davidson et al. |
| 7,665,464 B2 | 2/2010 | Kopacko et al. |
| 7,681,575 B2 | 3/2010 | Wixey et al. |
| 7,694,677 B2 | 4/2010 | Tang |
| 7,708,017 B2 | 5/2010 | Davidson et al. |
| 7,721,737 B2 | 5/2010 | Radney |
| 7,753,051 B2 | 7/2010 | Burrow et al. |
| 7,779,832 B1 | 8/2010 | Ho |
| 7,793,987 B1 | 9/2010 | Busch et al. |
| 7,810,497 B2 | 10/2010 | Pittman et al. |
| 7,814,911 B2 | 10/2010 | Bordewick et al. |
| 7,827,990 B1 | 11/2010 | Melidis et al. |
| 7,877,817 B1 | 2/2011 | Ho |
| 7,896,003 B2 | 3/2011 | Matula et al. |
| D635,661 S | 4/2011 | Stallard et al. |
| 7,931,024 B2 | 4/2011 | Ho et al. |
| 7,934,501 B2 | 5/2011 | Fu |
| 7,942,148 B2 | 5/2011 | Davidson et al. |
| D639,420 S | 6/2011 | D'Souza et al. |
| 7,958,893 B2 | 6/2011 | Lithgow et al. |
| 7,971,590 B2 | 7/2011 | Frater et al. |
| 7,975,694 B2 | 7/2011 | Ho |
| 7,992,560 B2 | 8/2011 | Burton et al. |
| 8,028,699 B2 | 10/2011 | Ho et al. |
| 8,042,538 B2 | 10/2011 | Ging et al. |
| 8,042,539 B2 | 10/2011 | Chandran et al. |
| 8,042,542 B2 | 10/2011 | Ging et al. |
| D652,914 S | 1/2012 | D'Souza et al. |
| 8,091,547 B2 | 1/2012 | Thudor et al. |
| 8,127,764 B2 | 3/2012 | Ho et al. |
| 8,132,270 B2 | 3/2012 | Lang et al. |
| 8,136,523 B2 | 3/2012 | Rudolph |
| 8,136,524 B2 | 3/2012 | Ging et al. |
| 8,136,525 B2 | 3/2012 | Lubke et al. |
| 8,146,595 B2 | 4/2012 | Sherman |
| 8,146,596 B2 | 4/2012 | Smith et al. |
| 8,171,933 B2 | 5/2012 | Xue et al. |
| 8,186,345 B2 | 5/2012 | Payton et al. |
| D661,796 S | 6/2012 | Andrews et al. |
| 8,196,583 B2 | 6/2012 | Radney |
| 8,245,711 B2 | 8/2012 | Matula et al. |
| 8,251,066 B1 | 8/2012 | Ho et al. |
| 8,254,637 B2 | 8/2012 | Abourizk et al. |
| 8,261,745 B2 | 9/2012 | Chandran et al. |
| 8,267,089 B2 | 9/2012 | Ho et al. |
| D668,408 S | 10/2012 | Kim et al. |
| 8,276,588 B1 | 10/2012 | Connor |
| 8,286,636 B2 | 10/2012 | Gunaratnam et al. |
| 8,291,906 B2 | 10/2012 | Kooij et al. |
| 8,297,285 B2 | 10/2012 | Henry et al. |
| 8,342,181 B2 | 1/2013 | Selvarajan et al. |
| 8,353,294 B2 | 1/2013 | Frater et al. |
| 8,371,302 B2 | 2/2013 | Ging et al. |
| 8,397,727 B2 | 3/2013 | Ng et al. |
| D681,192 S | 4/2013 | D'Souza et al. |
| 8,439,035 B2 | 5/2013 | Dantanarayana et al. |
| 8,443,807 B2 | 5/2013 | McAuley et al. |
| 8,453,641 B2 | 6/2013 | Payton et al. |
| D686,313 S | 7/2013 | Matula et al. |
| 8,479,726 B2 | 7/2013 | McAuley |
| 8,479,736 B2 | 7/2013 | Ging et al. |
| 8,479,741 B2 | 7/2013 | McAuley et al. |
| 8,490,623 B2 | 7/2013 | Berthon-Jones et al. |
| 8,490,624 B2 | 7/2013 | Berthon Jones et al. |
| 8,517,023 B2 | 8/2013 | Henry |
| 8,517,024 B2 | 8/2013 | Selvarajan et al. |
| 8,550,072 B2 | 10/2013 | Thudor et al. |
| 8,550,084 B2 | 10/2013 | Ng et al. |
| 8,567,404 B2 | 10/2013 | Davidson et al. |
| D693,461 S | 11/2013 | Rothermel |
| 8,573,212 B2 | 11/2013 | Lynch et al. |
| 8,596,271 B2 | 12/2013 | Matula et al. |
| 8,596,276 B2 | 12/2013 | Omura et al. |
| 8,616,211 B2 | 12/2013 | Davidson et al. |
| 8,622,057 B2 | 1/2014 | Ujhazy et al. |
| 8,631,793 B2 | 1/2014 | Omura et al. |
| 8,636,005 B2 | 1/2014 | Gradon et al. |
| 8,636,007 B2 | 1/2014 | Rummery et al. |
| 8,646,449 B2 | 2/2014 | Bowsher |
| 8,701,667 B1 | 4/2014 | Ho et al. |
| 8,714,157 B2 | 5/2014 | McAuley et al. |
| 8,720,444 B2 | 5/2014 | Chang |
| 8,733,358 B2 | 5/2014 | Lithgow et al. |
| 8,757,157 B2 | 6/2014 | Price et al. |
| 8,770,190 B2 | 7/2014 | Doherty et al. |
| 8,783,257 B2 | 7/2014 | McAuley et al. |
| 8,800,563 B2 | 8/2014 | Doherty et al. |
| 8,807,134 B2 | 8/2014 | Ho et al. |
| D716,440 S | 10/2014 | D'Souza et al. |
| 8,856,975 B2 | 10/2014 | Lang et al. |
| 8,857,435 B2 | 10/2014 | Matula et al. |
| 8,869,797 B2 | 10/2014 | Davidson et al. |

(56) References Cited

U.S. PATENT DOCUMENTS

| | | |
|---|---|---|
| 8,869,798 B2 | 10/2014 | Wells et al. |
| 8,875,709 B2 | 11/2014 | Davidson et al. |
| 8,887,728 B2 | 11/2014 | Boussignac et al. |
| 8,910,626 B2 | 12/2014 | Matula et al. |
| 8,931,484 B2 | 1/2015 | Melidis et al. |
| 8,944,061 B2 | 2/2015 | D'Souza et al. |
| 8,950,404 B2 | 2/2015 | Formica et al. |
| 8,960,196 B2 | 2/2015 | Henry |
| D724,282 S | 3/2015 | Irfan |
| 8,978,653 B2 | 3/2015 | Frater et al. |
| 8,985,117 B2 | 3/2015 | Gunaratnam et al. |
| 8,997,742 B2 | 4/2015 | Moore et al. |
| 9,010,330 B2 | 4/2015 | Barlow et al. |
| 9,010,331 B2 | 4/2015 | Lang et al. |
| 9,027,556 B2 | 5/2015 | Ng et al. |
| 9,032,955 B2 | 5/2015 | Lubke et al. |
| 9,032,956 B2 | 5/2015 | Scheiner et al. |
| 9,044,564 B2 | 6/2015 | Dravitzki et al. |
| 9,056,177 B2 | 6/2015 | Ho |
| 9,067,033 B2 | 6/2015 | Davidson et al. |
| 9,072,852 B2 | 7/2015 | McAuley et al. |
| 9,095,673 B2 | 8/2015 | Barlow et al. |
| 9,119,929 B2 | 9/2015 | McAuley et al. |
| 9,119,931 B2 | 9/2015 | D'Souza et al. |
| 9,132,256 B2 | 9/2015 | Gunaratnam et al. |
| 9,138,555 B2 | 9/2015 | McAuley et al. |
| 9,144,655 B2 | 9/2015 | McAuley et al. |
| 9,149,593 B2 | 10/2015 | Dravitzki et al. |
| 9,149,596 B2 | 10/2015 | Valcic et al. |
| 9,155,857 B2 | 10/2015 | Lalonde |
| 9,186,474 B1 | 11/2015 | Rollins |
| 9,211,388 B2 | 12/2015 | Swift et al. |
| 9,220,860 B2 | 12/2015 | Davidson et al. |
| 9,242,062 B2 | 1/2016 | Melidis et al. |
| 9,265,902 B2 | 2/2016 | Payton et al. |
| 9,265,909 B2 | 2/2016 | Ho et al. |
| 9,292,799 B2 | 3/2016 | McAuley et al. |
| 9,295,799 B2 | 3/2016 | McAuley et al. |
| D753,813 S | 4/2016 | Ozolins et al. |
| 9,320,566 B1 | 4/2016 | Alston, Jr. et al. |
| 9,320,866 B2 | 4/2016 | McAuley et al. |
| 9,333,315 B2 | 5/2016 | McAuley et al. |
| 9,339,621 B2 | 5/2016 | McAuley et al. |
| 9,339,622 B2 | 5/2016 | McAuley et al. |
| 9,339,624 B2 | 5/2016 | McAuley et al. |
| 9,375,545 B2 | 6/2016 | Darkin et al. |
| 9,381,316 B2 | 7/2016 | Ng et al. |
| 9,387,302 B2 | 7/2016 | Dravitzki et al. |
| D767,755 S | 9/2016 | D'Souza et al. |
| 9,457,162 B2 | 10/2016 | Ging et al. |
| 9,486,601 B2 | 11/2016 | Stallard et al. |
| 9,517,317 B2 | 12/2016 | McAuley et al. |
| 9,522,246 B2 | 12/2016 | Frater et al. |
| 9,539,405 B2 | 1/2017 | McAuley et al. |
| 9,550,038 B2 | 1/2017 | McAuley et al. |
| 9,561,338 B2 | 2/2017 | McAuley et al. |
| 9,561,339 B2 | 2/2017 | McAuley et al. |
| D784,516 S | 4/2017 | Prentice et al. |
| 9,757,533 B2 | 9/2017 | Ng et al. |
| 9,770,568 B2 | 9/2017 | Ng et al. |
| 9,884,160 B2 | 2/2018 | McAuley et al. |
| 9,901,699 B2 | 2/2018 | Veliss et al. |
| 9,907,922 B2 | 3/2018 | Stephenson et al. |
| 9,907,923 B2 | 3/2018 | Stephenson et al. |
| 9,950,130 B2 | 4/2018 | Stephenson et al. |
| 10,201,678 B2 | 2/2019 | Guney et al. |
| 10,258,757 B2 | 4/2019 | Allan et al. |
| 2001/0017134 A1 | 8/2001 | Bahr |
| 2001/0020474 A1 | 9/2001 | Hecker et al. |
| 2001/0029952 A1 | 10/2001 | Curran |
| 2002/0014241 A1 | 2/2002 | Gradon et al. |
| 2002/0020416 A1 | 2/2002 | Namey |
| 2002/0026934 A1 | 3/2002 | Lithgow et al. |
| 2002/0029780 A1 | 3/2002 | Frater |
| 2002/0043265 A1 | 4/2002 | Barnett et al. |
| 2002/0046755 A1 | 4/2002 | Voss |
| 2002/0053347 A1 | 5/2002 | Ziaee |
| 2002/0059935 A1 | 5/2002 | Wood |
| 2002/0096178 A1 | 7/2002 | Ziaee |
| 2002/0100479 A1 | 8/2002 | Scarberry et al. |
| 2002/0108613 A1 | 8/2002 | Gunaratnam et al. |
| 2002/0195108 A1 | 12/2002 | Mittelstadt et al. |
| 2003/0005509 A1 | 1/2003 | Kelzer |
| 2003/0005931 A1 | 1/2003 | Jaffre et al. |
| 2003/0005933 A1 | 1/2003 | Izuchukwu |
| 2003/0019495 A1 | 1/2003 | Palkon et al. |
| 2003/0019496 A1 | 1/2003 | Kopacko et al. |
| 2003/0029454 A1 | 2/2003 | Gelinas et al. |
| 2003/0037788 A1 | 2/2003 | Gallem et al. |
| 2003/0047185 A1 | 3/2003 | Olsen et al. |
| 2003/0075180 A1 | 4/2003 | Raje et al. |
| 2003/0075182 A1 | 4/2003 | Heidmann et al. |
| 2003/0089373 A1 | 5/2003 | Gradon et al. |
| 2003/0094177 A1 | 5/2003 | Smith et al. |
| 2003/0121519 A1 | 7/2003 | Estes et al. |
| 2003/0127101 A1 | 7/2003 | Dennis |
| 2003/0149384 A1 | 8/2003 | Davis et al. |
| 2003/0164170 A1 | 9/2003 | Drew et al. |
| 2003/0172936 A1 | 9/2003 | Wilkie et al. |
| 2003/0196655 A1 | 10/2003 | Ging et al. |
| 2003/0196656 A1 | 10/2003 | Moore |
| 2003/0196658 A1 | 10/2003 | Ging et al. |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2003/0217746 A1 | 11/2003 | Gradon et al. |
| 2003/0226564 A1 | 12/2003 | Liland |
| 2003/0236015 A1 | 12/2003 | Edirisuriya et al. |
| 2004/0025882 A1 | 2/2004 | Madaus et al. |
| 2004/0035427 A1 | 2/2004 | Bordewick et al. |
| 2004/0065328 A1 | 4/2004 | Amarasinghe et al. |
| 2004/0067333 A1 | 4/2004 | Amarasinghe |
| 2004/0094157 A1 | 5/2004 | Dantanarayana et al. |
| 2004/0107547 A1 | 6/2004 | Chung |
| 2004/0107968 A1 | 6/2004 | Griffiths |
| 2004/0112377 A1 | 6/2004 | Amarasinghe et al. |
| 2004/0112384 A1 | 6/2004 | Lithgow et al. |
| 2004/0112385 A1 | 6/2004 | Drew |
| 2004/0118406 A1 | 6/2004 | Lithgow et al. |
| 2004/0118412 A1 | 6/2004 | Piletti-Reyes |
| 2004/0134497 A1 | 7/2004 | Gunaratnam et al. |
| 2004/0139973 A1 | 7/2004 | Wright |
| 2004/0149280 A1 | 8/2004 | Semeniuk |
| 2004/0182398 A1 | 9/2004 | Sprinkle et al. |
| 2004/0211425 A1 | 10/2004 | Wang |
| 2004/0211427 A1 | 10/2004 | Jones et al. |
| 2004/0226566 A1 | 11/2004 | Gunaratnam et al. |
| 2004/0255949 A1 | 12/2004 | Lang |
| 2005/0011524 A1 | 1/2005 | Thomlinson et al. |
| 2005/0016532 A1 | 1/2005 | Farrell |
| 2005/0028822 A1 | 2/2005 | Sleeper et al. |
| 2005/0033247 A1 | 2/2005 | Thompson |
| 2005/0045182 A1 | 3/2005 | Wood et al. |
| 2005/0051177 A1 | 3/2005 | Wood |
| 2005/0066976 A1 | 3/2005 | Wondka |
| 2005/0076913 A1 | 4/2005 | Ho et al. |
| 2005/0092327 A1 | 5/2005 | Fini et al. |
| 2005/0098183 A1 | 5/2005 | Nash et al. |
| 2005/0121037 A1 | 6/2005 | Wood |
| 2005/0133038 A1 | 6/2005 | Rutter |
| 2005/0150497 A1 | 7/2005 | Eifler et al. |
| 2005/0155604 A1 | 7/2005 | Ging et al. |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0241644 A1 | 11/2005 | Guney et al. |
| 2006/0032504 A1 | 2/2006 | Burton et al. |
| 2006/0042629 A1 | 3/2006 | Geist |
| 2006/0042632 A1 | 3/2006 | Bishop et al. |
| 2006/0060200 A1 | 3/2006 | Ho et al. |
| 2006/0076019 A1 | 4/2006 | Ho |
| 2006/0081256 A1 | 4/2006 | Palmer |
| 2006/0096598 A1 | 5/2006 | Ho et al. |

(56) References Cited

U.S. PATENT DOCUMENTS

| | | |
|---|---|---|
| 2006/0107958 A1 | 5/2006 | Sleeper |
| 2006/0118117 A1 | 6/2006 | Berthon-Jones et al. |
| 2006/0124131 A1 | 6/2006 | Chandran et al. |
| 2006/0130844 A1 | 6/2006 | Ho et al. |
| 2006/0137690 A1 | 6/2006 | Gunaratnam et al. |
| 2006/0169286 A1 | 8/2006 | Eifler et al. |
| 2006/0174887 A1 | 8/2006 | Chandran et al. |
| 2006/0174892 A1 | 8/2006 | Leksutin et al. |
| 2006/0196511 A1 | 9/2006 | Lau et al. |
| 2006/0201514 A1 | 9/2006 | Jones et al. |
| 2006/0207599 A1 | 9/2006 | Busch et al. |
| 2006/0237017 A1 | 10/2006 | Davidson et al. |
| 2006/0237018 A1 | 10/2006 | McAuley et al. |
| 2006/0249159 A1 | 11/2006 | Ho |
| 2006/0254593 A1 | 11/2006 | Chang |
| 2006/0266361 A1 | 11/2006 | Hernandez |
| 2006/0266365 A1 | 11/2006 | Stallard |
| 2006/0283459 A1 | 12/2006 | Geiselhart et al. |
| 2006/0283461 A1 | 12/2006 | Lubke et al. |
| 2007/0000492 A1 | 1/2007 | Hansel et al. |
| 2007/0006879 A1 | 1/2007 | Thornton |
| 2007/0010786 A1 | 1/2007 | Casey et al. |
| 2007/0044804 A1 | 3/2007 | Matula, Jr. et al. |
| 2007/0089749 A1 | 4/2007 | Ho et al. |
| 2007/0107733 A1 | 5/2007 | Ho |
| 2007/0125385 A1 | 6/2007 | Ho et al. |
| 2007/0125387 A1 | 6/2007 | Zollinger et al. |
| 2007/0137653 A1 | 6/2007 | Wood |
| 2007/0142785 A1 | 6/2007 | Lundgaard et al. |
| 2007/0144525 A1 | 6/2007 | Davidson et al. |
| 2007/0157353 A1 | 7/2007 | Guney et al. |
| 2007/0163600 A1 | 7/2007 | Hoffman |
| 2007/0174952 A1 | 8/2007 | Jacob |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0221226 A1 | 9/2007 | Hansen et al. |
| 2007/0221227 A1 | 9/2007 | Ho |
| 2007/0227541 A1 | 10/2007 | Van Den |
| 2007/0246043 A1 | 10/2007 | Kwok et al. |
| 2007/0267017 A1 | 11/2007 | McAuley et al. |
| 2007/0295335 A1 | 12/2007 | Nashed |
| 2008/0032036 A1 | 2/2008 | Ito et al. |
| 2008/0035152 A1 | 2/2008 | Ho et al. |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0060648 A1 | 3/2008 | Thornton et al. |
| 2008/0060653 A1 | 3/2008 | Hallett et al. |
| 2008/0060657 A1 | 3/2008 | McAuley et al. |
| 2008/0083412 A1 | 4/2008 | Henry et al. |
| 2008/0099024 A1 | 5/2008 | Gunaratnam et al. |
| 2008/0105257 A1 | 5/2008 | Klasek et al. |
| 2008/0110464 A1 | 5/2008 | Davidson et al. |
| 2008/0142019 A1 | 6/2008 | Lewis |
| 2008/0171737 A1 | 7/2008 | Fensome |
| 2008/0178875 A1 | 7/2008 | Henry |
| 2008/0178886 A1 | 7/2008 | Lieberman et al. |
| 2008/0190432 A1 | 8/2008 | Blochlinger et al. |
| 2008/0190436 A1 | 8/2008 | Jaffe et al. |
| 2008/0196728 A1 | 8/2008 | Ho |
| 2008/0210241 A1 | 9/2008 | Schulz et al. |
| 2008/0223370 A1 | 9/2008 | Kim |
| 2008/0223373 A1 | 9/2008 | Chang |
| 2008/0230068 A1 | 9/2008 | Rudolph |
| 2008/0236586 A1 | 10/2008 | Mcdonald et al. |
| 2008/0257354 A1 | 10/2008 | Davidson et al. |
| 2008/0264422 A1 | 10/2008 | Fishman |
| 2008/0271739 A1 | 11/2008 | Facer et al. |
| 2008/0302366 A1 | 12/2008 | McGinnis et al. |
| 2008/0314388 A1 | 12/2008 | Brambilla et al. |
| 2008/0319334 A1 | 12/2008 | Yamamori |
| 2009/0014007 A1 | 1/2009 | Brambilla et al. |
| 2009/0014008 A1 | 1/2009 | Takishita et al. |
| 2009/0032024 A1 | 2/2009 | Burz et al. |
| 2009/0038619 A1 | 2/2009 | Ho et al. |
| 2009/0044808 A1 | 2/2009 | Guney et al. |
| 2009/0065729 A1 | 3/2009 | Worboys et al. |
| 2009/0078267 A1 | 3/2009 | Burz et al. |
| 2009/0095301 A1 | 4/2009 | Hitchcock et al. |
| 2009/0107504 A1 | 4/2009 | McAuley et al. |
| 2009/0110141 A1 | 4/2009 | Ging et al. |
| 2009/0114227 A1 | 5/2009 | Gunaratnam et al. |
| 2009/0114229 A1 | 5/2009 | Frater et al. |
| 2009/0120442 A1 | 5/2009 | Ho |
| 2009/0126739 A1 | 5/2009 | Ng et al. |
| 2009/0133697 A1 | 5/2009 | Kwok et al. |
| 2009/0139526 A1 | 6/2009 | Melidis et al. |
| 2009/0139527 A1 | 6/2009 | Ng et al. |
| 2009/0151729 A1 | 6/2009 | Judson et al. |
| 2009/0173349 A1 | 7/2009 | Hernandez et al. |
| 2009/0178679 A1 | 7/2009 | Lithaow et al. |
| 2009/0183734 A1 | 7/2009 | Kwok et al. |
| 2009/0183739 A1 | 7/2009 | Wondka |
| 2009/0188505 A1 | 7/2009 | Smart et al. |
| 2009/0223519 A1 | 9/2009 | Eifler et al. |
| 2009/0223521 A1 | 9/2009 | Howard |
| 2009/0272380 A1 | 11/2009 | Jaffre et al. |
| 2009/0277452 A1 | 11/2009 | Lubke et al. |
| 2010/0000538 A1 | 1/2010 | Edwards et al. |
| 2010/0000543 A1 | 1/2010 | Berthon-Jones et al. |
| 2010/0000544 A1 | 1/2010 | Blaszczykiewicz et al. |
| 2010/0043798 A1 | 2/2010 | Sullivan et al. |
| 2010/0051031 A1 | 3/2010 | Lustenberger et al. |
| 2010/0083961 A1 | 4/2010 | McAuley et al. |
| 2010/0108072 A1 | 5/2010 | D'Souza et al. |
| 2010/0132717 A1 | 6/2010 | Davidson et al. |
| 2010/0154798 A1 | 6/2010 | Henry et al. |
| 2010/0170516 A1 | 7/2010 | Grane |
| 2010/0192955 A1 | 8/2010 | Biener et al. |
| 2010/0199992 A1 | 8/2010 | Ho |
| 2010/0218768 A1 | 9/2010 | Radney |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0294281 A1 | 11/2010 | Ho |
| 2010/0307502 A1 | 12/2010 | Rummery et al. |
| 2010/0313891 A1 | 12/2010 | Veliss et al. |
| 2010/0319700 A1 | 12/2010 | Ng et al. |
| 2010/0326445 A1 | 12/2010 | Veliss et al. |
| 2011/0000492 A1 | 1/2011 | Veliss et al. |
| 2011/0005524 A1* | 1/2011 | Veliss ............... A61M 16/0666 128/206.24 |
| 2011/0048425 A1 | 3/2011 | Chang |
| 2011/0067704 A1 | 3/2011 | Kooij et al. |
| 2011/0072553 A1 | 3/2011 | Ho |
| 2011/0088699 A1 | 4/2011 | Skipper |
| 2011/0146684 A1 | 6/2011 | Wells et al. |
| 2011/0146685 A1 | 6/2011 | Allan et al. |
| 2011/0162654 A1 | 7/2011 | Carroll et al. |
| 2011/0197341 A1 | 8/2011 | Formica et al. |
| 2011/0220112 A1 | 9/2011 | Connor |
| 2011/0247625 A1 | 10/2011 | Boussignac et al. |
| 2011/0253143 A1 | 10/2011 | Ho et al. |
| 2011/0265796 A1 | 11/2011 | Amarasinghe et al. |
| 2011/0290253 A1 | 12/2011 | McAuley |
| 2011/0308520 A1 | 12/2011 | McAuley et al. |
| 2011/0308526 A1 | 12/2011 | Ho et al. |
| 2011/0315143 A1 | 12/2011 | Frater |
| 2012/0067349 A1 | 3/2012 | Barlow et al. |
| 2012/0080035 A1 | 4/2012 | Guney et al. |
| 2012/0125339 A1 | 5/2012 | Ho et al. |
| 2012/0132208 A1 | 5/2012 | Judson et al. |
| 2012/0132209 A1 | 5/2012 | Rummery |
| 2012/0138060 A1 | 6/2012 | Barlow |
| 2012/0138061 A1 | 6/2012 | Dravitzki et al. |
| 2012/0138063 A1 | 6/2012 | Eves et al. |
| 2012/0152255 A1 | 6/2012 | Barlow et al. |
| 2012/0167892 A1 | 7/2012 | Matula, Jr. |
| 2012/0190998 A1 | 7/2012 | Armitstead et al. |
| 2012/0204879 A1 | 8/2012 | Cariola et al. |
| 2012/0216819 A1 | 8/2012 | Raje et al. |
| 2012/0234326 A1 | 9/2012 | Mazzone et al. |
| 2012/0285452 A1 | 11/2012 | Amirav et al. |

(56) References Cited

U.S. PATENT DOCUMENTS

| | | |
|---|---|---|
| 2012/0285457 A1 | 11/2012 | Mansour et al. |
| 2012/0285469 A1 | 11/2012 | Ho et al. |
| 2012/0304999 A1 | 12/2012 | Swift et al. |
| 2012/0318265 A1 | 12/2012 | Amirav et al. |
| 2012/0318270 A1 | 12/2012 | McAuley et al. |
| 2012/0325219 A1 | 12/2012 | Smith |
| 2013/0000648 A1 | 1/2013 | Madaus et al. |
| 2013/0008446 A1 | 1/2013 | Carroll et al. |
| 2013/0008449 A1 | 1/2013 | Busch et al. |
| 2013/0037033 A1 | 2/2013 | Hitchcock et al. |
| 2013/0068230 A1 | 3/2013 | Jablonski |
| 2013/0092169 A1 | 4/2013 | Frater et al. |
| 2013/0133659 A1 | 5/2013 | Ng et al. |
| 2013/0133664 A1 | 5/2013 | Startare |
| 2013/0139822 A1 | 6/2013 | Gibson |
| 2013/0152918 A1 | 6/2013 | Rummery et al. |
| 2013/0160769 A1 | 6/2013 | Ng et al. |
| 2013/0186404 A1 | 7/2013 | Chien |
| 2013/0199537 A1 | 8/2013 | Formica et al. |
| 2013/0213400 A1 | 8/2013 | Barlow et al. |
| 2013/0220327 A1 | 8/2013 | Barlow et al. |
| 2013/0263858 A1 | 10/2013 | Ho et al. |
| 2013/0306066 A1 | 11/2013 | Selvarajan et al. |
| 2013/0306077 A1 | 11/2013 | Greenberg |
| 2013/0319422 A1 | 12/2013 | Ho et al. |
| 2013/0327336 A1 | 12/2013 | Burnham et al. |
| 2014/0026888 A1 | 1/2014 | Matula et al. |
| 2014/0034057 A1 | 2/2014 | Todd et al. |
| 2014/0041664 A1 | 2/2014 | Lynch et al. |
| 2014/0069433 A1 | 3/2014 | Walker et al. |
| 2014/0083428 A1 | 3/2014 | Rothermel et al. |
| 2014/0083430 A1 | 3/2014 | Matula, Jr. et al. |
| 2014/0094669 A1 | 4/2014 | Jaffe et al. |
| 2014/0096774 A1 | 4/2014 | Olen et al. |
| 2014/0137870 A1 | 5/2014 | Barlow et al. |
| 2014/0158136 A1 | 6/2014 | Romagnoli et al. |
| 2014/0166018 A1 | 6/2014 | Dravitzki et al. |
| 2014/0166019 A1 | 6/2014 | Ho et al. |
| 2014/0174444 A1 | 6/2014 | Darkin et al. |
| 2014/0174446 A1 | 6/2014 | Prentice et al. |
| 2014/0174447 A1 | 6/2014 | Ho et al. |
| 2014/0190486 A1 | 7/2014 | Dunn et al. |
| 2014/0202464 A1 | 7/2014 | Lithgow et al. |
| 2014/0209098 A1 | 7/2014 | Dunn et al. |
| 2014/0216462 A1 | 8/2014 | Law et al. |
| 2014/0224253 A1 | 8/2014 | Law et al. |
| 2014/0261412 A1 | 9/2014 | Guney et al. |
| 2014/0261432 A1 | 9/2014 | Eves et al. |
| 2014/0261434 A1 | 9/2014 | Ng et al. |
| 2014/0261435 A1 | 9/2014 | Rothermel |
| 2014/0261440 A1 | 9/2014 | Chodkowski |
| 2014/0283822 A1 | 9/2014 | Price et al. |
| 2014/0283826 A1 | 9/2014 | Murray et al. |
| 2014/0283831 A1 | 9/2014 | Foote et al. |
| 2014/0283841 A1 | 9/2014 | Chodkowski et al. |
| 2014/0283842 A1 | 9/2014 | Bearne et al. |
| 2014/0283843 A1 | 9/2014 | Eves et al. |
| 2014/0305433 A1 | 10/2014 | Rothermel |
| 2014/0305439 A1 | 10/2014 | Chodkowski et al. |
| 2014/0311492 A1 | 10/2014 | Stuebiger et al. |
| 2014/0311494 A1 | 10/2014 | Gibson et al. |
| 2014/0311496 A1* | 10/2014 | Rothermel ............ A61M 16/06 128/206.24 |
| 2014/0326243 A1 | 11/2014 | Nikolayevich et al. |
| 2014/0326246 A1 | 11/2014 | Chodkowski et al. |
| 2014/0338671 A1 | 11/2014 | Chodkowski et al. |
| 2014/0338672 A1 | 11/2014 | D'Souza et al. |
| 2014/0352134 A1 | 12/2014 | Ho |
| 2014/0360503 A1 | 12/2014 | Franklin et al. |
| 2014/0366886 A1 | 12/2014 | Chodkowski et al. |
| 2015/0013678 A1 | 1/2015 | McAuley et al. |
| 2015/0013682 A1 | 1/2015 | Hendriks et al. |
| 2015/0033457 A1 | 2/2015 | Tryner et al. |
| 2015/0040911 A1 | 2/2015 | Davidson et al. |
| 2015/0047640 A1 | 2/2015 | McCaslin |
| 2015/0059759 A1 | 3/2015 | Frater et al. |
| 2015/0083124 A1 | 3/2015 | Chodkowski et al. |
| 2015/0090266 A1 | 4/2015 | Melidis et al. |
| 2015/0128952 A1 | 5/2015 | Matula et al. |
| 2015/0128953 A1 | 5/2015 | Formica et al. |
| 2015/0174435 A1 | 6/2015 | Jones |
| 2015/0182719 A1 | 7/2015 | Grashow et al. |
| 2015/0193650 A1 | 7/2015 | Ho et al. |
| 2015/0196726 A1 | 7/2015 | Skipper et al. |
| 2015/0246198 A1 | 9/2015 | Bearne et al. |
| 2015/0246199 A1 | 9/2015 | Matula et al. |
| 2015/0335846 A1 | 11/2015 | Romagnoli et al. |
| 2015/0352308 A1 | 12/2015 | Cullen et al. |
| 2015/0367095 A1 | 12/2015 | Lang et al. |
| 2015/0374944 A1 | 12/2015 | Edwards et al. |
| 2016/0001028 A1 | 1/2016 | McAuley et al. |
| 2016/0008558 A1 | 1/2016 | Huddart et al. |
| 2016/0015922 A1 | 1/2016 | Chodkowski et al. |
| 2016/0022944 A1 | 1/2016 | Chodkowski et al. |
| 2016/0038707 A1 | 2/2016 | Allan et al. |
| 2016/0051786 A1 | 2/2016 | McAuley et al. |
| 2016/0067437 A1 | 3/2016 | Zollinger et al. |
| 2016/0067442 A1 | 3/2016 | Salmon et al. |
| 2016/0074613 A1 | 3/2016 | Davidson et al. |
| 2016/0106944 A1 | 4/2016 | McAuley et al. |
| 2016/0129210 A1 | 5/2016 | Matula, Jr. et al. |
| 2016/0166792 A1 | 6/2016 | Allan et al. |
| 2016/0213873 A1 | 7/2016 | McAuley et al. |
| 2016/0213874 A1 | 7/2016 | Davidson et al. |
| 2016/0296720 A1 | 10/2016 | Henry et al. |
| 2016/0310687 A1 | 10/2016 | McAuley et al. |
| 2017/0028148 A1 | 2/2017 | McAuley et al. |
| 2017/0065786 A1 | 3/2017 | Stephenson et al. |
| 2017/0072155 A1 | 3/2017 | Allan et al. |
| 2017/0119988 A1 | 5/2017 | Allan et al. |
| 2017/0143925 A1 | 5/2017 | McAuley et al. |
| 2017/0239438 A1 | 8/2017 | McAuley et al. |
| 2017/0246411 A1 | 8/2017 | Mashal et al. |
| 2017/0304574 A1 | 10/2017 | McAuley et al. |
| 2017/0326324 A1 | 11/2017 | McAuley et al. |
| 2017/0326325 A1 | 11/2017 | Allan et al. |
| 2017/0368288 A1 | 12/2017 | Stephens et al. |
| 2018/0250483 A1 | 9/2018 | Olsen et al. |
| 2018/0256844 A1 | 9/2018 | Galgali et al. |
| 2018/0289913 A1 | 10/2018 | Stephenson et al. |
| 2019/0001095 A1 | 1/2019 | Rose et al. |

FOREIGN PATENT DOCUMENTS

| | | |
|---|---|---|
| AU | 2003257274 | 3/2004 |
| AU | 2004201337 | 10/2005 |
| AU | 2008906390 | 12/2008 |
| AU | 2009900327 | 1/2009 |
| AU | 2009902731 | 6/2009 |
| AU | 2009904236 | 9/2009 |
| AU | 2014202233 A1 | 5/2014 |
| CA | 1311662 | 12/1992 |
| CA | 2440431 | 3/2004 |
| CN | 2172538 | 7/1994 |
| CN | 1784250 | 6/2006 |
| CN | 101378810 A | 3/2009 |
| CN | 101951984 A | 1/2011 |
| CN | 202666149 | 1/2013 |
| CN | 103619393 A | 3/2014 |
| DE | 895692 | 11/1953 |
| DE | 1226422 | 10/1966 |
| DE | 3026375 | 2/1982 |
| DE | 3719009 | 12/1988 |
| DE | 4004157 | 4/1991 |
| DE | 19603949 | 8/1997 |
| DE | 29723101 U1 | 7/1998 |
| DE | 200 17 940 | 2/2001 |
| DE | 19962515 | 7/2001 |
| DE | 10312881 | 5/2004 |
| DE | 102006011151 | 9/2007 |
| DE | 20 2010 011334 | 10/2010 |
| EP | 0 427 474 | 11/1990 |
| EP | 0 303 090 B1 | 4/1992 |
| EP | 0 747 078 | 12/1996 |

(56) References Cited

FOREIGN PATENT DOCUMENTS

| | | |
|---|---|---|
| EP | 0 982 042 | 3/2000 |
| EP | 1 099 452 | 5/2001 |
| EP | 1 116 492 | 7/2001 |
| EP | 1 152 787 | 11/2001 |
| EP | 0 830 180 | 3/2002 |
| EP | 1 245 250 | 10/2002 |
| EP | 1 258 266 | 11/2002 |
| EP | 1 582 231 | 10/2005 |
| EP | 1 632 262 | 3/2006 |
| EP | 1 259 279 | 11/2007 |
| EP | 2 054 114 | 5/2009 |
| EP | 1 488 820 | 9/2009 |
| EP | 2 130 563 | 12/2009 |
| EP | 2 145 645 | 1/2010 |
| EP | 2281596 A1 | 2/2011 |
| EP | 2 417 994 | 2/2012 |
| EP | 2 452 716 | 5/2012 |
| EP | 2451518 | 5/2012 |
| EP | 2 474 335 | 7/2012 |
| EP | 2 281 596 | 10/2012 |
| EP | 2 510 968 | 10/2012 |
| EP | 2 060 294 | 7/2013 |
| EP | 2 749 176 | 7/2014 |
| EP | 2 818 194 | 12/2014 |
| EP | 2818194 A1 | 12/2014 |
| EP | 1 646 910 | 8/2015 |
| EP | 2 954 920 | 12/2015 |
| FR | 1299470 | 7/1962 |
| FR | 2390116 | 12/1978 |
| FR | 2658725 | 8/1991 |
| FR | 2749176 | 12/1997 |
| GB | 190224431 | 12/1902 |
| GB | 309770 | 4/1929 |
| GB | 761263 | 11/1956 |
| GB | 823887 | 11/1959 |
| GB | 823897 | 11/1959 |
| GB | 880824 | 10/1961 |
| GB | 960115 | 6/1964 |
| GB | 979357 | 1/1965 |
| GB | 1072741 | 6/1967 |
| GB | 1467828 | 3/1977 |
| GB | 2133275 | 7/1984 |
| GB | 2173274 | 10/1986 |
| GB | 2186801 | 8/1987 |
| GB | 2393126 | 11/2004 |
| GB | 2385533 | 8/2005 |
| JP | 47-002239 Y1 | 1/1972 |
| JP | 48-8995 | 1/1973 |
| JP | 49-47495 | 4/1974 |
| JP | 49-85895 | 7/1974 |
| JP | 52-87095 | 6/1977 |
| JP | 57-182456 | 11/1982 |
| JP | 61-156943 | 9/1986 |
| JP | 61-185446 | 11/1986 |
| JP | 01-165052 | 11/1989 |
| JP | 02-126665 | 10/1990 |
| JP | 04-51928 | 5/1992 |
| JP | 09-010311 | 1/1997 |
| JP | 63-184062 | 11/1998 |
| JP | 11-000397 | 1/1999 |
| JP | 2000-325481 | 11/2000 |
| JP | 2004-016488 | 1/2004 |
| JP | 2005-529687 | 10/2005 |
| JP | 2007-516750 | 6/2007 |
| JP | 2007-527271 | 9/2007 |
| JP | 2008-526393 | 7/2008 |
| JP | 3160631 U | 7/2010 |
| NZ | 528029 | 3/2005 |
| NZ | 573196 | 7/2010 |
| NZ | 556198 | 10/2010 |
| NZ | 556043 | 1/2011 |
| NZ | 551715 | 2/2011 |
| NZ | 608551 | 10/2014 |
| RU | 2186597 | 8/2002 |
| SU | 726692 | 9/1981 |
| WO | WO 82/003548 | 10/1982 |
| WO | WO 94/002190 | 2/1994 |
| WO | WO 98/004310 | 2/1998 |
| WO | WO 98/04311 | 2/1998 |
| WO | WO 98/018514 | 5/1998 |
| WO | WO 98/024499 | 6/1998 |
| WO | WO 98/048878 | 11/1998 |
| WO | WO 98/57691 | 12/1998 |
| WO | WO 99/04842 | 2/1999 |
| WO | WO 99/006116 | 2/1999 |
| WO | WO 99/021618 | 5/1999 |
| WO | WO 99/43375 | 9/1999 |
| WO | WO 99/058181 | 11/1999 |
| WO | WO 99/058198 | 11/1999 |
| WO | WO 00/050122 | 8/2000 |
| WO | WO 00/057942 | 10/2000 |
| WO | WO 00/069497 | 11/2000 |
| WO | WO 00/074758 | 12/2000 |
| WO | WO 00/78381 | 12/2000 |
| WO | WO 00/078384 | 12/2000 |
| WO | WO 01/000266 | 1/2001 |
| WO | WO 01/32250 | 5/2001 |
| WO | WO 01/041854 | 6/2001 |
| WO | WO 01/058293 | 8/2001 |
| WO | WO 01/062326 | 8/2001 |
| WO | WO 01/62326 | 8/2001 |
| WO | WO 01/97892 | 12/2001 |
| WO | WO 01/097893 | 12/2001 |
| WO | WO 02/005883 | 1/2002 |
| WO | WO 02/007806 | 1/2002 |
| WO | WO 02/011804 | 2/2002 |
| WO | WO 02/047749 | 6/2002 |
| WO | WO 02/074372 | 9/2002 |
| WO | WO 03/013657 | 2/2003 |
| WO | WO 03/035156 | 5/2003 |
| WO | WO 03/076020 | 9/2003 |
| WO | WO 03/092755 | 11/2003 |
| WO | WO 04/007010 | 1/2004 |
| WO | WO 04/022146 | 3/2004 |
| WO | WO 04/022147 | 3/2004 |
| WO | WO 2004/021960 | 3/2004 |
| WO | WO 04/030736 | 4/2004 |
| WO | WO 04/041341 | 5/2004 |
| WO | WO 04/041342 | 5/2004 |
| WO | WO 04/071565 | 8/2004 |
| WO | WO 04/073777 | 9/2004 |
| WO | WO 04/073778 | 9/2004 |
| WO | WO 05/018523 | 3/2005 |
| WO | WO 05/021075 | 3/2005 |
| WO | WO 05/032634 | 4/2005 |
| WO | WO 05/051468 | 6/2005 |
| WO | WO 05/063328 | 7/2005 |
| WO | WO 05/068002 | 7/2005 |
| WO | WO 05/076874 | 8/2005 |
| WO | WO 05/079726 | 9/2005 |
| WO | WO 05/086943 | 9/2005 |
| WO | WO 05/097247 | 10/2005 |
| WO | WO 05/118040 | 12/2005 |
| WO | WO 05/118042 | 12/2005 |
| WO | WO 05/123166 | 12/2005 |
| WO | WO 06/000046 | 1/2006 |
| WO | WO 06/050559 | 5/2006 |
| WO | WO 06/069415 | 7/2006 |
| WO | WO 06/074513 | 7/2006 |
| WO | WO 06/074514 | 7/2006 |
| WO | WO 06/074515 | 7/2006 |
| WO | WO 06/096924 | 9/2006 |
| WO | WO 06/130903 | 12/2006 |
| WO | WO 06/138416 | 12/2006 |
| WO | WO 07/006089 | 1/2007 |
| WO | WO 07/009182 | 1/2007 |
| WO | WO 07/021777 | 2/2007 |
| WO | WO 07/022562 | 3/2007 |
| WO | WO 07/041751 | 4/2007 |
| WO | WO 07/041786 | 4/2007 |
| WO | WO 07/045008 | 4/2007 |
| WO | WO 07/048174 | 5/2007 |
| WO | WO 07/050557 | 5/2007 |
| WO | WO 07/053878 | 5/2007 |

(56) References Cited

FOREIGN PATENT DOCUMENTS

| | | |
|---|---|---|
| WO | WO 07/059504 | 5/2007 |
| WO | WO 07/139531 | 12/2007 |
| WO | WO 07/147088 | 12/2007 |
| WO | WO 08/003081 | 1/2008 |
| WO | WO 08/007985 | 1/2008 |
| WO | WO 08/030831 | 3/2008 |
| WO | WO 08/037031 | 4/2008 |
| WO | WO 08/040050 | 4/2008 |
| WO | WO 08/060295 | 5/2008 |
| WO | WO 08/063923 | 5/2008 |
| WO | WO 08/068966 | 6/2008 |
| WO | WO 08/070929 | 6/2008 |
| WO | WO 08/106716 | 9/2008 |
| WO | WO 08/148086 | 12/2008 |
| WO | WO 09/002608 | 12/2008 |
| WO | WO 09/026627 | 3/2009 |
| WO | WO 09/052560 | 4/2009 |
| WO | WO 09/059353 | 5/2009 |
| WO | WO 09/065368 | 5/2009 |
| WO | WO 09/092057 | 7/2009 |
| WO | WO 09/108995 | 9/2009 |
| WO | WO 09/143586 | 12/2009 |
| WO | WO 10/009877 | 1/2010 |
| WO | WO 10/066004 | 6/2010 |
| WO | WO 10/067237 | 6/2010 |
| WO | WO 10/071453 | 6/2010 |
| WO | WO 10/073138 | 7/2010 |
| WO | WO 10/073142 | 7/2010 |
| WO | WO 10/131189 | 11/2010 |
| WO | WO 10/135785 | 12/2010 |
| WO | WO 10/148453 | 12/2010 |
| WO | WO 2010/135785 | 12/2010 |
| WO | WO 11/014931 | 2/2011 |
| WO | WO 11/022751 | 3/2011 |
| WO | WO 11/059346 | 5/2011 |
| WO | WO 11/060479 | 5/2011 |
| WO | WO 11/077254 | 6/2011 |
| WO | WO 11/078703 | 6/2011 |
| WO | WO 12/020359 | 2/2012 |
| WO | WO 12/025843 | 3/2012 |
| WO | WO 12/040791 | 4/2012 |
| WO | WO 12/045127 | 4/2012 |
| WO | WO 12/052902 | 4/2012 |
| WO | WO 12/055886 | 5/2012 |
| WO | WO 2012/140514 | 10/2012 |
| WO | WO 2013/006899 | 1/2013 |
| WO | WO 13/056389 | 4/2013 |
| WO | WO 13/061260 | 5/2013 |
| WO | WO 13/066195 | 5/2013 |
| WO | WO 2013/064950 | 5/2013 |
| WO | WO 13/084110 | 6/2013 |
| WO | WO 13/168041 | 11/2013 |
| WO | WO 13/175409 | 11/2013 |
| WO | WO 13/186654 | 12/2013 |
| WO | WO 14/020468 | 2/2014 |
| WO | WO 14/020481 | 2/2014 |
| WO | WO 14/038959 | 3/2014 |
| WO | WO 14/045245 | 3/2014 |
| WO | WO 14/077708 | 5/2014 |
| WO | WO 14/109749 | 7/2014 |
| WO | WO 14/110622 | 7/2014 |
| WO | WO 14/141029 | 9/2014 |
| WO | WO 14/165906 | 10/2014 |
| WO | WO 14/175753 | 10/2014 |
| WO | WO 14/181214 | 11/2014 |
| WO | WO 14/183167 | 11/2014 |
| WO | WO 15/006826 | 1/2015 |
| WO | WO 15/022629 | 2/2015 |
| WO | WO 15/033287 | 3/2015 |
| WO | WO 15/057087 | 4/2015 |
| WO | WO 2015/057087 | 4/2015 |
| WO | WO 15/068067 | 5/2015 |
| WO | WO 15/092621 | 6/2015 |
| WO | WO 15/161345 | 10/2015 |
| WO | WO 16/000040 | 1/2016 |
| WO | WO 16/009393 | 1/2016 |
| WO | WO 2016/009393 | 1/2016 |
| WO | WO 16/032343 | 3/2016 |
| WO | WO 16/033857 | 3/2016 |
| WO | WO 16/041008 | 3/2016 |
| WO | WO 16/041019 | 3/2016 |
| WO | WO 2016/032343 | 3/2016 |
| WO | WO 2016/033857 | 3/2016 |
| WO | WO 16/075658 | 5/2016 |
| WO | WO 16/149769 | 9/2016 |
| WO | WO 17/049356 | 3/2017 |
| WO | WO 17/049357 | 3/2017 |
| WO | WO 18/007966 | 1/2018 |
| WO | WO 18/064712 | 4/2018 |

OTHER PUBLICATIONS

Chinese Examination Report, Application No. 201580045964.0, dated Jan. 17, 2019 in 8 pages.
Japanese Office Action, Patent Application No. 2017-511715, dated Jul. 1, 2019, in 4 pages.
Fisher & Paykel HC200 Series Nasal CPAP Blower & Heated Humidifier User Manual, 17 pp., May 1998.
Fisher & Paykel Healthcare Limited, Simplus Full Face Mask, 185048005 Reva, 2012.
Fisher & Paykel Healthcare, FlexiFit® 431 Full Face Mask instructions, 2010, 4 pp.
Fisher & Paykel Healthcare, FlexiFit™ 431 Full Face Mask, specification sheet, 2004, 2 pp.
Fisher & Paykel Healthcare, Interface Solutions Product Profile, 2006, 12 pp.
Fisher & Paykel MR810 Manual, Rev. C, 2004, 43 pp.
HomeDepot.com—Ring Nut Sales Page (Retrieved Oct. 16, 2015 from http://www.homedepot.com/p/Everbilt-1-2-in-Galvanized-HexNut-804076/20464- 7893), 4 pp.
Malloy, 1994, Plastic Part Design for Injection Molding, Hanswer Gardner Publications, Inc, Cincinnati, OH, 14 pp.
Merriam-Webster's Collegiate Dictionary, Eleventh Edition, 2004, pp. 703, 905, 1074, 1184.
Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-seri- es-cpap-humidifier-manual.pdf front cover, pp. 3-4 and 6.
ResMed Exhibit, FlexiFitr™ 431, product brochure, web pages (Wayback Machine), 2006, 23 pp.
ResMed Origins Brochure (Retrieved Apr. 17, 2016 from http://www.resmed.com/us/dam/documents/articles/resmedorigins.pdf), 64 pp.
ResMed Ultra Mirage™ Full Face Mask, product brochure, 2004, 2 pp.
ResMed Ultra Mirage™ Full Face Mask, product brochure, web pages (Wayback Machine), 2006, 9 pp.
ResMed, Jun. 29, 1997, Mask Frames (Source: Wayback Machine Internet Archive); http://web.archive.org/web/19970629053430/http://www.resmed.com- /maskframes/mask.htm, 2 pp.
ResMed, Mirage Swift™ Nasal Pillows System from ResMed, product brochure, 2004, 6 pp.
ResMed, Mirage Swift™ Nasal Pillows System: User's Guide, product brochure, 2004, 11 pp.
ResMed, Mirage Vista™ Nasal Mask: Components Card, product brochure, 2005, 1 p.
The American Heritage Dictionary of the English Language, Fourth Edition, 2006, pp. 1501, 1502, 1650.
WeddingBands,com—Men's Wedding Ring Shopping Page (Retrieved Oct. 16, 2015 from http://www.weddingbands.com/ProductPop.sub.--weddingsub.--band- s,sub.--metal/48214W.html), 3 pp.
U.S. Appl. No. 60/842,741, dated Sep. 7, 2006, 30 pp.
U.S. Appl. No. 61/064,406, 34 pages, copy provided by USPTO on Feb. 23, 2009.
U.S. Appl. No. 61/071,893, 43 pages, copy provided by USPTO on Feb. 23, 2009.

(56) References Cited

OTHER PUBLICATIONS

U.S. Appl. No. 61/136,617, 82 pages, copy provided by USPTO on Feb. 23, 2009.
Australian Examination Report in patent application No. 2012265597 dated Dec. 19, 2013, 5 pages.
Australian examination report in patent application No. 2016202801, dated Jun. 20, 2016, 2 pp.
Australian examination eport in patent application No. 2016204384, dated Aug. 5, 2016, 2 pp.
Australian examination report in patent application No. 2016222390, dated Jul. 3, 2017, 3 pp.
Australian Examination Report in patent application No. 2007273324, dated May 22, 2012, 3 pages.
Australian Examination Report in patent application No. 2010241390, dated Jan. 9, 2015, 4 pages.
Australian Examination Report in patent application No. 2010241390, dated Sep. 28, 2016, 4 pages.
Australian Examination Report in patent application No. 2010246985, dated Mar. 4, 2014, 5 pages.
Australian Examination Report in patent application No. 2015201920, dated Jul. 20, 2015, 3 pages.
Australian Examination Report in patent application No. 2015202814, dated Aug. 14, 2015, 8 pages.
Australian Examination Report in patent application No. 2016202799, dated May 31, 2016, 2 pages.
Australian examination report in patent application No. 2016202801, dated Jun. 20, 2016, 2 pages.
Australian examination report in patent application No. 2016203303, dated Jan. 18, 2017, 4 pp.
Australian Examination Report in patent application No. 2016204384, dated Aug. 5, 2016, 2 pages.
Australian examination report in patent application No. 2017200991, dated Oct. 13, 2017, 3 pages.
Australian examination report in patent application No. 2017201021, dated Apr. 7, 2017, 6 pages.
Australian Examination Report in patent application no. 2018204754, dated Dec. 14, 2018, 3 pp.
Australian examination report dated May 8, 2019 in patent application No. 2018267634, 5 pages.
Canadian Examination Report in patent application No. 2655839, dated Oct. 4, 2013, 2 pages.
Canadian examination report in patent application No. 2764382, dated Feb. 2, 2016, 3 pp.
Canadian Examination Report in patent application No. 2780310, dated Apr. 18, 2017, 3 pp.
Canadian Examination Report in patent application No. 2780310, dated Jul. 26, 2016, 4 pages.
Canadian examination report in patent application No. 2814601, dated Aug. 8, 2017, 5 pp.
Canadian Examination Report in patent application No. 2890556, dated Jan. 27, 2016, 3 pages.
Canadian Examination Report in patent application No. 2890556, dated Nov. 28, 2016, 4 pages.
Canadian Examination Report in patent application No. 2918167, dated Oct. 3, 2016, 4 pages.
Chinese first office action dated Aug. 27, 2018 in patent application No. 201710012119.4.
Chinese examination report in patent application 201080061122.1, dated Jul. 17, 2015, 10 pp.
Chinese Examination Report in patent application No. 2007800266164, dated Feb. 17, 2011, 5 pages.
Chinese examination report in patent application No. 201080028029.0, dated Jan. 19, 2015, 16 pages.
Chinese Examination Report in patent application No. 201080028029.0, dated Mar. 27, 2014, 16 pages.
Chinese Examination Report in patent application No. 201080028029.0, dated Sep. 14, 2015, 3 pages.
Chinese examination report in patent application No. 201080061122.1, dated Apr. 1, 2016, 5 pages.
Chinese Examination Report in patent application No. 201080061122.1, dated Jul. 17, 2015, 10 pages.
Chinese examination report in patent application No. 201080061122.1, dated Sep. 3, 2014, 9 pp. (English translation).
Chinese examination report in patent application No. 201180059469.7, dated May 15, 2017, 5 pp. (English translation).
Chinese examination report in patent application No. 201210080441,8, dated Mar. 24, 2014, 4 pp. (English translation).
Chinese examination report in patent application No. 201210080441.8, dated Dec. 1, 2014, 11 pp. (English translation).
Chinese examination report in patent application No. 201610116121.1, dated Sep. 28, 2017, 5 pages.
Chinese examination report in patent application No. 201610261300.4, dated Dec. 5, 2017, 22 pp. (English translation).
European Examination Report in patent application No. 07808683,2, dated Jul. 8, 2015, 8 pages.
European Examination Report in patent application No. 09746823.5, dated Apr. 3, 2017, 2 pages.
European Extended Search Report for Patent Application No. 12770681.0, dated Oct. 15, 2014, 6 pages.
European extended search report in patent application No. 09746823.5, dated May 12, 2016, 11 pp.
European Extended Search Report in patent application No. 10774623,2, dated Sep. 8, 2015, 7 pages.
European Extended Search Report in patent application No. 10830251.4, dated Sep. 4, 2015, 7 pages.
European extended search report in patent application No. 11834691.5, dated Apr. 3, 2017, 9 pp.
European Extended Search Report in patent application No. 17179765.7, dated Dec. 11, 2017, 8 pages.
European Extended Search Report, Application No. 09819444.2, dated Apr. 2, 2014, 8 pages.
European partial supplementary search report in patent application No. 07860972.4, dated Sep. 20, 2017, 15 pp.
European Search Report and Written Opinion in patent application No. 09746823.5, dated May 12, 2016, 11 pages.
European Search Report in patent application No. 11830981.4, dated Aug. 24, 2015, 6 pages.
European Summons to Attend Oral Proceedings and Written Opinion in patent application No. 09746823.5, dated Dec. 13, 2017, 7 pages.
European examination report dated Oct. 11, 2018 in patent application No. 13825539.1.
Great Britain Combined Search and Examination Report in patent application No. GB1406401.8, dated May 7, 2014, 4 pages.
Great Britain Combined Search and Examination Report in patent application No. GB1406402.6, dated May 7, 2014, 6 pages.
Great Britain Examination Report in patent application No. GB1119385.1, dated May 9, 2013, 4 pages.
Great Britain examination report in patent application No. GB1501499.6, dated Jun. 1, 2017, 8 pp.
Great Britain Search and Examination Report, in patent application No. GB1210075.6, dated Mar. 14, 2013, 2 pages.
Indian Office Action in Patent Application No. 5250/KOLNP/2008, dated May 23, 2017, 8 pages.
International Search Report for Application No. PCT/NZ2005/000062—May 27, 2005.
International Search Report for International application No. PCT/NZ2007/000185, dated Oct. 31, 2007, in 3 pages.
International Search Report, PCT/NZ2009/000072, dated Jul. 28, 2009, 4 pages.
International Preliminary Report on Patentability (IPRP), International application No. PCT/NZ2009/000219, dated Apr. 12, 2011, 9 pages.
International Search Report, International application No. PCT/NZ2009/000219, dated Feb. 2, 2010, 3 pages.
International Preliminary Report on Patentability and Written Opinion of the ISA, International application No. PCT/NZ2010/000229, dated May 22, 2012, 14 pages.
International Search Report, PCT/NZ2010/000229, dated Mar. 18, 2011, 8 pages.
International Search Report, PCT/NZ2011/000211, dated Feb. 17, 2012, 4 pages.

(56) References Cited

OTHER PUBLICATIONS

International Search Report; PCT/NZ2012/000199; dated Jan. 21, 2013; 4 pages.
International Search Report and Written Opinion in application No. PCT/IB2012/000858, dated Aug. 13, 2012.
International Search Report in PCT/NZ2013/000138, dated Dec. 4, 2013, 7 pp.
International Search Report and Written Opinion for International Application No. PCT/NZ2013/000155, dated Dec. 6, 2013.
International Search Report in PCT/NZ2014/000021, dated May 20, 2014, 10 pp.
International Search Report, PCT/NZ2015/050119, dated Nov. 20, 2015 in 6 pages.
International Search Report and Written Opinion for PCT/IB/2015/055412, dated Oct. 12, 2015.
International Search Report, Application No. PCT/IB2016/051212, dated Jun. 8, 2016, in 10 pages.
International Search Report, Application No. PCT/IB2016/054365, dated Oct. 5, 2016, in 7 pages.
International Search Report, Application No. PCT/IB2016/054539; 6 pages; Dec. 6, 2016.
International Preliminary Report on Patentability in PCT/NZ2015/050068, dated Nov. 29, 2016.
International Search Report in PCT/NZ2015/050068, dated Oct. 29, 2015, 7 pp.
Japanese Examination Report in patent application No. 2012-510418, dated Feb. 10, 2014, 4 pages.
Japanese Examination Report in patent application No. 2012-538784, dated Aug. 25, 2014, 3 pages.
Japanese Examination Report in patent application No. 2012-538784, dated Aug. 5, 2015, 8 pages.
Japanese Examination Report in patent application No. 2012-538784, dated Jul. 25, 2016, 2 pages.
Japanese Examination Report in patent application No. 2015-098324, dated Jul. 22, 2015, 8 pages.
Japanese Notification of Reason for Rejection in patent application No. 2015-526496, dated Apr. 24, 2017, 13 pp.
Japanese Notification of Reason for Rejection in patent application No. 2016-166028, dated Jun. 19, 2017, 7 pp.
Japanese notification of reason for rejection in patent application No. 2012-538784, dated Aug. 5, 2015, 8 pp.
Written Opinion of the International Searching Authority, PCT/NZ2013/000139, dated Nov. 1, 2013, 5 pages.
Written Opinion of the International Searching Authority; PCT/NZ2012/000199; dated Jan. 21, 2013; 4 pages.
Written Opinion, PCT/NZ2011/00021, dated Feb. 17, 2012, 7 pages.
Petition for Inter Partes Review of U.S. Pat. No. 8,479,741 Pursuant to 35 U.S.C. §§ 311-19, 37 C.F.R. § 42, IPR2016-01714, dated Sep. 7, 2016.
Patent Owner Preliminary Response to Petition for Inter Partes Review of U.S. Pat. No. 8,479,741, IPR2016-01714, filed Dec. 14, 2016.
Decision Denying Institution of Inter Partes Review of U.S. Pat. No. 8,479,741 Pursuant to 37 C.F.R. § 42.108, IPR2016-01714, entered Mar. 10, 2017.
Declaration of Dr. John Izuchukwu, Ph.D., P.E., U.S. Pat. No. 8,443,807, IPR Nos. 2016-1726 & 2016-1734, dated Sep. 7, 2016, 232 pages.
Declaration of Dr. John Izuchukwu, Ph.D., P.E., U.S. Pat. No. 8,479,741, IPR Nos. 2016-1714 & 2016-1718, dated Sep. 7, 2016, 155 pages.
Petition for Inter Partes Review of U.S. Pat. No. 8,479,741 Pursuant to 35 U.S.C. §§ 311-19, 37 C.F.R. § 42, IPR2016-01718, dated Sep. 7, 2016.
Patent Owner Preliminary Response to Petition for Inter Partes Review of U.S. Pat. No. 8,479,741, IPR2016-01718, filed Dec. 16, 2016.
Decision Denying Institution of Inter Partes Review of U.S. Pat. No. 8,479,741 Pursuant to 37 C.F.R. § 42.108, IPR2016-01718, entered Mar. 13, 2017.
Petition for Inter Partes Review of U.S. Pat. No. 8,443,807 Pursuant to 35 U.S.C. §§ 311-19, 37 C.F.R. § 42, IPR2016-01726, dated Sep. 7, 2016.
Patent Owner Preliminary Response to Petition for Inter Partes Review of U.S. Pat. No. 8,443,807, IPR2016-01726, filed Dec. 13, 2016.
Decision Denying Institution of Inter Partes Review of U.S. Pat. No. 8,443,807 Pursuant to 37 C.F.R. § 42.108, IPR2016-01726, entered Mar. 6, 2017.
Petition for Inter Partes Review of U.S. Pat. No. 8,443,807 Pursuant to 35 U.S.C. §§ 311-19, 37 C.F.R. § 42, IPR2016-01734, dated Sep. 7, 2016.
Patent Owner Preliminary Response to Petition for Inter Partes Review of U.S. Pat. No. 8,443,807, IPR2016-01734, filed Dec. 22, 2016.
Decision Denying Institution of Inter Partes Review of U.S. Pat. No. 8,443,807 Pursuant to 37 C.F.R. § 42.108, IPR2016-01734, entered Mar. 13, 2017.
File History of U.S. Pat. No. 8,479,741 to McAuley et al, published Oct. 1, 2009.
File History of U.S. Pat. No, 8,443,807 to McAuley et al, published Jan. 7, 2010.
Patent Owner's Complaint for *Fisher & Paykel Healthcare Ltd.* v. *ResMed Corp.*, Case No. 2:16-cv-06099-R-AJW (C.D. Cal.), dated Aug. 15, 2016.
Patent Owner's Notice of Voluntary Dismissal Without Prejudice for *Fisher & Paykel Healthcare Ltd.* v. *ResMed Corp.*, Case No. 2:16-cv-06099-R-AJW (C.D. Cal.), dated Aug. 16, 2016.
Patent Owner's Complaint for *Fisher & Paykel Healthcare Ltd.* v. *ResMed Corp.*, Case No. 3:16-cv-02068-GPC-WVG (S.D. Cal.), dated Aug. 16, 2016.
Petitioners' Complaint for *ResMed Inc., et al.* v. *Fisher & Paykel Healthcare Corp. Ltd., et al.*, Case No. 3:16-cv-02072-JAH-MDD (S.D. Cal.), dated Aug. 16, 2016.
Petitioners' Notice of Voluntary Dismissal Without Prejudice for *ResMed Inc., et al.* v. *Fisher & Paykel Healthcare Corp. Ltd., et al.*, Case No. 3:16-cv-02072-JAH-MDD (S.D. Cal.), dated Aug. 18, 2016.
Statutory Declaration made by Alistair Edwin McAuley, Apr. 9, 2015, in the matter of an Opposition by *Fisher & Paykel Healthcare Limited* of Australian patent application 2009221630 in the name of ResMed Limited.
Examination Report for Australian Application No. 2016227361; dated Oct. 8, 2019; 6 pages.
Examination Report; Chinese Application No. 201580045964.0; dated Oct. 10, 2019; 16 total pages (including translation).

* cited by examiner

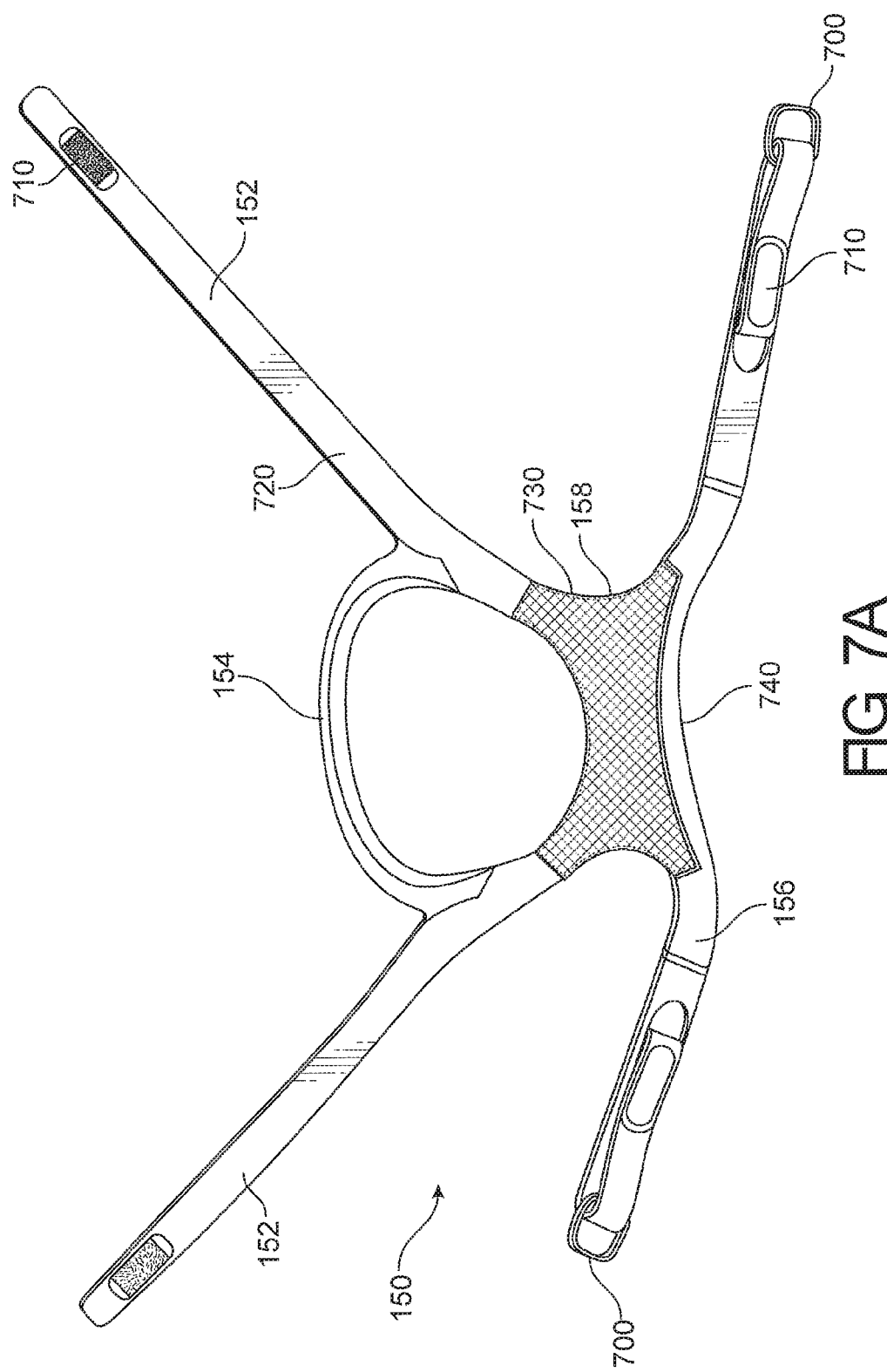

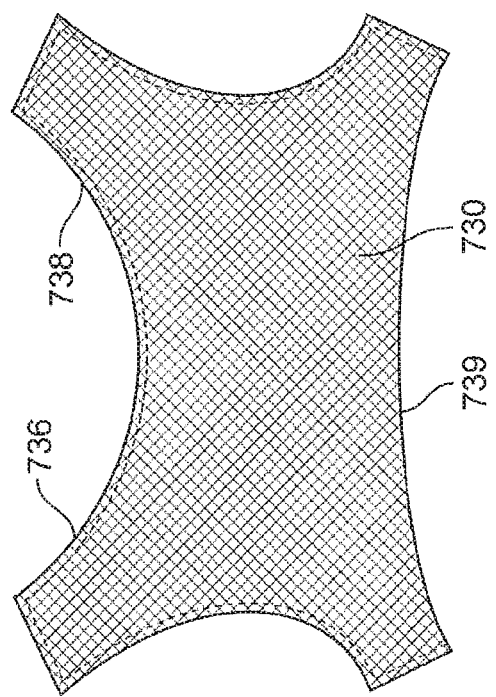
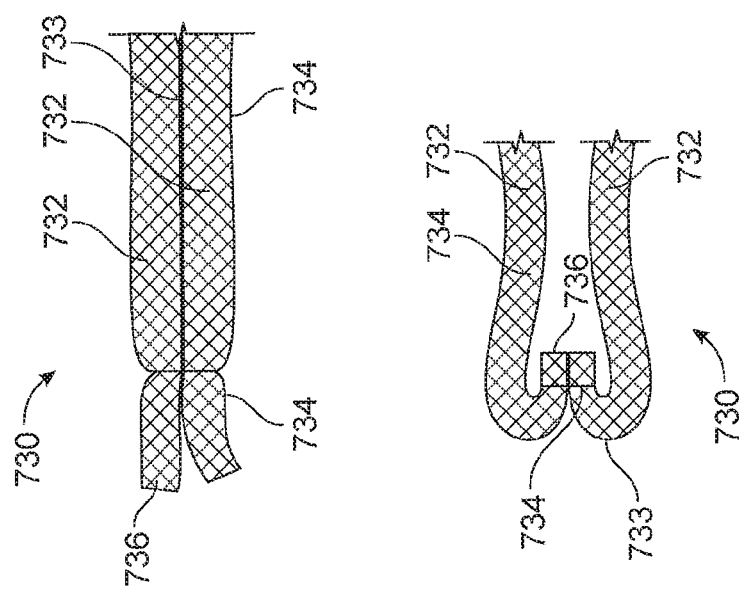
FIG. 7B

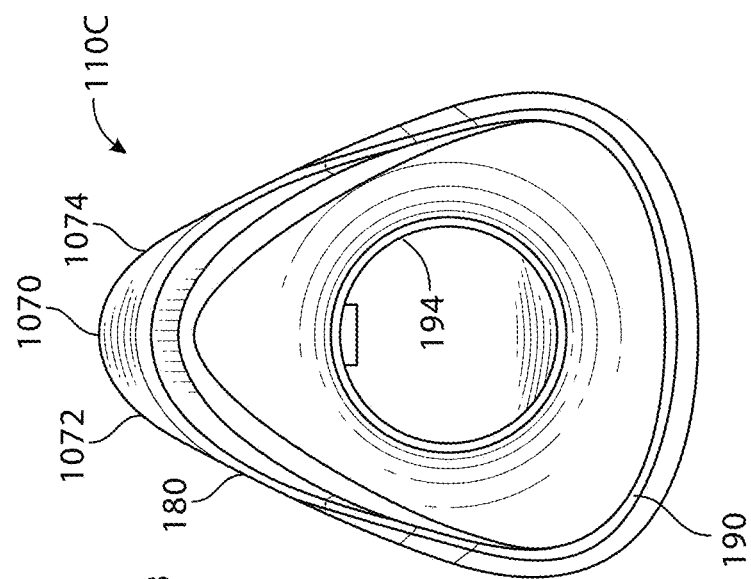
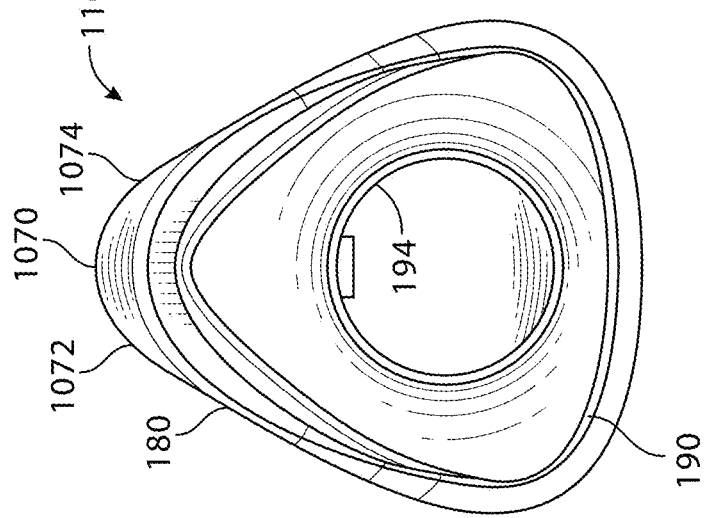
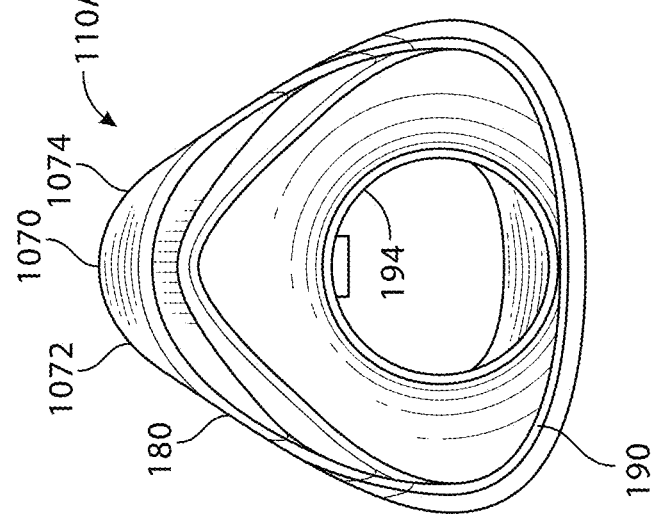

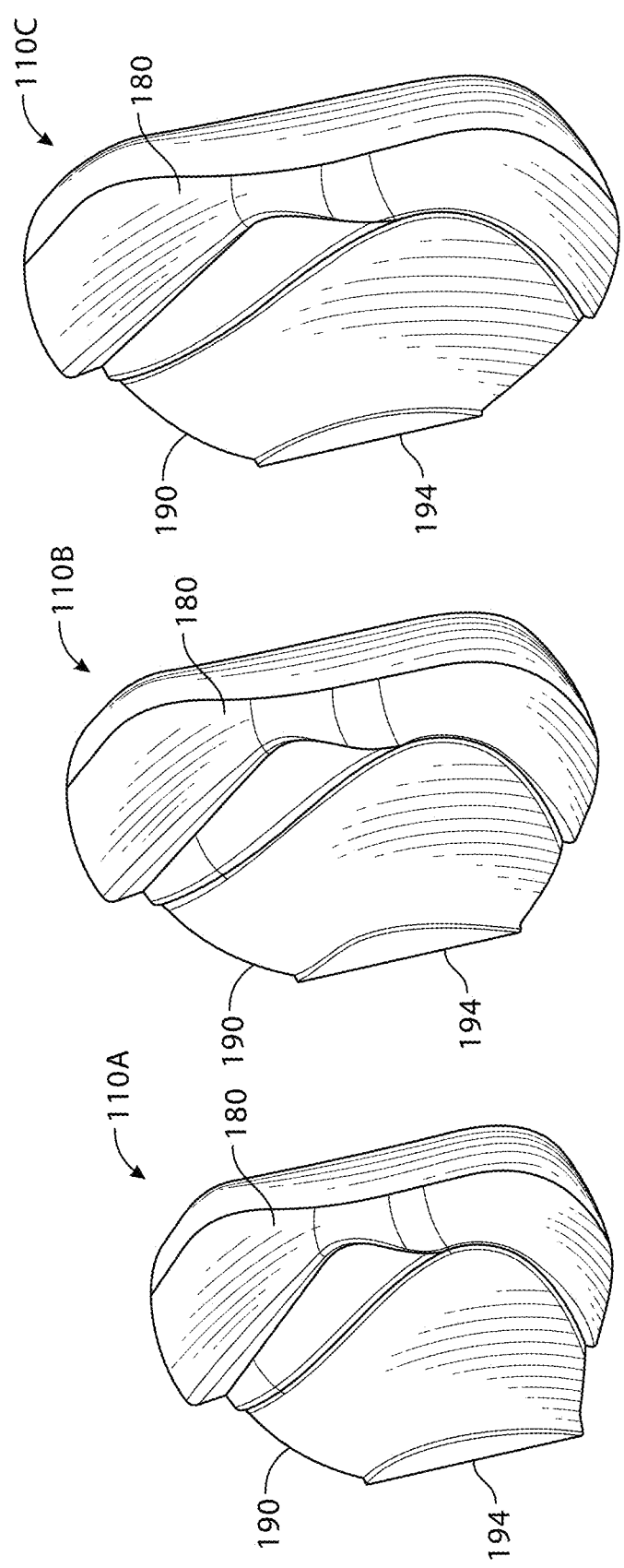

RESPIRATORY MASK AND RELATED PORTIONS, COMPONENTS OR SUB-ASSEMBLIES

INCORPORATION BY REFERENCE TO PRIORITY APPLICATIONS

This application is related to and claims priority from U.S. Provisional Patent Application Nos. 62/041,236, filed Aug. 25, 2014, 62/096,481, filed Dec. 23, 2014, 62/041,234, filed Aug. 25, 2014 and 62/041,262, filed Aug. 25, 2014, the entireties of which are hereby incorporated by reference herein and made a part of the present disclosure.

BACKGROUND

Field

The present disclosure generally relates to respiratory masks that cover at least one of a nose and a mouth of a user to supply respiratory gas under positive pressure. More particularly, certain aspects of the present disclosure relate to a respiratory mask with one or more of a removable ball jointed elbow, one or more detachable forehead pieces, and spacer fabric headgear. The disclosure also relates to seal cushion arrangements.

Description of Related Art

Respiratory masks can be used to provide respiratory gases to a user under positive pressure. In configurations that include a ball joint, it may be possible for dirt to build up between the ball joint and the socket. Removal of this dirt may be difficult with the ball joint and socket connected. It is also possible for cleaning products to build up in the connection between the ball joint and socket as a result of the surfaces being inaccessible for manual cleaning. The buildup of dirt and/or cleaning products may affect the hygiene of the mask and, thus, limit its useful lifetime. The ball joint is usually permanently connected to its corresponding socket, or it is at least very difficult to remove and/or insert. In some instances removal of the ball joint may require considerable force and may result in permanent damage to the mask.

Respiratory masks are typically available in a range of fixed sizes to suit users with differing facial geometries. This generally involves the manufacture of the entire mask, or at least the major mask components, in a range of sizes; which in turn increases the tooling and manufacturing costs associated with the mask. Another problem associated with fixed mask sizes is that it is possible that a single fixed size mask is not suitable for a particular user's facial geometries. A user's facial geometry may be such that, in order to achieve the best fit possible, the user requires each of the mask components in a different size, which is not possible with a fixed size mask.

Headgear for respiratory masks can traditionally be heavy, bulky, and hot to wear. This can lead to discomfort for the user.

Respiratory masks can have removable cushion modules that can be available in a plurality of sizes. In some cases, the different sizes are simply scaled up from one another in one or more dimensions. Other dimensions can remain the same throughout the different sizes.

Further, a large variety of respiratory masks have been devised. Many of these masks are configured to provide sealed communication with a user's airway by sealing around parts of the user's nose and/or mouth. These masks are commonly used to provide therapies such as, but not limited to, non-invasive ventilation (NW) and continuous positive airway pressure (CPAP). CPAP therapy is commonly used to treat obstructive sleep apnea (OSA) and involves providing a constant supply of pressurized air to a user's airway. This splints the airway open, thus minimizing airway collapse and reducing apneas. As part of this therapy, a bias-flow venting system is required to flush exhaled carbon dioxide ($CO_2$) from within the mask to prevent rebreathing.

Common bias-flow venting systems include arrays of holes that may be located on various respiratory mask components, such as elbows and mask frames. These holes are often positioned and aligned in clusters and in such a way that a concentrated flow of air is exhausted from them. The venting system can become a source of discernable drafts and noise. Drafts and noise can be annoying to both the user and/or their bed partner and may result in reduced compliance with the therapy. A number of approaches have been tried to alleviate these discomforts.

SUMMARY

The systems, methods and devices described herein have innovative aspects, no single one of which is indispensable or solely responsible for their desirable attributes. Without limiting the scope of the claims, some of the advantageous features will now be summarized.

It is an object of the present disclosure to provide one or more constructions or methods that will at least go some way towards improving on the above or that will at least provide the public with a useful choice.

In accordance with at least one of the embodiments disclosed herein, a cushion module for a respiratory interface is provided including a seal housing constructed from a relatively rigid material, the seal housing defining an aperture configured to allow a breathing gas to enter an interior of the cushion module, and a seal supported by the seal housing and having an upper portion and a lower portion. The seal further includes a face contacting surface configured to contact the face of a user and create at least a substantial seal with the face of the user, the face contacting surface having an inner edge defining an opening in the face contacting surface. The upper portion of the seal includes a reduced stiffness portion defined between a first boundary and a second boundary such that the reduced stiffness portion deforms in response to forward movement of an upper portion of the face contacting surface, wherein an angle defined between the first boundary and the second boundary is at least about 20 degrees.

According to a further aspect, the angle between the first boundary and the second boundary is at least about 25 degrees.

According to a further aspect, the angle between the first boundary and the second boundary is between about 27 degrees and about 34 degrees.

According to a further aspect, the angle between the first boundary and the second boundary is one of about 27 degrees, about 29 degrees and about 34 degrees.

According to a further aspect, a distance between a point on a centerline of the upper portion and a point on the centerline of the lower portion of the face contacting surface of the seal varies by more than 2 mm between a neutral position and a depressed position of the reduced stiffness region.

According to a further aspect, the distance between the point on a centerline of the upper portion and the point on the centerline of the lower portion of the face contacting surface of the seal varies by at least about 5 mm, at least about 6 mm, at least about 8 mm or at least about 10 mm or at least about 12 mm between the neutral position and the depressed position of the reduced stiffness region.

According to a further aspect, a portion of the seal defining the face contacting surface comprises a pair of nose pads positioned on each side of the opening in the upper portion of the seal, wherein an entirety of each of the nose pads is spaced outwardly from the opening.

According to a further aspect, the nose pads are the thickest portions of the portion of the seal defining the face contact surface.

According to a further aspect, the cushion module includes a pair of thickened outer peripheral portions defined by the portion of the seal defining the face contacting surface, wherein at least a portion of the thickened outer peripheral portions are positioned below the nose pads.

According to a further aspect, at least a portion of the thickened outer peripheral portions are positioned above the nose pads.

According to a further aspect, a continuous portion of the inner edge of the opening defines a thickness of equal to or less than 0.6 mm, wherein the continuous portion of the inner edge extends inwardly from the inner edge at least 1 mm and extends along at least an entirety of the upper portion of the seal.

According to a further aspect, a section of the continuous portion of the inner edge located within 0.5 mm of the inner edge is equal to or less than 0.4 mm in thickness.

According to a further aspect, the upper portion of the seal defines a nose bridge portion that contacts a bridge of the user's nose, wherein the nose bridge portion of the opening defines a continuously curved portion of the inner edge.

According to a further aspect, a width of the nose bridge portion is equal to or less than about 11 mm.

According to a further aspect, a vertical dimension of a vertical center of the nose bridge portion is equal to or greater than about 15 mm.

According to a further aspect, a depth between a rearmost point of the nose bridge portion and a lower edge of the nose bridge portion on the vertical center of the seal is at least about 4 mm.

According to a further aspect, the reduced stiffness portion comprises a front wall having a height of at least about 7 mm.

According to a further aspect, wherein the height of the front wall is between about 7.3 mm and about 7.7 mm.

According to a further aspect, a thickness of the front wall and a top wall progressively increases from a lower end of the front wall to a rearward end of the top wall.

According to a further aspect, a distance between a point on a centerline of the upper portion and a point on the centerline of the lower portion of the face contacting surface of the seal varies by more than 2 mm between a neutral position and a depressed position of the reduced stiffness region.

According to a further aspect, the distance between the point on a centerline of the upper portion and the point on the centerline of the lower portion of the face contacting surface of the seal varies by at least about 5 mm, at least about 6 mm, at least about 8 mm or at least about 10 mm or at least about 12 mm between the neutral position and the depressed position of the reduced stiffness region.

According to a further aspect, the distance varies between about 90 mm to about 84 mm between the neutral position and the depressed position of the reduced stiffness region.

According to a further aspect, the distance varies by at least about 5 percent between the neutral position and the depressed position of the reduced stiffness region.

According to a further aspect, the distance varies by at least about 6 and ⅔ percent between the neutral position and the depressed position of the reduced stiffness region.

According to a further aspect, the angle is different between the sizes of the cushion modules in at least two different sizes.

According to a further aspect, the cushion module includes a small, medium and large size, wherein the angle of the small size is greater than the angles of one or both of the medium and large sizes.

According to a further aspect, the angle of the large size is less than the angles of one or both of the small and medium sizes.

According to a further aspect, the angle of the small size is about 34 degrees, the angle of the medium size is about 29 degrees and the angle of the large size is about 27 degrees.

In accordance with at least one of the embodiments disclosed herein, a respiratory mask is provided and includes a frame portion configured to support a seal, wherein the seal is configured to form a substantially airtight seal with a user's face, and a conduit connector comprising a ball joint end. The frame portion defines an opening configured to receive the ball joint end of the conduit connector, the frame portion comprising a conduit connector removal notch configured to provide a leverage point for removal of the conduit connector. The conduit connector includes a portion configured to be received in the conduit connector removal notch to facilitate removal of the conduit connector from the frame portion.

According to a further aspect, the ball joint includes an end surface, the end surface comprising a tapered chamfer that defines an angle relative to a remainder of the end surface.

According to a further aspect, the ball joint comprises a rear edge, the rear edge being angled along a truncation axis, the rear edge being angled toward the lower portion of the elbow. The ball joint being a truncated ball along a truncation axis. In this aspect the rear edge is angled such that the length of the upper edge of the ball or ball joint is greater than the length of the lower edge of the ball or ball joint.

According to a further aspect, the opening is defined by an insert of the frame portion.

According to a further aspect, the conduit connector is an elbow.

According to a further aspect, the frame portion includes a cushion module that supports the seal and a headgear connector portion configured to be connected to a headgear.

According to a further aspect, the frame portion further includes a male forehead piece connector configured to connect to a separate forehead piece, which provides for a connection to a headgear.

According to a further aspect, the forehead piece is provided in multiple different sizes.

According to a further aspect, the conduit connector is removable from the opening when oriented to a predetermined position.

According to a further aspect, in combination with a headgear, the headgear comprising a spacer fabric pad located at the rear of the headgear.

According to a further aspect, the spacer fabric region includes two or more layers.

According to a further aspect, the two or more layers are sewn together at the edges with the wrong side of the fabric facing out, and then flipped right-side out so that the raw edges are on the inside.

In accordance with at least one of the embodiments disclosed herein, a cushion module for a respiratory interface is provided and includes a seal housing constructed from a relatively rigid material, the seal housing defining an aperture configured to allow a breathing gas to enter an interior of the cushion module, and a seal supported by the seal housing and having a first rolling portion, a second rolling portion and a lower portion. The seal further includes a face contacting surface configured to contact the face of a user and create at least a substantial seal with the face of the user, the face contacting surface having an inner edge defining an opening in the face contacting surface. The first rolling portion of the seal rotates about a first axis in response to forward movement of an upper portion of the face contacting surface, and the second rolling portion of the seal rotates about a second axis in response to forward movement of the upper portion of the face contacting surface.

According to a further aspect, an undeformed length is defined as a length of the seal between a nasal contact point and a chin contact point when the first and second rolling portions are undeformed. A partially deformed length is defined as a length of the seal between the nasal contact point and the chin contact point when the first rolling portion is fully deformed in response to forward movement of the upper portion of the face contacting surface and the second rolling portion is undeformed. A deformed length is defined as a length of the seal between the nasal contact point and the chin contact point when the first and second rolling portions are fully deformed in response to forward movement of the upper portion of the face contacting surface. The deformed length is shorter than both the undeformed length and the partially deformed length.

According to a further aspect, the difference between the undeformed length and the deformed length is greater than the difference between the undeformed length and the partially deformed length.

According to a further aspect, a difference between the undeformed length and the deformed length is approximately 17 mm.

According to a further aspect, the first and second rolling portions rotate simultaneously in response to forward movement of the upper portion of the face contacting surface.

According to a further aspect, the seal further includes a first thickened region between the upper portion of the face contacting surface and the first rolling portion, and a second thickened region between the first and second rolling portions of the seal. The first and second thickened regions prevent collapse of the first and second rolling portions in response to forward movement of the upper portion of the face contacting surface.

In accordance with at least one of the embodiments disclosed herein, a bias flow venting system for a respiratory mask is provided and includes a tube providing a flow path for a supply of pressurized air to the respiratory mask, and an annular array of exhaust holes formed within the tube. Exhausted air from the respiratory mask exits the tube through the exhaust holes.

According to a further aspect, the tube further includes a wall and a helical bead positioned on an outer surface of the wall.

According to a further aspect, the exhaust holes extend radially through the tube.

According to a further aspect, the exhaust holes are formed by laser drilling.

According to a further aspect, the exhaust holes extend radially through the helical bead.

According to a further aspect, the exhaust holes are positioned around an entire perimeter of the tube.

According to a further aspect, the tube is constructed from a flexible material and configured to deform along a central axis of the tube.

According to a further aspect, the exhaust holes are spaced along a length of the tube at regular intervals.

According to a further aspect, spacing between the exhaust holes increase or decrease along a length of the tube.

According to a further aspect, a pitch of the helical bead varies along a length of the tube.

According to a further aspect, the exhaust holes are disposed at a non-orthogonal angle with respect to a central axis of the tube.

In accordance with at least one of the embodiments disclosed herein, a bias-flow venting system for a respiratory mask is provided and includes an annular component connected to the respiratory mask and providing a flow path for a supply of pressurized air to the respiratory mask, the annular component having an array of exhaust holes extending radially through the annular component, and the exhaust holes providing an outlet for exhausted air from the respiratory mask to exit the annular component, and a shroud positioned around the annular component and defining a plenum chamber around the exhaust holes.

According to a further aspect, the exhaust holes are formed by laser drilling.

According to a further aspect, the exhaust holes are spaced around an entire perimeter of the annular component.

According to a further aspect, the shroud further comprising a conical surface facing the annular component, wherein the conical surface defines a portion of the plenum chamber.

According to a further aspect, the annular component further comprising a socket insert portion configured to surround and retain a ball joint within the socket insert.

According to a further aspect, the socket insert portion further includes an outer perimeter, an inner perimeter, front and rear insert surfaces, and exhaust holes. The inner perimeter is defined by a front bearing surface and a rear bearing surface, and the rear bearing surface is defined by a series of intermittent surfaces.

According to a further aspect, the intermittent surfaces are spaced apart by recesses.

According to a further aspect, the front bearing surface further includes a substantially spherical annular surface contacting the ball joint and providing a substantially airtight seal with the ball joint.

According to a further aspect, the recesses have substantially rectangular profiles defined by an outer recess wall, a front recess wall and two side walls.

According to a further aspect, the exhaust holes are configured to extend radially through the outer recess wall and the outer perimeter.

According to a further aspect, the insert socket has a substantially C-shaped profile, the socket having an outer perimeter and an inner perimeter separated by a front wall to define an annular channel between the outer perimeter and the inner perimeter, the inner perimeter having a front bearing surface that contacts the ball joint and provides a substantially airtight seal with the ball joint, and the outer perimeter connected to the respiratory mask.

According to a further aspect, the outer perimeter has a snap fit bump that interlocks with a snap fit connector of the respiratory mask.

According to a further aspect, an elbow connector positioned between the annular component and the respiratory mask. The annular component further includes a flange extending radially outward from an outer wall of the annular component, wherein the shroud and the flange define the plenum chamber.

In accordance with at least one of the embodiments disclosed herein, a respiratory mask assembly is provided and includes a mask frame, a seal housing configured to form a substantially airtight seal with a user's face, an elbow connector having a first end connected to an air supply and a second end having a ball joint disposed, and a socket insert portion positioned between the mask frame and the seal housing and configured to retain the ball joint within the socket insert. The socket insert portion has an array of exhaust holes extending through the socket insert, the exhaust holes providing an outlet for exhausted air from the seal housing to exit the socket insert.

According to a further aspect, the socket insert portion further includes an outer perimeter, an inner perimeter, front and rear insert surfaces, and exhaust holes. The inner perimeter is defined by a front bearing surface and a rear bearing surface, and the rear bearing surface is defined by a series of intermittent surfaces.

According to a further aspect, the intermittent surfaces are spaced apart by recesses.

According to a further aspect, the front bearing surface further includes a substantially spherical annular surface contacting the ball joint and providing a substantially airtight seal with the ball joint.

According to a further aspect, the recesses have substantially rectangular profiles defined by an outer recess wall, a front recess wall and two side walls.

According to a further aspect, the exhaust holes are configured to extend radially through the outer recess wall and the outer perimeter.

According to a further aspect, the insert socket has a substantially C-shaped profile, the insert socket having an outer perimeter and an inner perimeter separated by a front wall to define an annular channel between the outer perimeter and the inner perimeter, the inner perimeter having a front bearing surface that contacts the ball joint and provides a substantially airtight seal with the ball joint, and the outer perimeter connected to the seal housing.

According to a further aspect, the outer perimeter of the insert socket has a snap fit bump that interlocks with a snap fit connector of the seal housing.

According to a further aspect, the mask frame further includes a shroud positioned around the socket insert portion and defining a plenum chamber around the exhaust holes.

In accordance with at least one of the embodiments disclosed herein, a respiratory mask assembly is provided and includes a seal housing configured to form a substantially airtight seal with a user's face, the seal housing having an outer wall with an array of exhaust holes extending therethrough, the exhaust holes providing an outlet for exhausted air to exit the seal housing, an elbow connector having a first end connected to an air supply and a second end having a ball joint disposed, a socket insert portion positioned between the mask frame and the seal housing and configured to retain the ball joint within the socket insert, and a shroud extending from the outer wall and angled towards the elbow connector, the shroud and the outer wall defining a plenum chamber around the exhaust holes.

In accordance with at least one of the embodiments disclosed herein, a respiratory mask is provided and includes a mask body defining a breathing chamber, an opening to the breathing chamber and a bias flow vent comprising a plurality of vent holes configured to permit gases to exit the breathing chamber through the plurality of vent holes, the mask body configured for connection to a gases supply conduit such that a supply of breathing gas can be provided to the breathing chamber through the opening, a seal supported by the mask body and configured to create at least a substantial seal with a user's face, the seal configured to surround at least one of a nose and a mouth of the user, and a shroud supported relative to the mask body and spaced from a portion of the mask body containing the bias flow vent to define a plenum chamber that receives the gases exiting the breathing chamber through the plurality of vent holes.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

FIGS. 7A and 7B show various views of the headgear of the present disclosure.

FIGS. 8A to 8C illustrate front views of several cushion modules of different sizes.

FIGS. 9A to 9C illustrate side views of the cushion modules of FIGS. 8A to 8C.

DETAILED DESCRIPTION

Figure 1A:
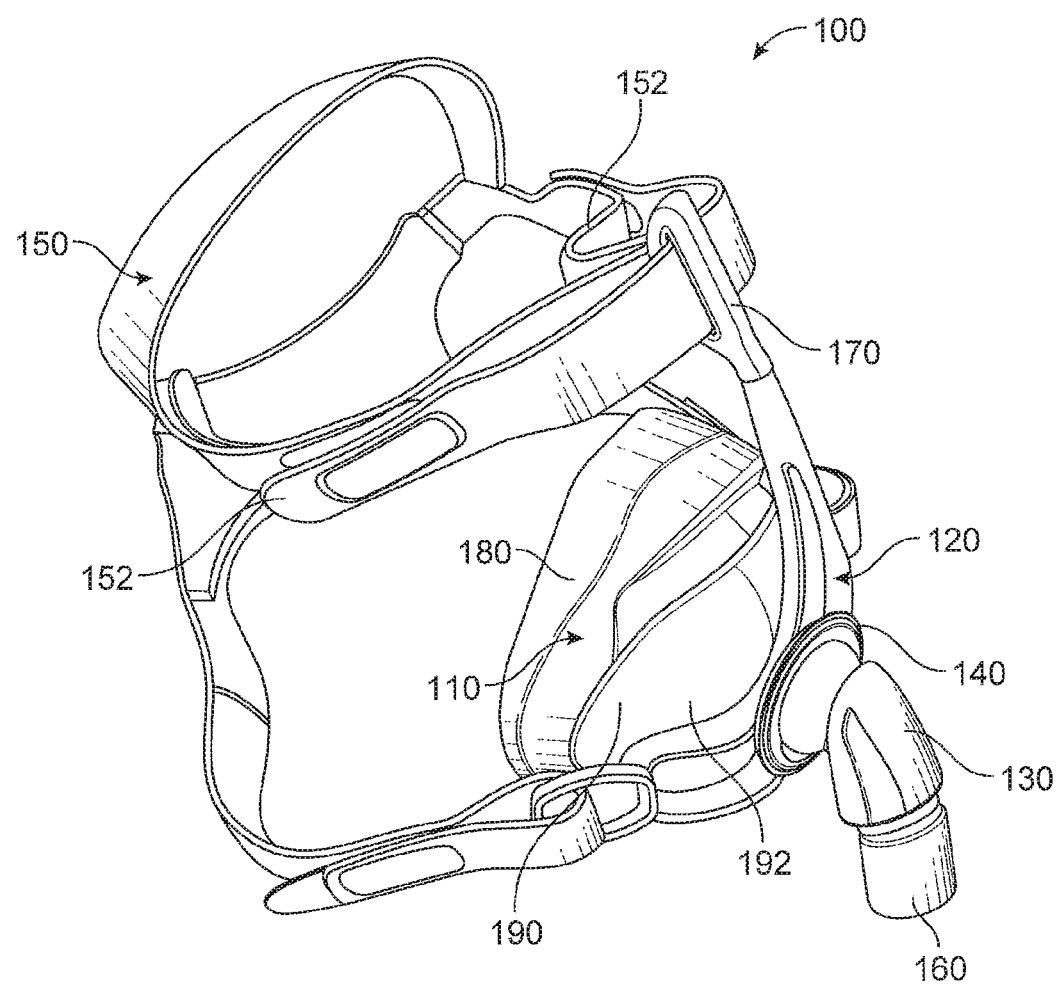
FIG. 1A is a perspective view of the respiratory mask of the present disclosure.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. As used herein the terms 'front', 'rear', 'upper' and 'lower' shall refer to the location of a part or portion of a respiratory mask in relation to a user. Wherein, 'front' refers to a location that is distal to the user (when the mask is in use) and 'rear' refers to a location that is proximal to the user by comparison. The terms 'upper' and 'lower' refer to the location of a part or component of a mask relative to the rest of the mask when the mask is in use and the user is sitting in an upright position. Moreover, terms such as "first," "second," "third," and so on may be used to describe separate components. Such terminology may include the words specifically mentioned above, derivatives thereof, and words of similar import.

The term 'seal housing' refers to a respiratory mask component that is configured to provide a breathing chamber that substantially surrounds a user's nose and/or mouth (when in use). A seal housing may comprise a seal that is integrally formed or removably attached, wherein the seal is configured to have a surface that contacts a user's face, thereby providing a substantially air-tight connection.

Respiratory Mask:

FIG. 1A shows a respiratory mask 100 that incorporates a removable ball jointed elbow and other mask components. The respiratory mask 100 comprises a cushion module 110, a mask frame 120, an elbow 130, a socket insert 140, headgear 150, a swivel 160 and a forehead piece 170.

Figure 1B:
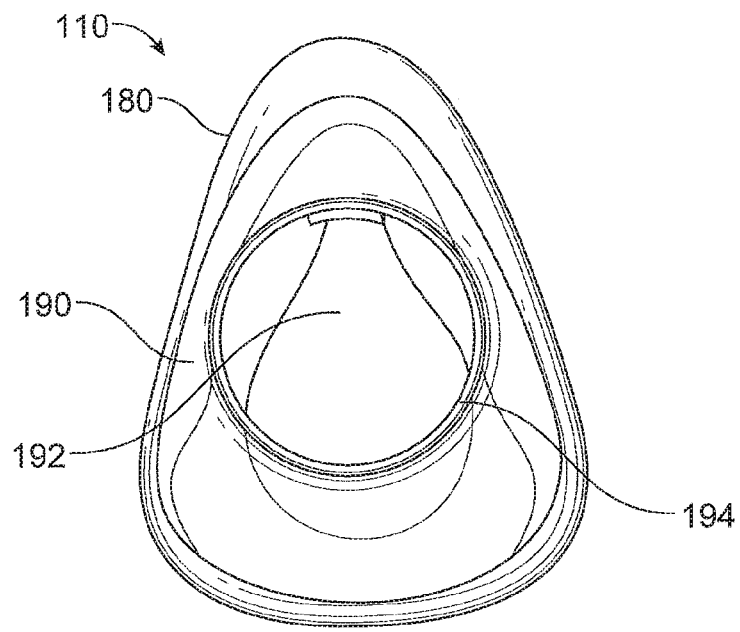
FIG. 1B is a front view of the cushion module of the present disclosure.

The cushion module 110 is configured to substantially surround a user's nose and/or mouth (when in use). The cushion module 110 comprises a seal 180 and a seal housing 190, wherein the seal 180 is configured to contact the user's face and to form a substantially airtight seal. In the illustrated arrangement, the seal 180 is over-moulded to the seal housing 190. The seal housing 190 comprises a substantially enclosed breathing chamber 192 and an annular opening 194 as shown in FIG. 1B. The annular opening 194 is configured to receive and connect to the socket insert 140 and to allow a flow of air to pass into the breathing chamber 192. In other embodiments, the annular opening 194 may be replaced with an opening of any other appropriate geometry.

Figure 2A:
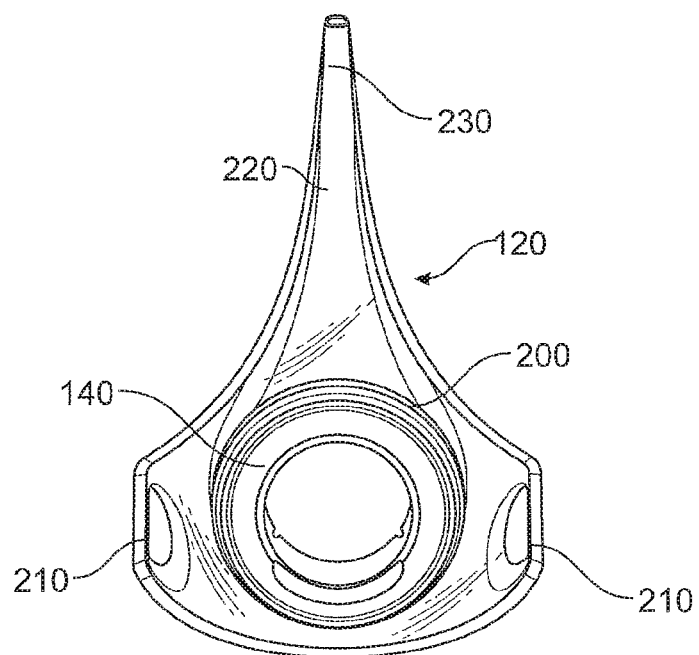
FIG. 2A is a front view of the mask frame of the present disclosure.

Mask Frame:

As shown in FIG. 2A, the mask frame 120 comprises a socket connection opening 200, headgear connectors 210, a bridge portion 220 and a male forehead piece connector 230. The socket insert 140 is configured to be insertable into the socket connection opening 200. In some configurations, the socket insert 140 is configured to be permanently connected to the socket connection opening 200. The socket insert 140 provides a socket for the elbow 130 (see e.g., FIG. 1A), such that the socket connection opening 200 and the elbow 130 provide a path through which air is supplied to the breathing chamber 192 (shown in FIGS. 1A and 1B).

The headgear connectors provide means for the headgear 150 to be connected to the mask frame 120 (as shown in FIG. 1A) such that a retaining and sealing force can be applied to the mask 100. The mask frame 120 has a relatively triangular shape, wherein the headgear connectors form two lower points (when worn and the user is sitting in an upright position) and the male forehead piece connector 230 forms the third upper point. The edges of the mask frame 120 that extend from the headgear connectors 210 to the male forehead piece connector 230 have a concave curve that narrows the frame 120 to form an elongate bridge portion 220. The bridge portion 220 is configured to pass over the user's nose. At the upper end, the bridge portion 220 is narrower than the user's nasal bridge such that interference with the user's line of sight is minimized.

Figure 2B:
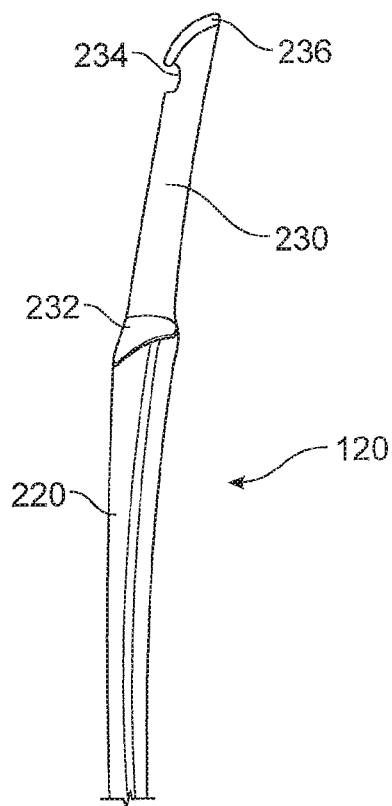
FIG. 2B is a close up side view of the male forehead piece connector.

As shown in FIG. 2B, the bridge portion 220 is terminated at the upper end by the male forehead piece connector 230. The male forehead piece connector 230 comprises a step 232 and a notch 234. The step 232 is provided at the transition between the bridge portion 220 and the male forehead piece connector 230. At this location, there is a step down in the geometry of bridge portion such that the male forehead piece connector is narrower and thinner but follows substantially the same lines as the bridge portion. This allows the male forehead piece connector 230 to fit inside a corresponding female geometry in the forehead piece 170 (see e.g., FIGS. 1A and 6A-E). The male forehead piece connector also includes a notch 234, which is located proximal to an upper end 236 of the mask frame 120. The notch is configured to provide a snap fit connection with corresponding geometry in the forehead piece 170.

Figure 3A:
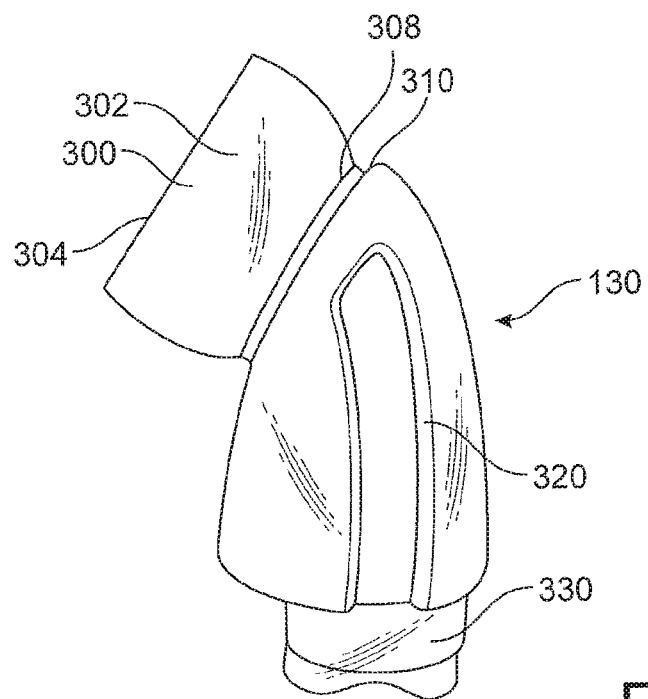
FIG. 3A is a side view of a prior art elbow.
Figure 3B:
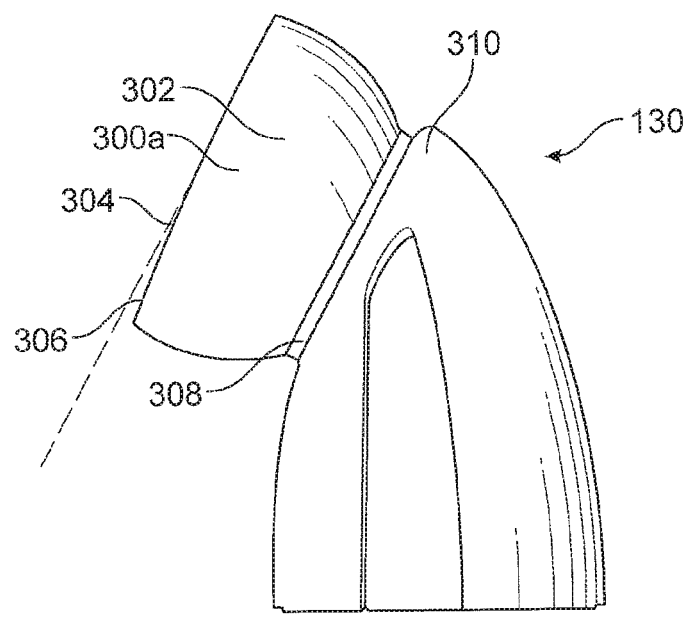
FIG. 3B is a side view of an alternative elbow of the present disclosure.
Figure 4A:
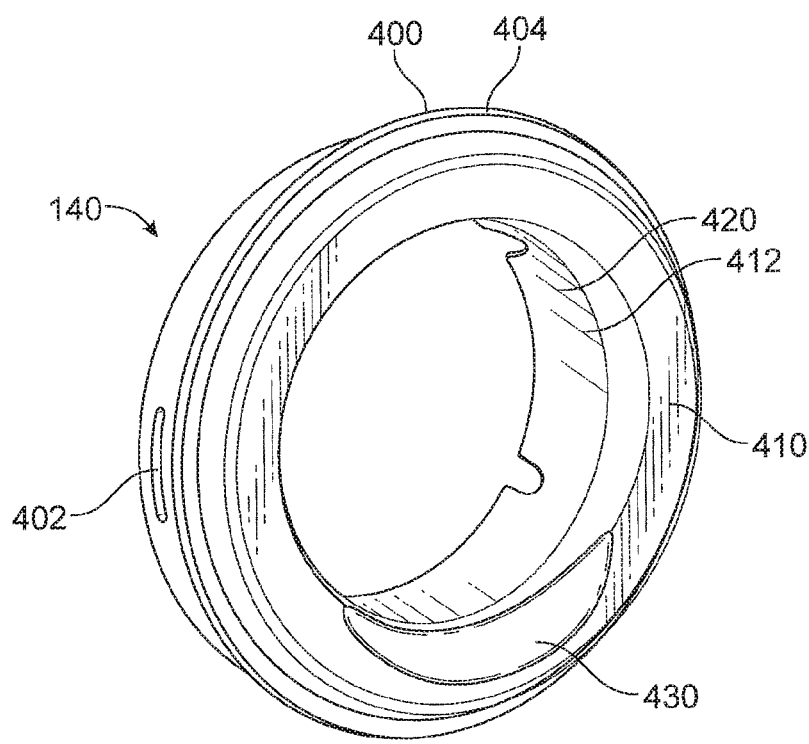
FIGS. 4A to 4E show various views of the socket insert of the present disclosure.
Figure 4B:
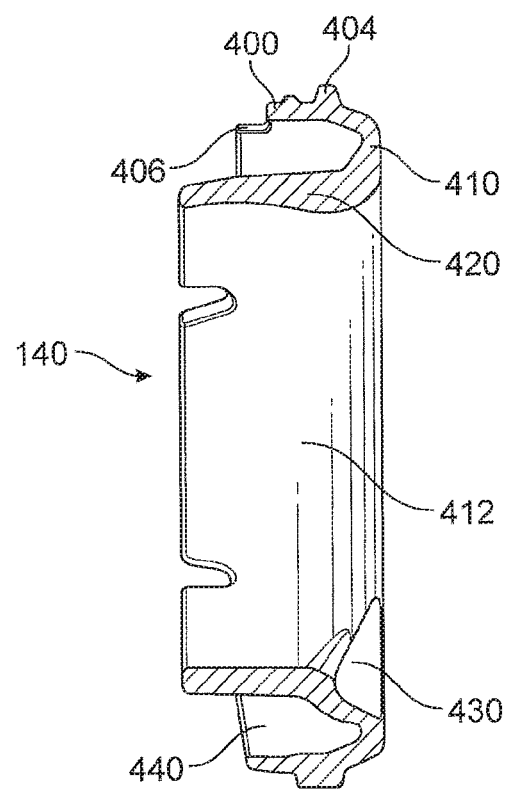
Figure 4C:
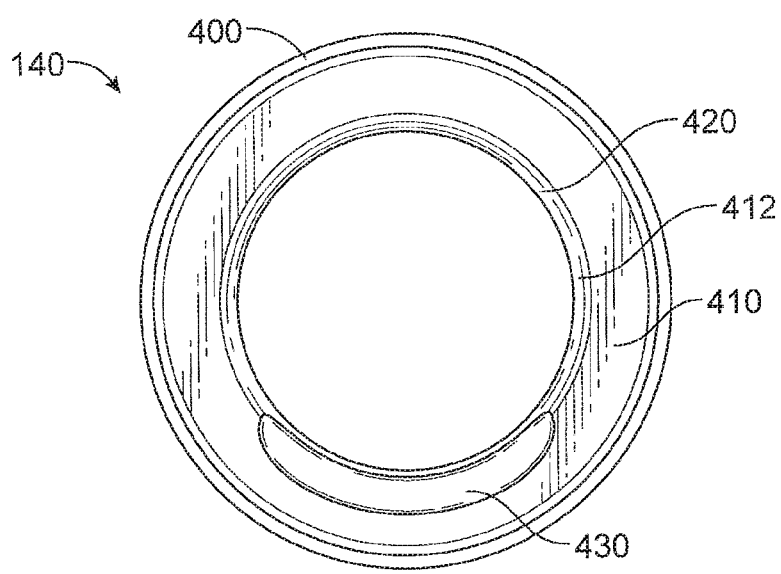
Figure 4D:
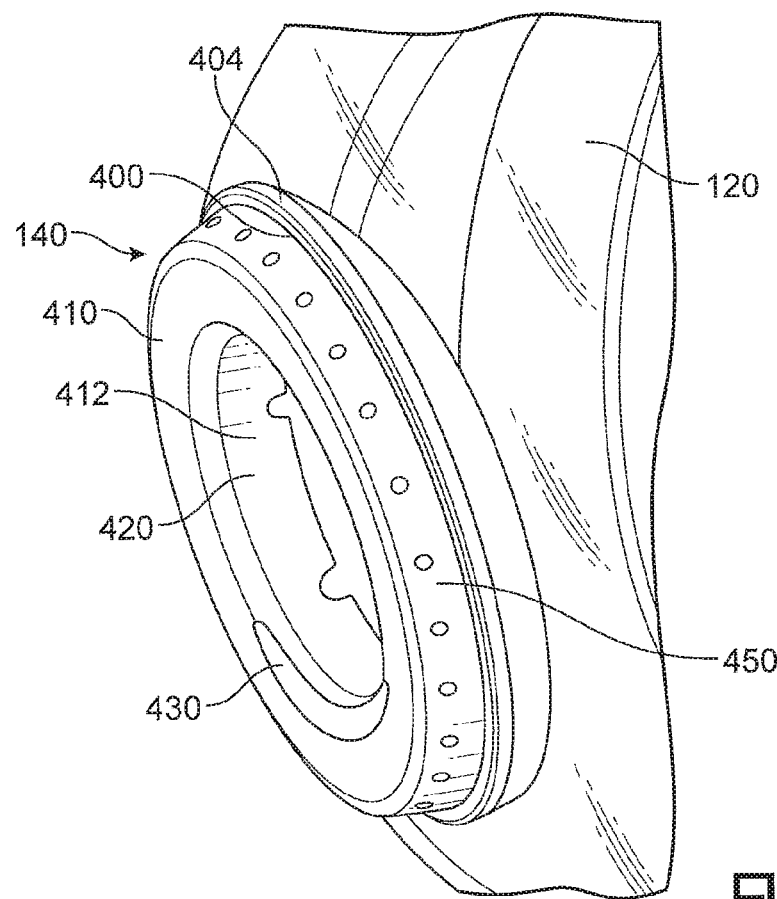
Figure 4E:
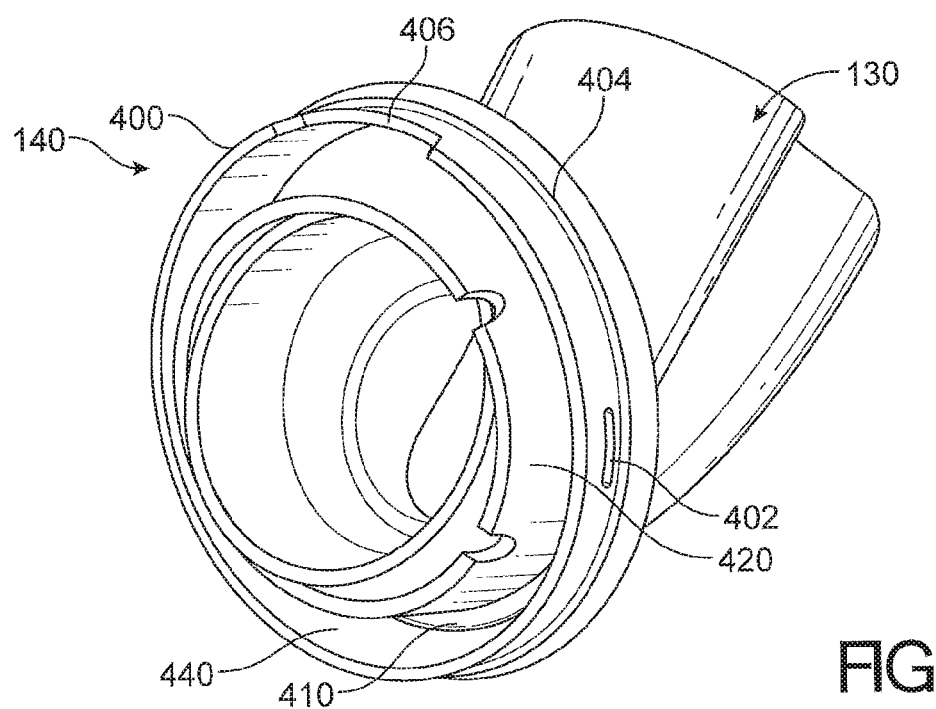

Elbow:

FIG. 3A shows a prior elbow 130, which comprises a ball joint 300, a lip 310, an elbow body 320 and a swivel connection 330. The ball joint 300 comprises a spherical elbow bearing surface 302 and a rear opening edge 304. In an embodiment of the present disclosure, as shown in FIG. 3B, the ball joint 300A can also comprise a tapered chamfer 306. The tapered chamfer 306 is positioned on a lower portion of the rear opening edge 304 and results in a non-planar edge that is angled relative to the rear opening edge 304 toward the lip 310. The ball joint 300A is configured to provide a substantially freely rotating connection between the elbow 130 and the socket insert 140. The ball joint 300A is connected to the elbow body 320 via a cylindrical cuff 308 and the lip 310. The lip 310 comprises an edge that is formed by a surface that extends perpendicularly from the cylindrical cuff 308 and the geometry of the elbow body 320 and the lip 310 is generally at an upper portion of the elbow body 320. The lip 310 is configured to interact with the socket insert 140 during removal of the elbow 130 (see e.g., FIG. 5). The swivel connection 330 is positioned at the opposite end of the elbow 130 relative to the ball joint 300A. It is configured to connect to the swivel 160 (as shown in FIG. 1A).

In an alternative embodiment the ball joint 300A comprises a truncated ball. The ball joint comprises a ball 302 that creates a spherical bearing surface. The truncation axis is substantially planar and angled toward the cuff 308. The truncation axis creates an angled edge 304. The edge 304 is angled toward the lower portion of the cylindrical cuff and lower portion of the elbow. The angled edge 304 creates an angled ball such that the distance of the upper edge of the ball is greater than the lower edge of the ball.

Socket Insert:

FIGS. 4A to 4E show the socket insert 140 in more detail. The socket insert is an annular component that comprises an outer wall 400, a front wall 410, an inner wall 420, an elbow removal notch 430, a rear channel 440 and an annular array of bias-flow holes 450 (see e.g., FIG. 4D). Although a socket insert 140 is disclosed herein, other configurations can be integrated or unitarily-formed with the mask frame 120. The bias-flow holes 450 may comprise any suitable cross-sectional geometry, including but not limited to, circular or elliptical holes or slots, or slots comprising polygonal, chevron, 'U' and 'W' shapes, wherein the geometry may be symmetrical or asymmetrical. In other embodiments, the socket insert 140 may not include the bias-flow holes 450. The bias flow holes 450 may be incorporated in another component of the respiratory mask.

The socket insert 140 provides a socket bearing surface 412 that supports the ball joint 300A when inserted into the socket insert 140. This configuration provides a rotatable connection between the elbow 130 and the mask frame 120. The outer wall 400, the front wall 410 and the inner wall 420 are connected to form a substantially 'u' shaped rear channel 440, wherein the front wall 410 is substantially perpendicular to the outer wall 400 and the inner wall 420. The front wall 410 is configured to connect and support the outer wall 400 at a radial offset from the inner wall 420.

The outer wall 400 comprises one or more seal housing notches 402, a frame connection 404, and an alignment key 406. The seal housing notches 402 are configured to provide a snap fit connection between the socket insert 140 and the seal housing 190. The seal housing notches 402 comprise an indentation that forms the female component of the snap fit connection. The frame connection 404 comprises two annular ridges that form a permanent push fit connection with the corresponding geometry of the socket connection opening 200 (as shown in FIG. 2A). The alignment key 406 is located on the upper rear edge of the outer wall 400. It comprises a substantially trapezoidal cut-out that aligns with a corresponding tab on the annular opening 194 of the seal housing 190. The alignment key is configured to reduce or eliminate the likelihood of a misaligned connection between the seal housing 190 and the socket insert 140. In some embodiments, the permanent connection between the frame connection 404 and the socket connection opening 200 may be achieved via ultrasonic welding or other suitable methods.

The inner wall 420 comprises a socket bearing surface 412, wherein the socket bearing surface 412 is substantially spherical and configured to contact and retain the ball joint 300A of the elbow 130. The socket bearing surface 412 is configured to contact the elbow bearing surface 302, thereby forming a substantially airtight assembly. When the elbow 130 and the socket insert 140 are connected, the bearing surfaces 302, 412 are configured to allow rotational movement between the parts, whilst restricting translational movement between the front and rear of the mask.

Figure 5:
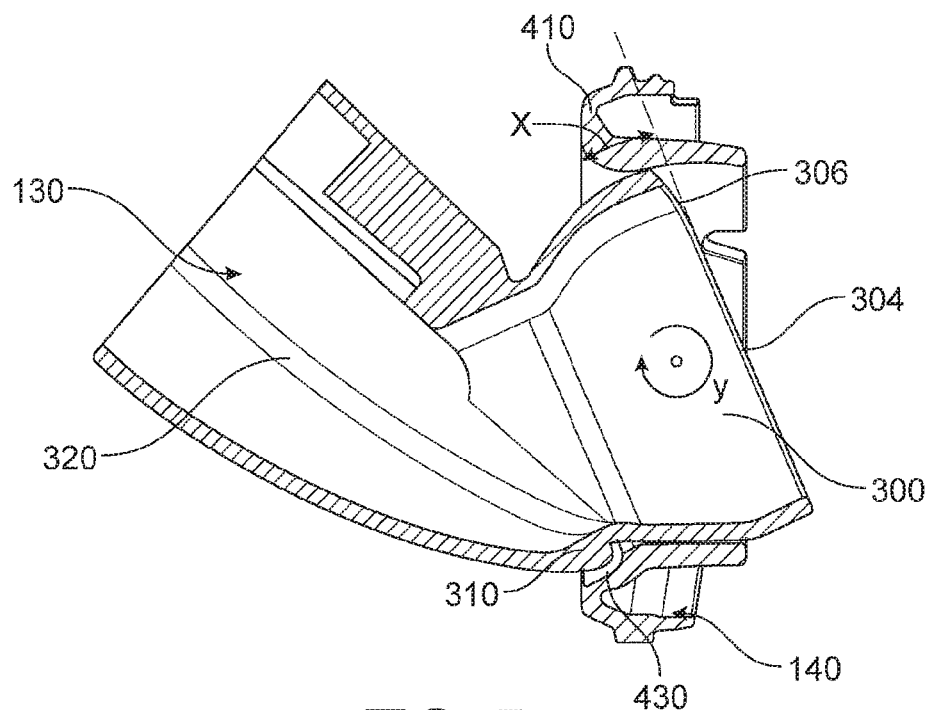
FIG. 5 is a cross-sectional view of the elbow and socket insert that shows the geometry that allows the elbow to be removed.

In the illustrated arrangement, the elbow removal notch 430 is positioned on a lower portion of the edge that is formed where the front wall 410 and the inner wall 420 intersect. The removal notch 430 comprises a scalloped portion, wherein the edge is cut away to form a tapered concave surface. The elbow removal notch is configured to substantially match the geometry of the lip 310 of the elbow 130 such that, when the elbow 130 is rotated to an upside down position, the lip 310 can sit within the elbow removal notch 430, as shown in FIG. 5. It is this configuration that allows the elbow 130 to be removed from the socket insert 140. In other embodiments, the elbow removal notch 430 may have a geometry that differs from the lip 310 geometry such that the two components can come into contact or can be located elsewhere circumferentially.

When the elbow 130 is rotated to an approximately inverted position, the lip 310 is approximately aligned with the removal notch 430. When the lip 310 is positioned in the elbow removal notch 430, the ball joint 300 is able to rotate further within the socket insert 140. This is a result of the surface of the elbow removal notch being offset rearward of the front wall. The extra rotation allows the lowest point (when mask is in use) of the rear opening edge 304 or tapered chamfer 306 to move closer to the front wall 410 (as shown by dimension x in FIG. 5) than would be possible without the elbow removal notch 430. This reduced distance, x, to the front wall 410 reduces the force required to move the rear opening edge 304 or tapered chamfer 306 beyond the front wall. The elbow removal notch 430 also forms a leverage point. The leverage point is formed by moving the center of rotation of the ball joint 300 from the location y (as shown in FIG. 5) to the point of contact between the lip 310 and the elbow removal notch 430. The geometry of the elbow removal notch allows a force to be applied through the lip 310 and new center of rotation, thus forming the leverage point. The leverage point is further away from the lowest point of the tapered chamfer 306 than the center of rotation y; this reduces the force required to move the rear opening edge 304 beyond the front wall 410.

Once at least a portion of the rear opening edge 304 is beyond the front wall 410, the ball joint 300 can be removed from the socket insert 140. It can be seen that the purpose of the tapered chamfer 306 is to further reduce the distance x that the ball joint 300 needs to be rotated in order to move the rear opening edge 304 beyond the front wall 410 and, thus, be removed from the socket insert 140 than when compared to a configuration without the tapered chamfer 306. In alternative embodiments (not shown), the elbow removal notch 430 may be replaced by a chamfered or scalloped section on the edge formed between the inner wall 420 and the front wall 410 of the socket insert 140. The chamfered edge can have the effect of reducing the distance x that the ball joint needs to rotate in order to be removed from the socket insert. In yet another alternative embodiment, the geometry of the elbow removal notch 430 may extend beyond the socket insert 140 and into the mask frame 120.

The alternative embodiment of an angled edge 304 for a truncated ball functions in a similar manner to that described with respect to FIG. 3B and FIG. 5. The angled truncation axis creates an angled rear opening edge 304 and creates a longer upper edge of the ball 302 as compared to the lower edge of the ball. The angled edge 304 allows the ball joint 300 to rotate further within the socket insert 140. This is a result of the lower edge of the ball being shorter than the upper edge of the ball. The extra rotation allows the lowest point (when mask is in use) of the rear opening edge 304 to move closer to the front wall 410. The extra rotation and the lowest point moving closer to the front wall 410 reduces the force required to move the rear opening edge 304 beyond the front wall. The elbow removal notch 430 also forms a leverage point as described. The leverage point is further away from the lowest point of the tapered chamfer 306 than the center of rotation; this reduces the force required to move the rear opening edge 304 beyond the front wall 410.

The elbow 130 and the socket insert 140 are generally configured such that the elbow 130 can only be removed from the socket insert 140 when oriented to a predetermined rotational position. As shown in FIG. 5, in the present embodiment, the elbow 130 can be removed when it is rotated to an upside down position, where the elbow body 320 is directed upwards towards the bridge portion 220 of the mask frame 120 (not shown). This reduces or eliminates the likelihood of unintentional detachment of the elbow during use. In other embodiments, the elbow 130 may be rotated to a different position for removal. Once removed, the elbow 130 can be reassembled to the socket insert 140 by reversing the removal actions and forces.

The single removal position and blended geometry of the elbow removal notch 430 dictate that the action of removing the elbow may not be obvious to all users, meaning that a user may need to be taught how to remove the elbow. This may be beneficial in some situations, as it may be desirable for only certain user groups to know how to remove the elbow. For instance, removal of the elbow for cleaning and sterilization is particularly important in environments where a single mask may be used for multiple users, such as in sleep labs; whereas it is not as important in home use environments where the mask has only a single user. Therefore, it may be desirable for doctors or sleep lab technicians to know how to remove the elbow, but not the direct user of the mask. In alternative embodiments, the geometry may be such that it is obvious how to remove the elbow.

Figure 6A:
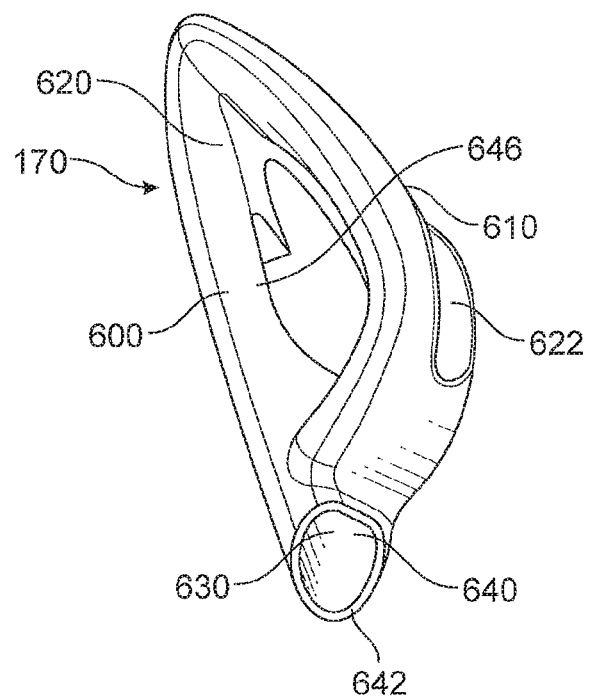
FIGS. 6A to 6E show various views of the forehead piece of the present disclosure.
Figure 6B:
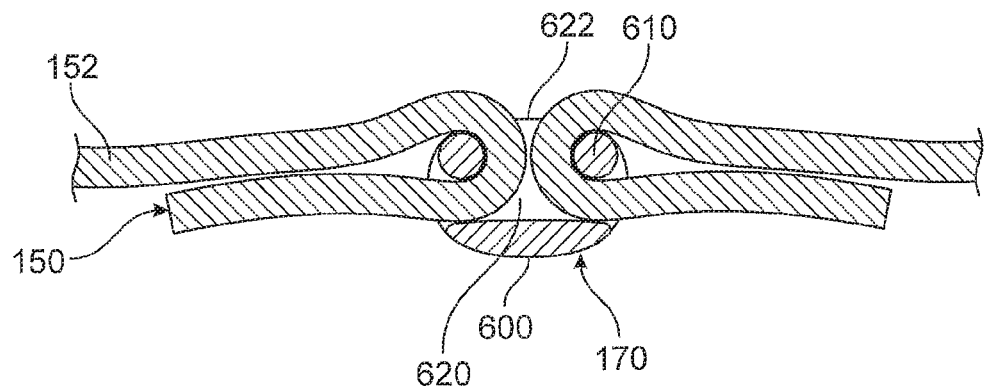
Figure 6C:
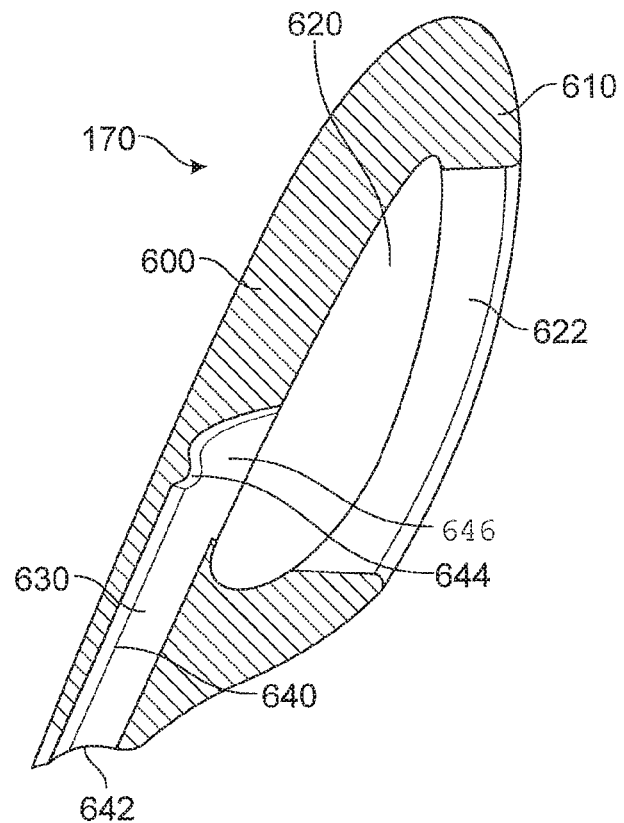

Forehead Piece:

As shown in FIG. 1A, the forehead piece 170 is a removable end cap configured to provide a connection between the mask frame 120 and the headgear 150. FIGS. 6A to 6E show that the forehead piece 170 comprises a front portion 600 and a rear portion 610, wherein the front and rear portions 600, 610 are connected to form a horizontal loop 620. The horizontal loop 620 provides a hole that extends horizontally (when the mask is in use) from one side of the forehead piece 170 to the other. The rear portion 610 comprises a rear opening 622. The rear opening 622 is configured to extend through the rear portion 610 in a direction that is substantially perpendicular to the front portion 600. The rear opening 622 in combination with the horizontal loop 620 are configured to provide a path through which the forehead straps 152 of the headgear 150 can pass. Both of the forehead straps 152 enter the forehead piece through the rear opening 622 and one forehead strap 152 exits from each side of the horizontal loop 620, as shown in FIG. 6B. In this configuration, the forehead piece forms a buckle through which the length of the forehead straps 152 can be adjusted.

Figure 6D:
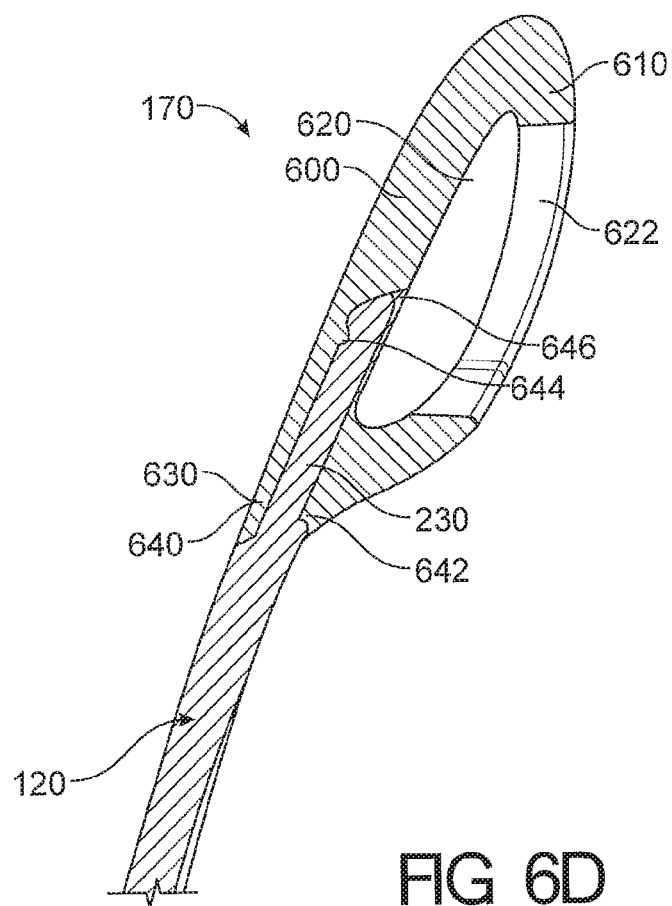

The front portion 600 comprises a female frame connector 630. The female frame connector 630 is configured to connect to the male forehead piece connector 230 of the mask frame 120 and comprises an internal cavity 640. The internal cavity 640 is shown in more detail in FIG. 6C. The internal cavity comprises a frame opening 642, a bump 644 and a moulding opening 646. The frame opening 642 is configured to pass over the male forehead piece connector 230. As shown in FIG. 6D, the geometry of the internal cavity 640 is configured to substantially match the geometry of the male forehead piece connector 230. The bump 644 comprises a raised lump that is configured to fit into the notch 234 of the male forehead piece connector 230. When the bump 644 and notch 234 are fitted together they, form a snap fit connection that enables the forehead piece 170 to be removably connected to the mask frame 120. The moulding opening 646 provides the internal cavity 640 with a second opening at the opposing end to the frame opening 642. The opening is substantially perpendicular to the front portion 600 and is located on the rear surface of the front portion 600. The moulding opening 646 is configured to provide a means for the mould tool to form the bump 644 on an internal surface of the internal cavity 640. The moulding opening 646 is configured to fit within the bounds of the rear opening 622, such that a single tooling component may form both the moulding opening 646 and the bump 644 as well as the rear opening 622.

Figure 6E:
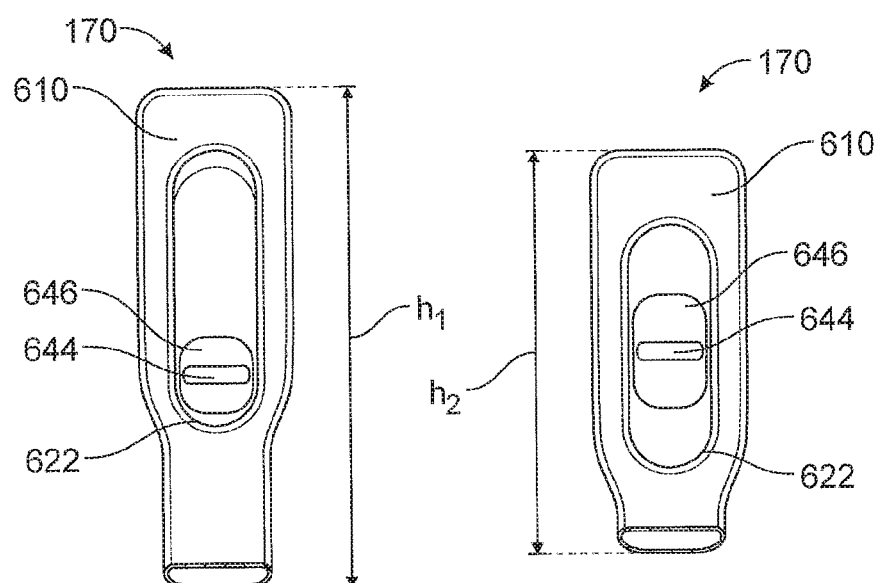

In some configurations, the forehead piece 170 is provided in two or more sizes, as shown in FIG. 6E. The different sizes can be provided by varying the height h of the forehead piece 170. The different sizes cater to a range of facial geometries in users. In the present embodiment, a medium/large and a small size are provided, wherein the small size has a height $h_2$ that is less than the height $h_1$ of the medium/large. The height of the forehead piece 170 determines the height at which the forehead straps of the headgear are connected to the mask 100 and, thus, how far up a user's forehead the straps will sit. The size of the forehead piece 170 can be selected to provide the most comfortable fit for a user. The horizontal loop 620 varies in size dependent on the height h of the forehead piece 170. The rear opening 622 has a fixed size that corresponds to the width of the forehead straps 152. The fixed size of the rear opening 622 restricts vertical movement of the forehead straps within the horizontal loop.

In other configurations, the forehead piece 170 and the mask frame 120 may be configured for a one time, permanent connection (e.g., a barbed or ramped protrusion and notch). Such a configuration allows for a common mask frame that is connectable to forehead pieces 170 of various shapes and sizes.

Headgear:

The headgear 150 is configured to apply retaining forces to the mask frame 120 such that the respiratory mask 100 is held in place on a user's face and a substantially airtight seal is achieved. The headgear 150 comprises a pair of forehead straps 152, a top or crown strap 154, a pair of lower or chin straps 156 and a rear headgear portion 158, as shown in FIG. 7A. In use, the forehead straps 152 are configured to extend forward from the rear headgear portion 158 and across the user's forehead to connect to the forehead piece 170, as previously described. The crown strap 154 is configured to form a link between the forehead straps 152, wherein the crown strap 154 extends across the top of the user's head. The chin straps 156 are configured to extend forward from the lower edge of the rear headgear portion 158, across the user's cheeks and chin, to the headgear connectors 210 of the mask frame 120. The chin straps 156 are connected to the headgear connectors 210 via separate headgear clips 700. The headgear clips 700 hook onto post components in the headgear connectors and provide a quick means for users to attach and detach the headgear 150 from the mask frame 120.

The length of the forehead straps 152 and chin straps 156 are secured by hook and loop fastener tabs 710 located at the ends of the straps. The tabs 710 comprise the hook component of hook and loop fastener material. The outer surface 720 is configured to have a surface finish that is suitable for the hook material to attach to. The forehead straps 152, the crown strap 154 and the chin straps 156 are made from a material, such as Breath-o-Prene™, which comprises layers of differing fabrics including textiles and foams. Breath-o-Prene™ is made from polyurethane foam with an outer layer of nylon and spandex. The materials are heat laminated together. Each of the straps can be made from a material with differing physical properties. For example, the crown strap 154 can be stretchable while the chin straps 156 are substantially non-stretch by comparison.

The rear headgear portion 158 comprises a spacer fabric pad 730 and a lower back strap 740. The spacer fabric pad 730 comprises a substantially rectangular portion with scalloped edges and the corners cut off. The cut off corners are configured to attach to the forehead straps 152 and the lower back strap 740. FIG. 7B shows that the spacer fabric pad 730 comprises two spacer fabric layers 732 layered one on top of the other. The spacer fabric layers have a right side 733 and a wrong side 734. The two layers are sewn together, inside out (i.e., with the wrong sides of the fabric facing out) to form a seam 736 near the raw edges 738 of the spacer fabric layers. Once sewn together the layers 732 are then turned right-side out, such that the right sides 733 are on the outside and the raw edges 738 are on the inside. The seam 736 extends around the perimeter of the spacer fabric pad 730 leaving the bottom edge 739 open. The open bottom edge 739 allows the spacer fabric pad 730 to be turned right-side out. Once turned right-side out, the forehead straps 152 and lower back strap 740 are attached to the spacer fabric pad 730. In the present embodiment, they are sewn together; however, other attachment methods, such as but not limited to welding may be appropriate. The open bottom edge 739 is sealed at the same time as being attached to the lower back strap 740.

The present headgear configuration incorporates the spacer fabric pad 730 in order to provide a light weight, breathable and cushioned region at the rear of the user's head. These qualities are desirable as they may improve the user's comfort when wearing the headgear. Spacer fabric has an untidy edge finish that tends to fray when cut. The present configuration of the spacer fabric pad 730 provides a tidy edge finish by hiding the raw edges on the inside of the pad. The seam 736 may also help to reduce or eliminate the likelihood of fraying.

The lower back strap 740 extends along the bottom edge 739 of the spacer fabric pad. The lower back strap 740 is made of a material that is less stretchy than the spacer fabric pad 730. The lower back strap 740 provides structural reinforcement to the spacer fabric pad 730 to reduce or eliminate the likelihood of excessive stretching that may cause the mask 100 to become displaced from a user's face during use.

Cushion Module:

As described above, the cushion module 110 is configured to substantially surround a user's nose and/or mouth and includes a seal 180 and a seal housing 190. The seal housing 190 provides a support structure of sorts for the respiratory mask assembly 100 in general and for the mask cushion or seal 180 more specifically. Although the respiratory mask 100 disclosed herein comprises a separable cushion module 110 and frame 120, in some configurations these components can be combined into a single structure. Accordingly, although described as a portion of the cushion module 110 herein, the seal 180 could also comprise a portion of a mask frame. Other suitable interface arrangements for defining a breathing chamber, supporting the seal and allowing connection of a breathing gases conduit and headgear (if desired) can also be used.

In some configurations, multiple cushion modules 110 are available for a given respiratory mask 100. For example, cushion modules 110 can vary from one another in size such that a suitable one of the available cushion modules 110 can be selected for a particular user. However, cushion modules 110 could vary relative to one another with respect to characteristics other than size in addition or in the alternative. FIGS. 8 and 9 illustrate a plurality of differently-sized cushion modules 110 that can be used as a component of the respiratory mask 100 disclosed herein. Each cushion module 110 is of substantially the same construction, with the exception of certain dimensions, some of which are discussed herein.

Cushion module 110A is relatively smaller in at least one dimension (e.g., seal height) than cushion modules 110B and 110C. Similarly, cushion module 110B is relatively smaller in at least one dimension (e.g., seal height) than cushion module 110C. Cushion modules 110A, 110B and 110C can be referred to as a size "small," "medium," and "large" modules, respectively. In some configurations, additional modules 110 can be provided, which can fall on either end of the illustrated modules 110A, 110B, 110C or could have at least one dimension that places the additional module(s) between the illustrated modules 110A, 110B, 110C in a relative sense. In some configurations, a lesser number (e.g., two) of cushion modules 110 are provided. As described herein, a reference to a general cushion module 110 can apply to any of the particular modules 110A, 110B, 110C. When discussing the modules 110A, 110B, 110C relative to one another, the specific reference numbers 110A, 110B, 110C generally are used. One or both of the seal 180 and the seal housing 190 can vary between the various size modules 110A, 110B, 110C. In the illustrated arrangement, both the seal 180 and the seal housing 190 vary in size between the various size modules 110A, 110B, 110C.

The seal housing 190 can be formed from any suitable material. In some configurations, the seal housing 190 is formed from a fairly rigid material. In some configurations, the seal housing 190 is formed from a plastic material, such as a polycarbonate material. In some configurations, the seal 180 is overmolded onto the seal housing 190 and, in some configurations, the seal 180 can be overmolded directly onto the seal housing 190, which can comprise chemical or mechanical overmolding, for example.

In some configurations, the seal housing 190 comprises a substantial portion of a forward wall of the cushion module 110. Such an arrangement provides an advantageous amount of support to the seal 180. For example, the seal housing 190 comprises a substantial portion of an oral portion of the forward wall of the cushion module 110. In the illustrated configuration, the seal housing 190 sweeps rearward from a central portion toward opposing side portions. The central portion contains the aperture or opening 194 for allowing a flow of supplied breathing gases to enter an interior of the cushion module 110. The opening 194 can allow the cushion module 110 to be assembled to the frame 120, the mask elbow 130 or another suitable structure. A width of the seal housing 190 can comprise a significant portion of the overall width of the oral portion of the cushion module 110, such as at least about three-quarters of the overall width of the oral portion of the mask assembly 100. Such an arrangement of the seal housing 190 can provide a desired amount of support to lateral portions of the seal 180. In some configurations, the seal housing 190 could be minimal, such as an annular support ring or frame, for example.

The seal 180 is designed to seal against the face of the user. The seal 180 preferably is formed of a soft material, such as silicone, for example but without limitation. In some configurations, at least portions of the seal 180 can be textured to improve comfort to the user. For example, in some configurations, at least portions of the mold used to form the illustrated seal 180 can be bead blasted to provide a surface texture in at least the regions of the seal 180 that will contact the skin of the user. Other techniques for texturing one or more surface of the seal 180 can be used. In some configurations, it may be desirable to avoid surface texturing and provide at least the face-contacting surfaces of the seal 180 with a smooth surface texture, which may increase grip of the seal 180 on the user's face and improve sealing characteristics.

As described above, the illustrated cushion module 110 comprises a nasal-oral or full face mask. Accordingly, with reference to FIGS. 10-15, the seal 180 comprises a nasal-oral mask seal and, therefore, comprises a combined oral-nasal opening 1000. In other configurations, the oral portion and nasal portion of the opening 1000 can be separate from one another. The opening 1000 preferably communicates with the breathing chamber 192 that is defined within the cushion module 110. As described above, the chamber 192 of the illustrated mask assembly 100 is at least partially defined by the seal housing 190 and the seal 180.

The illustrated seal 180 includes an upper portion 1002 and a lower portion 1004. The upper portion 1002 comprises a nasal portion of the opening 1000 that accommodates the user's nose. The lower portion 1004 comprises an oral portion of the opening 1000 that accommodates the user's mouth. Thus, the lower portion 1004 is significantly wider than the upper portion 1002. Together, on a proximal side of the cushion module 110, the upper portion 1002 and the lower portion 1004 combine to define a portion or an entirety of a face contacting surface 106. The face contacting surface 106 is configured to underlie a lower lip of the user, extend along the outside of the mouth, extend upward along the cheekbones and extend across the bridge of the nose of the user. Thus, the illustrated face contacting surface 106 defines a generally tear-drop shaped opening 1000. When the cushion module 110 is seated on the face of the user, the face contacting surface 106 will lie over the bridge of the nose, the cheekbones, the outside of the mouth and below the lower lip of the user. With a supply of positive pressure air, the seal 180 will balloon and seal against the face of the user to reduce or eliminate the likelihood of leakage between the face contacting surface 106 and the face of the user.

The illustrated seal 180 is a full face seal that is configured for similar applications and/or user preferences as the respiratory mask sold by the Applicant, Fisher & Paykel Healthcare, under the trademark Simplus®. While the Simplus® mask is a very successful full face respiratory mask product that provides excellent sealing characteristics and comfort for a wide variety of facial geometries, the illustrated seal 180 includes features or modifications relative to the Simplus® mask that provide improved performance for at least some applications or facial geometries. Thus, certain features of the present seal 180 are described in relation to the seal of the Simplus® mask.

Figure 11:
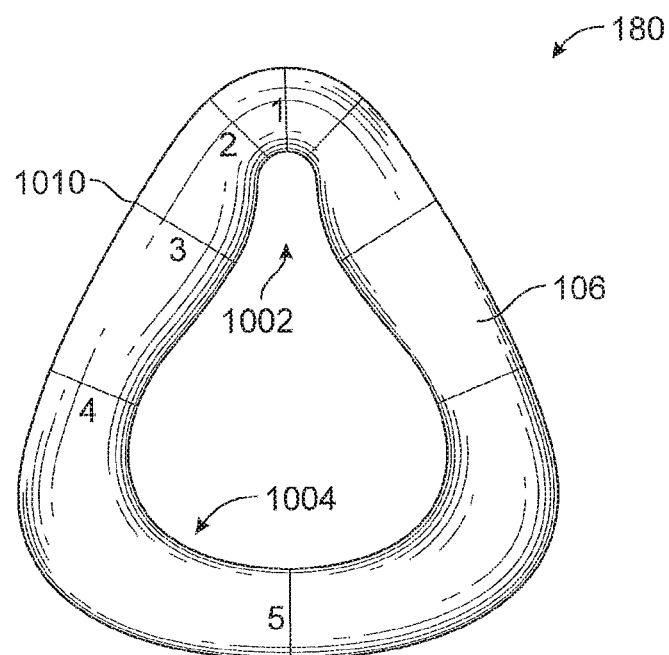
FIG. 11 is a plan view of the seal showing several sections.

With reference to FIG. 11, a plan view of the seal 180 illustrates width dimensions between an outer edge 1010 of the seal 180 and an inner edge that defines the opening 1000 along several sections of the seal 180, indicated as sections 1-5. At least sections 2-3 preferably are identical on each side of the seal 180. In some configurations, sections 2-4 can be identical on each side of the seal 180. Thus, in some configurations, the seal 180 can be symmetric about a central, vertical axis. Section 1 is a vertical line at the center top of the seal 180, which is coincident to the center line or lies within the mid-plane of the seal 180. Section 2 is a line that is 45 degrees to a vertical center line or mid-plane of the seal 180 and 90 degrees to the inner edge 1000 of the seal 180. Section 3 is a line at the widest part of the upper portion 1002 of the seal 180, which can be the widest part of the entire seal 180 in some configurations, that is, 90 degrees to the outer edge 1010 of the seal 180. Section 4 is the narrowest section of a lateral side of the lower portion 1004 of the seal 180 below Section 3 and that is 90 degrees to the outer edge 1010 of the seal 180. Section 5 is a vertical line at the center bottom of the seal 180. The table (Table 1) below lists exemplary dimensions of the sections for several sizes of the seal 180 in comparison with corresponding locations and sizes of the Simplus® seal. The listed dimensions for the seal 180 are exemplary dimensions and are not intended to be limiting unless otherwise indicated. In addition, the actual dimensions can vary within a range determined by normal manufacturing variations, which may be indicated herein by use of the terms "about," "approximately," or other similar terms. The dimensions illustrate widths of the various sections relative to one another and relative to the Simplus® seal.

TABLE 1

|  | Section 1 | Section 2 | Section 3 | Section 4 | Section 5 |
| --- | --- | --- | --- | --- | --- |
| Seal 180 Small | 15.1 mm | 15.2 mm | 20.9 mm | 17.5 mm | 15.8 mm |
| Simplus Small | 12.5 mm | 12.2 mm | 19.5 mm | 17.8 mm | 16.0 mm |
| Seal 180 Medium | 15.1 mm | 14.9 mm | 20.8 mm | 17.1 mm | 16.1 mm |
| Simplus Medium | 12.5 mm | 12.2 mm | 19.3 mm | 17.3 mm | 16.1 mm |
| Seal 180 Large | 15.1 mm | 14.7 mm | 20.9 mm | 17.3 mm | 16.8 mm |
| Simplus Large | 12.5 mm | 12.2 mm | 19.3 mm | 17.3 mm | 16.8 mm |

In general, Table 1 illustrates that, in the seal 180, sections 1 and 2 are relatively close in width. In some configurations, sections 1 and 2 can have the same width. Section 3 is larger than one or both of sections 1 and 2. In some configurations, sections 1 and 2 can be about 75% of the width of section 3. In some configurations, sections 1 and 2 are at least 70% of the width of section 3. Seal 180 has less variation in width in the upper portion 1002 or at least at sections 1, 2 and 3 relative to the Simplus® seal. In some configurations, as described below, sections 1 and 2 of the seal 180 have a larger width than comparable sections of the Simplus® seal, while section 3 of the seal 180 and the comparable section of the Simplus® seal are relatively similar in width.

One or both of sections 4 and 5 of the seal 180 have a width that is less than a width of one or more of sections 1-3. In the illustrated arrangement, both of sections 4 and 5 have a width that is less than a width of section 3. One or both of sections 4 and 5 of the seal 180 can have a width that is less than a width of one or more of sections 1-3. In the illustrated arrangement, both of sections 4 and 5 have a width that is greater than both of the widths of sections 1 and 2. The width of section 5 in the illustrated configuration is slightly greater, but similar to, the width of sections 1 and 2. The widths of sections 4 and 5 of the seal 180 are relatively similar to the widths at comparable locations of the Simplus® seal. In some cases, the widths of one or both of sections 4 and 5 are identical (e.g., size large) between the seal 180 and the Simplus® seal or the widths of seal 180 are slightly less than the widths of comparable sections of the Simplus® seal (e.g., size small). In size medium, the width of section 5 is identical, while the width of the seal 180 is slightly less than the width of the Simplus® seal at section 4.

Figure 12:
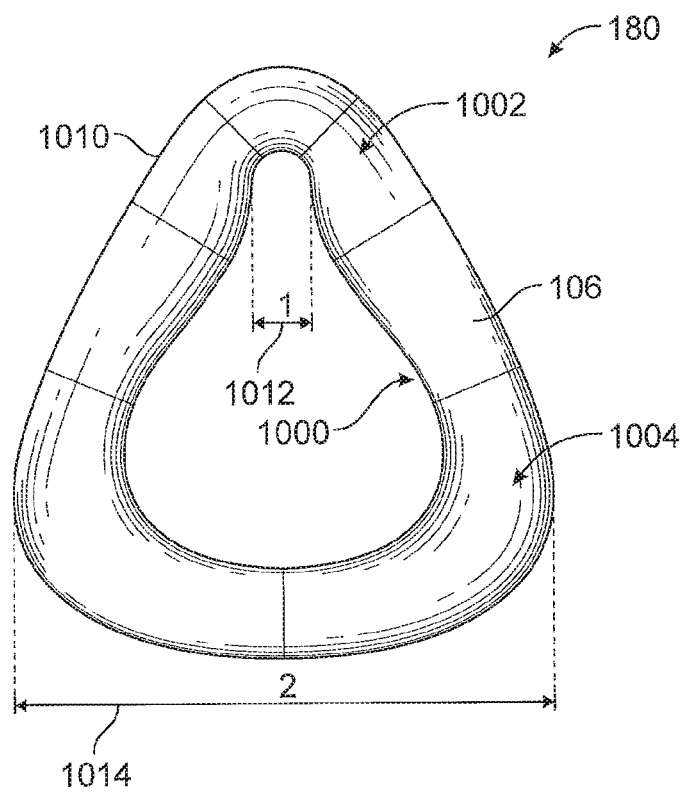
FIG. 12 is a plan view of the seal showing widths of two portions of the seal.

With reference to FIG. 12, a plan view of the seal 180 illustrates a first width 1012 of the opening 1000 defined between laterally opposite locations located on the opening 1000 within an upper portion 1002 of the seal 180 and a second width 1014 between laterally opposite locations located on the outer edge 1010 of the seal 180 within a lower portion 1004 of the seal 180. In particular, the illustrated first width 1012 is the width of the upper end portion of the opening 1000 within the upper portion 1002 of the seal 180 that accommodates the bridge of the user's nose. The width 1012 can be defined between relatively vertical sidewall portions of the upper end of the opening 1000 or between laterally opposite points at or near a point of inflection or undulation point at which each side of the edge defining the opening 1000 transitions between inward and outward curvature within the upper central portion of the upper portion 1002 of the seal 180. The width 1012 can be a width that contacts the bridge of the user's nose or determines or influences fit with the bridge of the user's nose. The width 1014 can be the maximum width of the face-contacting surface 106 within the lower portion 1004 of the seal 180, which can be the maximum width of the seal 180 in common seal arrangements. The width 1012 preferably is relatively small at least compared to the width 1014, which is useful as a reference point to compare the width 1012 relative to other seals. The table (Table 2) below lists exemplary dimensions of the widths 1012 and 1014 for several sizes of the seal 180 in comparison with corresponding locations and sizes of the Simplus® seal. The listed dimensions for the seal 180 are exemplary dimensions and are not intended to be limiting unless otherwise indicated. In addition, the actual dimensions can vary within a range determined by normal manufacturing variations, which may be indicated herein by use of the terms "about," "approximately," or other similar terms.

TABLE 2

| Seal | Width 1012 | Width 1014 | Ratio |
| --- | --- | --- | --- |
| Seal 180 Small | 11 mm | 95.7 mm | 0.1149 |
| Seal 180 Medium | 11 mm | 96.5 mm | 0.1140 |
| Seal 180 Large | 11 mm | 97.3 mm | 0.1131 |
| Simplus Small | 12.5 mm | 96.1 mm | 0.1301 |
| Simplus Medium | 12.5 mm | 96.5 mm | 0.1295 |
| Simplus Large | 12.5 mm | 96.9 mm | 0.1290 |

Table 2 illustrates that the width 1012 is less than about 12.5 percent, 12 percent or 11.5 percent of the width 1014 in all sizes of the seal 180. In some configurations, the width 1012 can be equal to about 12.5 percent or equal to about 12 percent of the width 1014 in one or more sizes of the seal 180. The width 1012 of the illustrated seal 180 can be equal to about 11.5 percent of the width 1014. The width 1012 of the illustrated seal 180 can be between about 11.3-11.5 percent of the width 1014 for one or more sizes of the seal 180. The absolute value of the width 1012 can be equal to or less than about 12 mm, equal to or less than about 11.5 mm or equal to or less than about 11 mm regardless of the width 1014. Such arrangements provide a desirable level of sealing for a variety of nasal sizes and geometries. In comparison, the widths of the Simplus® seal corresponding to width 1012 are 12.5 mm and about 12.9-13 percent of the width corresponding to width 1014.

Figure 10:
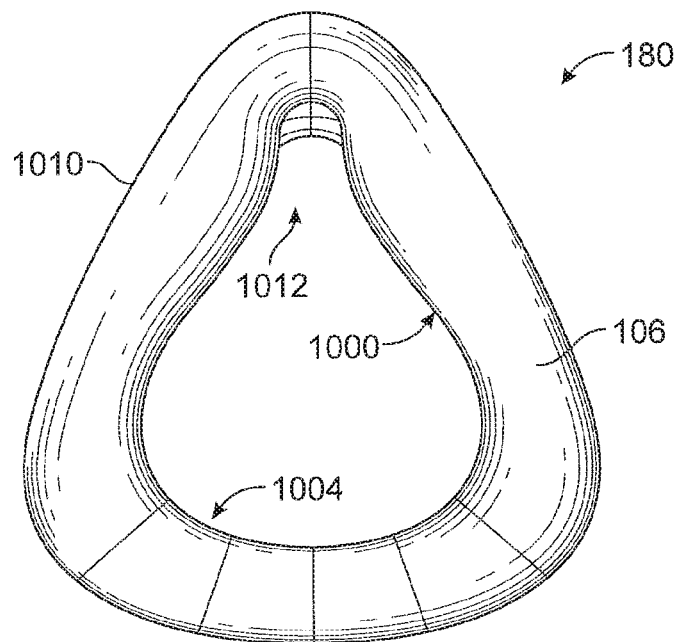
FIG. 10 is a plan view of a face contacting surface of a seal of one of the cushion modules of FIGS. 8A to 8C.
Figure 13:
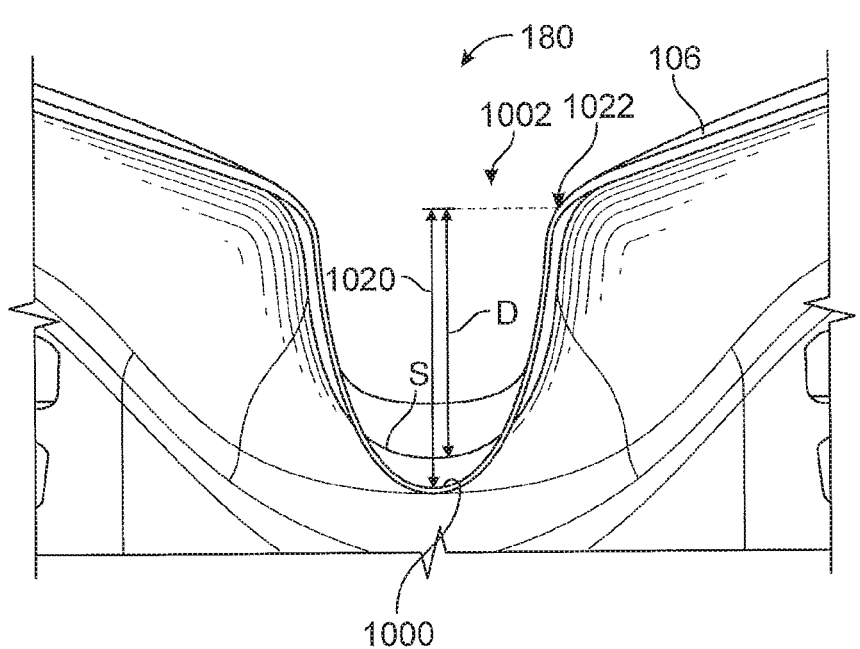
FIG. 13 is a bottom view of an upper portion of the seal and, in particular, a nose bridge portion.
Figure 14:
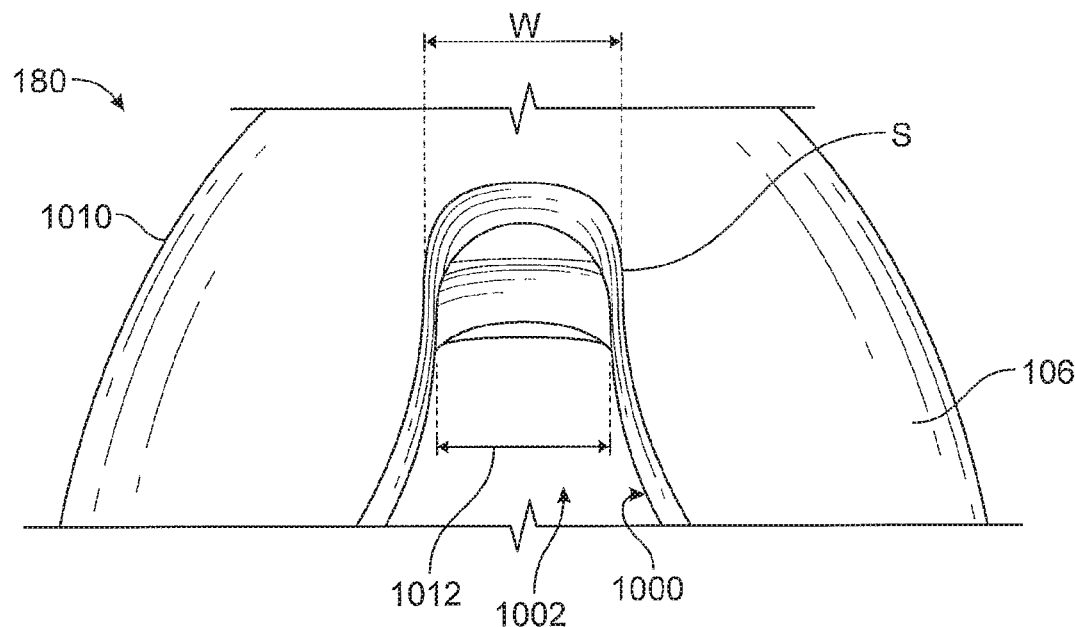
FIG. 14 is a view of the face contacting surface of the nose bridge portion of the seal.

With reference to FIGS. 10, 13 and 14, the upper portion 1002 of the opening 1000 of the illustrated seal 180 defines a substantially continuously curved, uppermost section at the center, top of the opening 1000. Preferably, the uppermost section of the opening 1000 defining the center, top of the opening 1000 does not include any linear portions or at least any linear portions of significant length relative to an overall length of an edge of the upper portion 1002 or relative to a width of the upper portion 1002. The rounded shape of the center, top of the opening 1000, which contacts the top of a user's nose, is believed to stretch to accommodate relatively square or sharp nasal geometries while also sealing well against smaller and/or rounder nasal geometries by reducing or eliminating gaps.

With reference to FIGS. 13 and 14, the seal 180 is illustrated with a corresponding edge S of the Simplus® seal included for the sake of comparison. As illustrated in FIG. 13, the seal 180 defines a depth 1020 from a transition point 1022 between the face contacting surface 106 or a rearward or proximal-most surface adjacent the inwardly-projecting, nasal bridge accommodating portion that defines the edge 1000 in the upper portion 1002. Preferably, the depth 1020 is greater than a corresponding depth D of the Simplus® seal. With reference to FIG. 14, the greater depth 1020 (compared to depth D) can be created by extending the inwardly-projecting, nasal bridge accommodating portion further inward/forward and/or downward relative to the Simplus® seal. That is, in the illustrated arrangement, the inwardly-projecting, nasal bridge accommodating portion of the seal 180 continues beyond a termination edge S of the Simplus® seal to extend further and deeper into the interior of the cushion module 110, which results in the seal 180 having a greater depth 1020 (than depth D) and a smaller width 1012 (than width W) relative to the Simplus® seal. As a result, the seal 180 has a greater contact area or at least the potential of a greater contact area with the bridge of the user's nose relative to the Simplus® seal.

Figure 15:
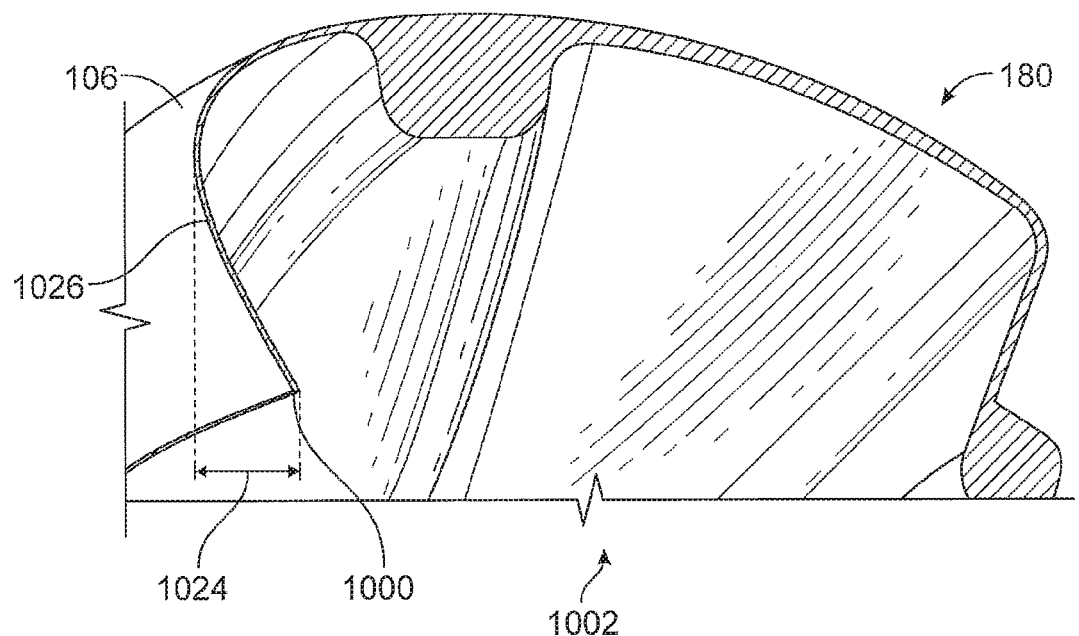
FIG. 15 is a sectional view of the upper portion of the seal.

FIG. 15 illustrates the upper, center portion of the seal 180 sectioned through the center or along the mid-plane of the seal 180 in a forward-rearward direction. The seal 180 defines a depth 1024 between a rearward-most point 1026 and a terminal edge 1000 along the center or mid-plane of the seal 180. The depth 1024 can be about 4.26 mm in one or more sizes or configurations of the seal 180. Preferably, the depth 1024 is equal to greater than about 3.5 mm, 3.75 mm, 4 mm or about 4.25 mm. In some configurations, the depth 1024 is equal to or less than about 6 mm or equal to or less than about 5 mm. For the sake of comparison, a corresponding depth of the Simplus® seal is about 2.75 mm. As described above, the greater depth 1024 of the seal 180 allows the nasal bridge accommodating portion to contact or potentially contact the bridge of the user's nose to improve the seal for at least some nasal geometries.

The illustrated seal 180 of the cushion module 110 comprises a fairly complex range and configuration of thicknesses, as shown in FIGS. 16-20. The thicknesses are varied to take advantage of or provide different characteristics in different regions of the illustrated seal 180. For example, the thicknesses in the various regions can be selected to address a desired characteristic for that region and/or the seal 180 as a whole. Such characteristics can include, for example, allowing the seal 180 to conform to the facial geometry of the user to enhance sealing properties or comfort, supporting the shape of the mask seal without significant internal gas pressure to facilitate fitment and/or in response to internal gas pressure and/or external pressure (e.g., caused by headgear forces) or providing strength or durability.

Figure 16:
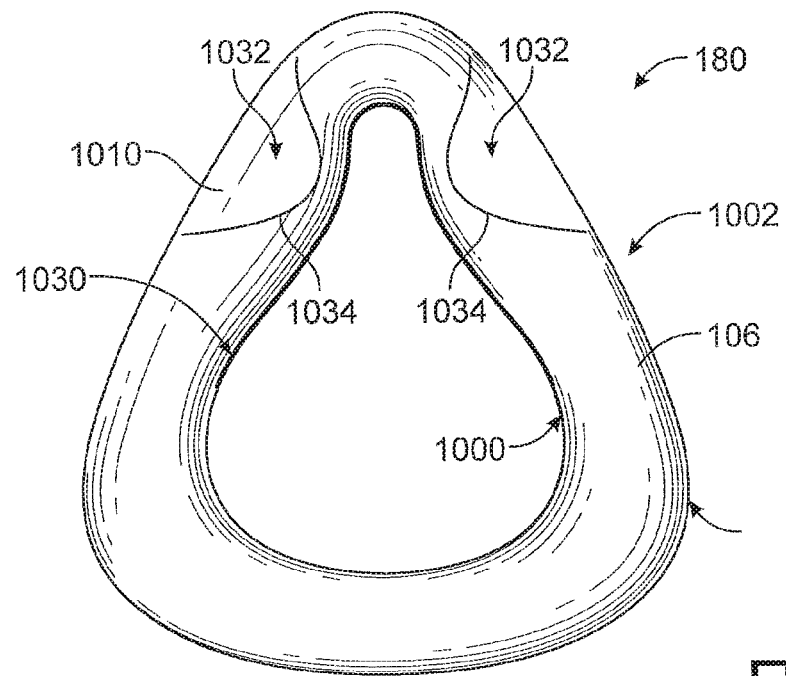
FIG. 16 is a plan view of a face contacting surface of a seal of one of the cushion modules of FIGS. 8A to 8C illustrating regions having varied thicknesses.

With reference to FIG. 16, in some configurations, the seal 180 includes a continuous thin internal edge section 1030 of at least a portion of the edge that defines opening 1000 in the upper portion 1002 of the seal 180. That is, the thin internal edge section 1030 is a portion of the edge that defines opening 1000 that defines a thickness that is equal to or less than a certain thickness, as described below, along a continuous length of the edge that defines opening 1000. Preferably, the continuous thin internal edge section 1030 extends at least along the top center portion of the edge that defines opening 1000 and along the portions of the edge that contact the bridge of and laterally alongside the user's nose. In some configurations, the continuous thin internal edge section 1030 extends into the lower portion 1004 of the seal 180. In some configurations, the continuous thin internal edge section 1030 extends along at least the entire upper half of the seal 180. In some configurations, the continuous thin internal edge section 1030 extends along approximately the upper two-thirds or at least about the upper two-thirds of the seal 180. In some configurations, the continuous thin internal edge section 1030 extends inwardly from the edge that defines opening 1000 at least about 0.5 mm to about 1 mm. In some configurations, the thin edge sections 1030 can extend further inwardly from the edge that defines opening 1000; however, it can be desirable for further inward portions of the seal 180 to have greater thicknesses. In some configurations, the thin edge section 1030 has a thickness that is equal to or less than about 0.6 mm or equal to or less than about 0.4 mm. The continuous thin internal edge section 1030 can vary in thickness in a direction extending inwardly from the edge that defines opening 1000 or along its length within these desired thickness ranges.

In some configurations, the seal 180 also or alternatively includes thickened nose pads 1032. The thickened nose pads 1032 preferably are positioned on each lateral side of the upper portion 1002 of the opening 1000. Preferably, the thickened nose pads 1032 extend along at least a portion of the face contacting surface 106 of the seal 180 but do not extend in a lateral direction all the way to the edge that defines the opening 1000. That is, innermost edges of the nose pads 1032 terminate prior to the edge that defines the opening 1000. In some configurations, the thickened nose pads 1032 are created by thickened regions of the seal 180 wherein the additional material extends inwardly into the interior of the cushion module 110. The thickened nose pads 1032 can have laterally inward edges 1034 that are curved (e.g., U-shaped) with centers of the curved portions being positioned closer to the opening 1000 than upper and lower portions of the curved edge 1034.

Figure 17:
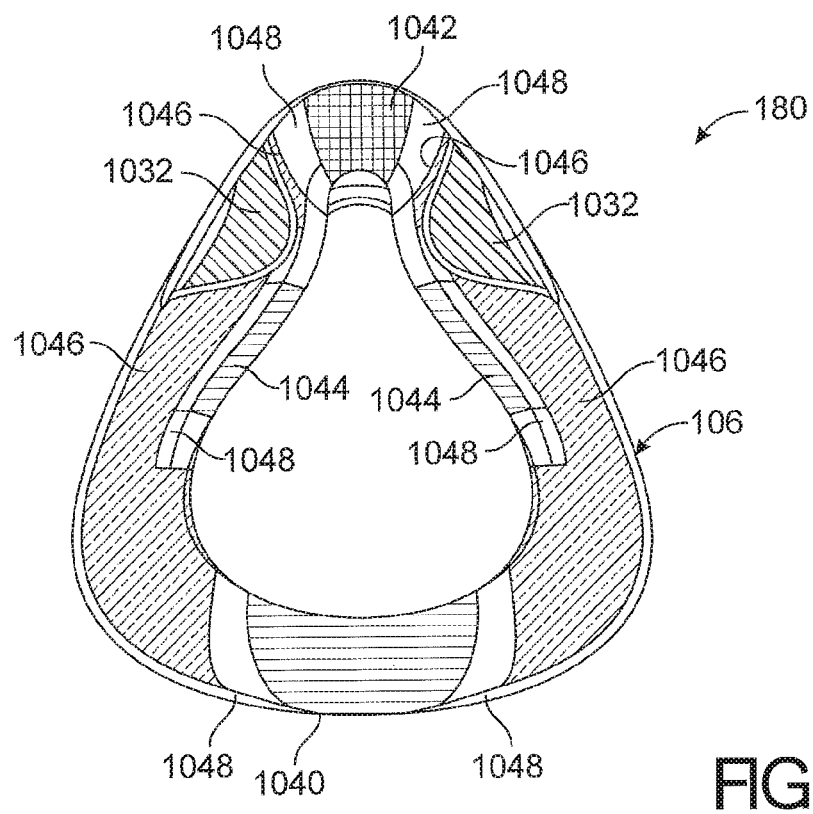
FIG. 17 is a plan view of a face contacting surface of a seal of one of the cushion modules of FIGS. 8A to 8C illustrating additional varied thickness regions relative to FIG. 16.

FIG. 17 illustrates differences in thicknesses of the seal 180 in various regions or portions. The regions and portions are indicated in FIG. 17. Typically, the outer surface of the seal 180 is of a substantially smoothly curved shape with variations in thickness being accomplished by inwardly-extending portions of the inner surface of the seal 180, as apparent, for example, in FIGS. 18 and 22. The seal 180 can include one or more of the regions or portions described herein.

The illustrated seal 180 comprises a bottom or chin region 1040. The chin region 1040 in the illustrated seal 180 extends along at least a portion of the opening 1000. Preferably, the chin region 1040 extends along at least a lower, central portion of the opening 1000 that is positioned below the lower lip of the user on or near the user's chin. The chin region 1040 can extend along an entirety or a substantial entirety of a height of the lower section of the face contacting surface 106 of the seal 180. In other words, the chin region 1040 can extend from a lower end of the outer edge 1010 to a lower end of the edge that defines the opening 1000. The chin region 1040 can extend along a substantial portion of a width of the seal 180, such as at least about one-half or more of a maximum width of the opening 1000. The illustrated chin region 1040 is centered in a lateral direction of the seal 180.

The chin region 1040 can be a relatively soft region that contacts the area below the lower lip of the user and can allow the seal 180 to accommodate a range of chin geometries. Accordingly, the chin region 1040 can have a thinner cross-section than other regions of the seal 180. In some configurations, the chin region 1040 has the smallest thickness of the seal 180, which may be equal to a thickness of other regions. For example, a portion or an entirety of the chin region 1040 can have a thickness of about 0.3 mm. In some configurations, the thickness of the chin region 1040 can be less than 0.3 mm. For example, the thickness could be as low as about 0.15 mm.

The seal 180 can also include a top or nasal bridge region 1042 located at the top center of the seal 180 and extending along the top of the opening 1000. Similar to the chin region 1040, the nasal bridge region 1042 can extend along an entirety or a substantial entirety of a height of the top section of the face contacting surface 106 of the seal 180. The nasal bridge region 1042 can extend in a lateral direction a distance about equal to the width 1012 (FIG. 12). In the illustrated arrangement, the nasal bridge region 1042 has a generally inverted trapezoidal shape, with the longer edge being located above the shorter edge. However, in other configurations, the nasal bridge region 1042 could have other shapes.

Given a desire to gently seal against the bridge of the nose, the nasal bridge region 1042 in the illustrated configuration has a fairly small thickness. In some configurations, the nasal bridge region 1042 has the smallest thickness of the seal 180, which can be equal to the thickness of other portions of the seal 180. For example, a portion or an entirety of the nasal bridge region 1042 can have a thickness that is equal to the thickness of the chin region 1040. In some configurations, the thickness of a portion or an entirety of the nasal bridge region 1042 is about 0.3 mm. In some configurations, the thickness of the entirety the nasal bridge region 1042 is about 0.3 mm. In some configurations, the thickness of the nasal bridge region 1042 can be less than 0.3 mm. For example, the thickness could be as low as about 0.15 mm. However, it has been determined that lower thicknesses can result in or increase the likelihood of creasing of the nasal bridge region 1042 for some facial geometries and/or under some operational gas pressures. Keeping the thickness at or above about 0.3 mm in a substantial portion or an entirety of the nasal bridge region 1042 can reduce the incidence of creasing over a substantial range of operational pressures, which may comprise an entire range of normal operating pressures.

The illustrated seal 180 also includes lateral portions 1044 located along or adjacent to lateral sides of the opening 1000. In the illustrated arrangement, the lateral portions 1044 are elongate strips that extend along vertical center portions of each lateral side of the opening 1000. The lateral portions 1044 extend generally from an upper end of the lower portion 1004 of the seal 180 to a lower end of the upper portion 1002 of the seal 180. The lateral portions 1044 can be located on the seal 180 to extend along the user's cheeks beside the user's nose.

Preferably, to conform to a wide variety of facial geometries and maintain a seal in the present of creases, lines or wrinkles that may be present on the user's cheeks and/or caused by facial movements (e.g., smiling), the lateral portions 1044 preferably have a relatively low thickness. For example, in some configurations, the lateral portions 1044 have the smallest thickness of the seal 180, which can be equal to the thickness of other portions of the seal 180. For example, a portion or an entirety of each of the lateral portions 1044 can have a thickness that is equal to the thickness of one or both of the chin region 1040 and the nasal bridge region 1042. In some configurations, the thickness of a portion or an entirety of each of the lateral portions 1044 is about 0.3 mm. In some configurations, the thickness of the entireties of the lateral portions 1044 is about 0.3 mm. In some configurations, the thickness of a portion or an entirety of each of the lateral portions 1044 can be less than 0.3 mm. For example, the thickness could be as low as about 0.15 mm.

The illustrated seal 180 includes outer peripheral portions 1046 that extend along lateral portions of an outer periphery of the seal 180. To reduce the incidence of wrinkling of at least some of the face contacting regions of the seal 180 during use, it has been found that the outer peripheral portions 1046 of the seal 180 should be fairly rigid. In the illustrated arrangement, the outer peripheral portions 1046 extend along the generally vertically extending, laterally outward portions of the face contacting surface 106 of the seal 180.

In the illustrated arrangement, the outer peripheral portions 1046 extend along a substantial portion of a height of the lower portion 1004 of the opening 1000 each lateral side of the opening 1000. In some configurations, the outer peripheral portions 1046 extend along an entire height of the lower portion 1004 of the opening 1000. Upper ends of the outer peripheral portions 1046 can extend at least to about a vertical location at which the opening 1000 narrows significantly to form the upper portion 1002 that accommodates a bridge of the user's nose. Lower ends of the outer peripheral portions 1046 can extend toward, to or below a lower end of the opening 1000. The chin region 1040 can be positioned between lower ends of the outer peripheral portions 1046. Each of the outer peripheral portions 1046 and the chin region 1040 can define a portion of a lower edge of the opening 1000.

In the illustrated arrangement, upper portions of the outer peripheral portions 1046 are spaced outwardly from the edge that defines the opening 1000. In some configurations, the outward spacing of the upper portions of the outer peripheral portions 1046 accommodates the lateral portions 1044 between the opening 1000 and the upper portions of the outer peripheral portions 1046. In some configurations, lower portions of the outer peripheral portions 1046 extend close to the opening 1000 compared to upper portions of the outer peripheral portions 1046. In the illustrated configuration, lower portions of the outer peripheral portions 1046 extend substantially to or to the edge that defines the opening 1000.

The relatively increased thickness of the outer peripheral portions 1046 can assist in resisting or preventing collapse of the seal 180 in the absence of significant internal gas pressure to facilitate fitment and provide feedback to the user, such as in response to applied forces (e.g., headgear forces). The outer peripheral portions 1046 can help maintain the curved shape of the lateral sides of the seal 180 and/or help maintain a separation between a rear wall of the seal 180 (defining the face contacting surface 106) and a front end or wall of the seal 180, seal housing 190 or other structure immediately forward of the face contacting surface 106. In some configurations, the thickness of a portion or an entirety of the outer peripheral portions can be between about 1.0 mm and about 2.0 mm. In the illustrated configuration, a portion or an entirety of the outer peripheral portions 1046 preferably have a thickness of about 1.5 mm. The thicknesses of the outer peripheral portions 1046 can be consistent or varied.

As described above, the seal 180 can include thickened nose pads 1032. The thickened nose pads 1032 preferably are positioned on each lateral side of the upper portion 1002 of the opening 1000. In the illustrated configuration, the nose pads 1032 intersect the outer peripheral portions 1046, such that a portion of the outer peripheral portions 1046 is located both above and below the nose pads 1032. Preferably, the thickened nose pads 1032 extend along at least a portion of the face contacting surface 106 of the seal 180 but do not extend all the way to the edge that defines the opening 1000. That is, a laterally inward edge 1034 of each of the nose pads 1032 terminates prior to the edge that defines the opening 1000. Laterally outward edges of the nose pads 1032 can extend substantially to or to the outer edge 1010 of the face contacting surface 106 of the seal 180. The laterally inward edges 1034 can be curved with centers of the curved portions being positioned closer to the opening 1000 than upper and lower portions of the curved edge 1034. In other words, the curved edges 1034 can be generally U-shaped with the bottom of the U-shape being positioned closer to the opening 1000 and the top of the U-shape being positioned further from the opening 1000.

Figure 18:
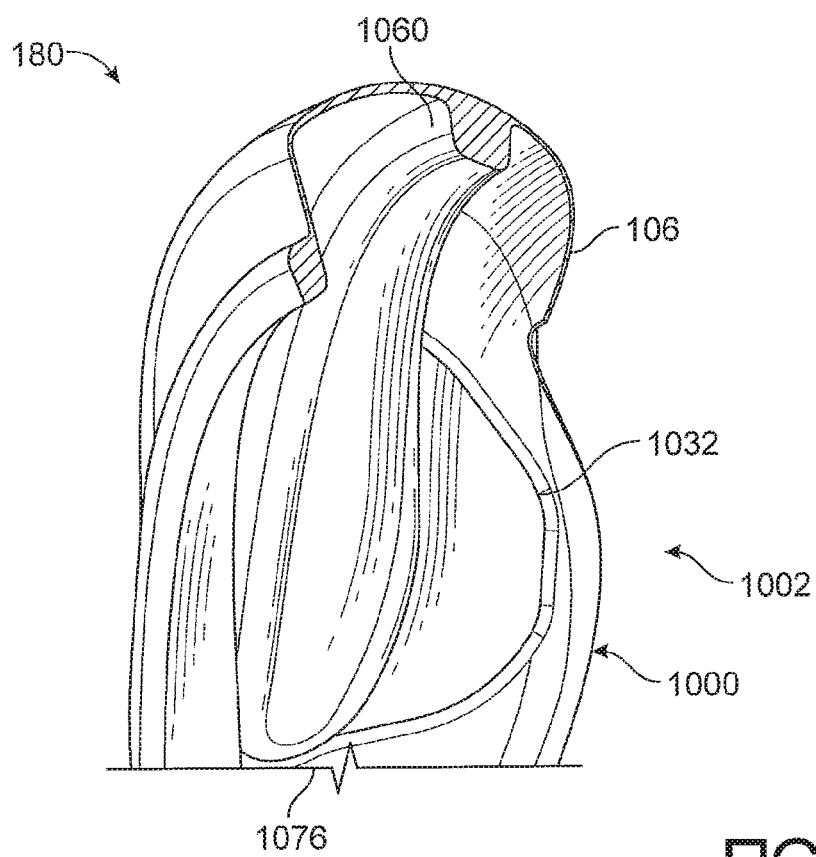
FIG. 18 is a perspective view of an interior of a sectioned upper portion of a seal.

With reference to FIG. 18, in some configurations, the thickened nose pads 1032 are created by thickened regions of the seal 180, wherein the additional material extends inwardly into the interior of the cushion module 110. The nose pads 1032 can extend into a stiffening portion of the seal 180, such as a thickened band 1060, which extends from one side to the other over the top of the seal 180 and is described in additional detail below. It has been discovered by the present inventors that the presence of the nose pads 1032 can result in a dramatic reduction in leaks occurring at the side of the user's nose. In addition, by terminating the nose pads 1032 prior to the opening 1000, comfort can be maintained.

It has been discovered that the nose pads 1032 should be relatively thick to improve sealing performance of the seal 180, but not so thick as to cause discomfort. In some configurations, the nose pads 1032 are among the thickest or are the thickest portions of the face contacting surface 106 of the seal 180. In some configurations, the nose pads 1032 are at least as thick as the outer peripheral portions 1046. In some configurations, the nose pads 1032 are thicker than the outer peripheral portions 1046. In some configurations, the nose pads 1032 are between about 1.5 mm and 2.0 mm in thickness. In some configurations, the nose pads 1032 are about 1.8 mm in thickness.

Figure 19:
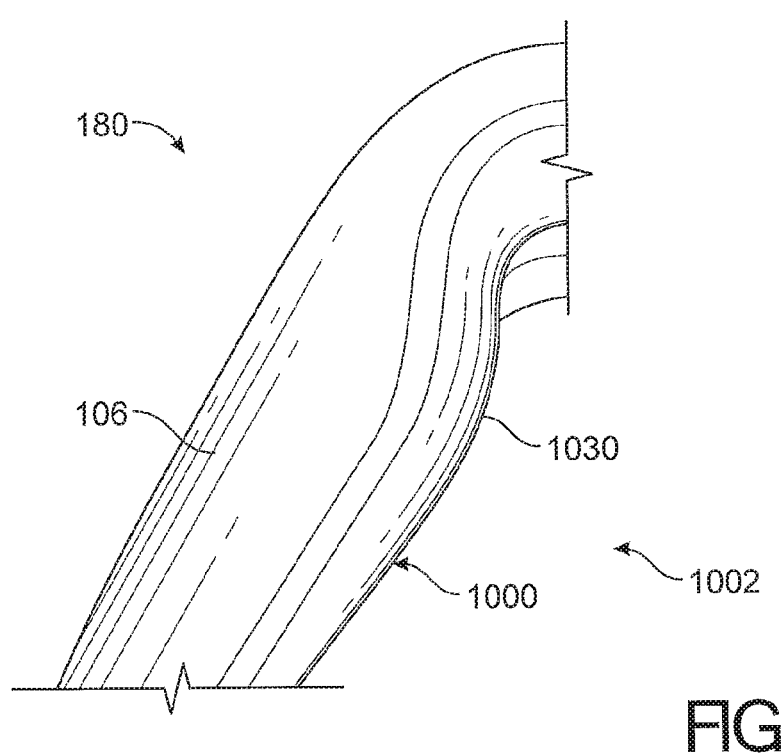
FIG. 19 is a plan view of a face contacting surface of an upper lateral portion of the seal.

With reference to FIG. 19, as described above, the illustrated seal 180 includes a continuous thin internal edge section 1030 of at least a portion of the edge that defines the opening 1000 in the upper portion 1002 of the seal 180. The continuous thin internal edge section 1030 is not necessarily a discrete section, but can be partially or completely defined by other portions of the seal (e.g., the lateral portions 1044 or nasal bridge portion 1042) so long as the entire section 1030 is below the desired thickness. In some configurations, the continuous thin internal edge section 1030 extends along about or at least about the entire upper half of the seal 180. In some configurations, the continuous thin internal edge section 1030 extends along approximately the upper two-thirds or at least about the upper two-thirds of the seal 180. In some configurations, the continuous thin internal edge section 1030 extends inwardly from the edge that defines opening 1000 at least about 0.5 mm to about 1 mm. In some configurations, the thin edge section 1030 can extend further inwardly from the edge that defines opening 1000; however, it can be desirable for further inward portions of the seal 180 to have greater thicknesses, as described above.

In some configurations, the thin edge section 1030 has a thickness that is equal to or less than about 0.6 mm or equal to or less than about 0.4 mm. In some configurations, at least the first 0.5 mm extending from the edge that defines the opening 1000 is less than about 0.4 mm in thickness. The continuous thin internal edge section 1030 can vary in thickness in a direction extending inwardly from the edge that defines opening 1000 or along its length within these desired thickness ranges. It has been discovered by the present inventors that providing the continuous thin internal edge section 1030 improves the sealing characteristics of the seal 180 for at least some conditions or facial geometries.

The seal 180 can have other portions outside of those described above. For example, the seal 180 can have one or more transition portions 1048 in the area(s) between the above-described portions. The transition portion 1048 can be referred to in the singular herein; however, the transition portion 1048 is not necessarily a single contiguous region, but may comprise several discrete or non-contiguous regions. The transition portion 1048 can define a transitioning thickness between any one or more (including all) of the chin region 1040, nasal bridge region 1042, lateral portions 1044, the outer peripheral portions 1046 and the nose pads 1032. The transition portion 1048 can define a thickness that extends away from or is positioned or transitions between two regions in any suitable manner, such as a gradual or abrupt transition, for example. A transition in thickness can occur within the transition portion 1048 or along an edge of the transition portion 1048, for example. In the illustrated configuration, the outer peripheral portions 1046 are generally surrounded by the transition portion 1048. The chin region 1040 can be separated from the outer peripheral portions 1046 by a transition portion 1048. The nasal bridge region 1042 can be separated from the outer peripheral portions 1046 and/or the nose pads 1032 by a transition portion 1048. Similarly, the lateral portions 1044 can be separated from the outer peripheral portions 1046 by a transition portion 1048. Other configurations also are possible.

Figure 20:
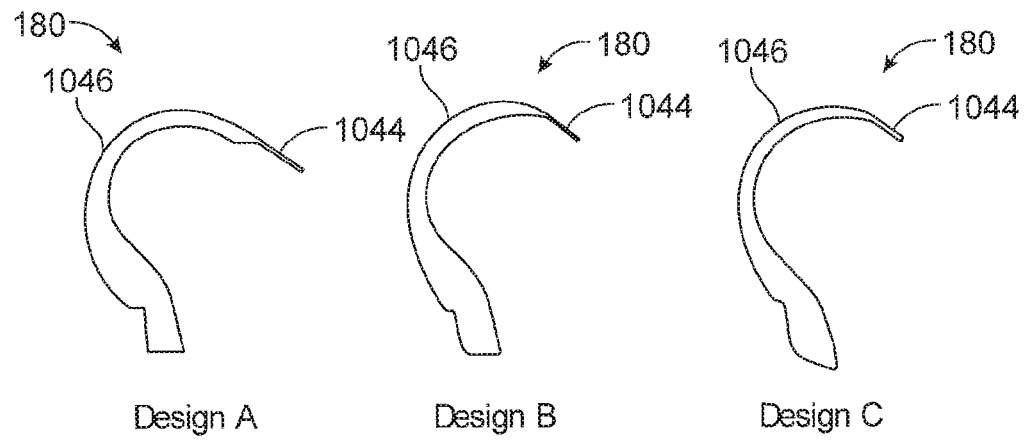
FIG. 20 illustrates several possible cross sectional profiles for a portion of the seal.

FIG. 20 illustrates several sectional views of one side of several different designs of the seal 180. The section is created by a substantially horizontal cut line through a portion of the seal 180 containing the lateral portion 1044 and outer peripheral portion 1046. Design A of FIG. 20 includes an inner surface (right side in FIG. 20) that has a relatively abrupt change in direction identified in the figure as a bend point. Thus, a different in the thickness of the seal 180 on each side of the bend point varies fairly substantially. As a result, it has been discovered that the seal 180 tends to bend around the bend point instead of deforming in a relatively uniform manner as the seal 180 is pressed against a user's face. Design B illustrates a smoother curved shape to the inner surface, which improves the ability of the seal 180 to deform in a uniform manner. Design C illustrates a further smoothed curved shape relative to Design B. Thus, Designs B and C represent an improved cross-sectional shape for the seal 180 relative to Design A, with Design C being somewhat more preferred than Design B. The more uniform the deformation of the seal 180, or the more the seal 180 cross-section changes from a generally circular shape to a generally squashed or compressed ellipse shape, rather than simply collapsing about a point or small region, the larger the seal contact area on the face, which reduces pressure on the user's skin and allows the seal to better conform to different facial geometries.

In at least some configurations, the upper portion 1002 of the seal 180 is designed to roll over onto an outer surface of the cushion module 110, which allows the nasal bridge region 1042 to move in a forward direction relative to a lower portion 1004 of the seal 180. With reference to FIGS. 21-28, to assist with the rolling of the upper portion 1002, the upper portion 1002 can have a varying thickness or a varying stiffness. While the illustrated configuration uses a region 172 of reduced thickness, other means for providing the reduced stiffness region also can be used to induce rolling of the seal 180. For example, the material of the seal 180 can be configured to have a reduced stiffness through material selection or material properties. In addition, a composite of materials can be used to provide a region of reduced stiffness or rigidity. Moreover, a combination of any suitable techniques can be used. Nevertheless, the illustrated region 172, which is configured with reduced thickness, provides a simple manner of achieving the region of reduced stiffness 172. In addition, by adjusting the stiffness of the reduced stiffness region 172, the force required to induce rolling of the region 172 can be controlled, which controls the force applied against the nose of the user. For example, by varying the stiffness, movement can become increasingly or decreasingly resisted over the range of movement. The region of reduced stiffness 172 can also be referred to as a rolling portion.

Figure 21:
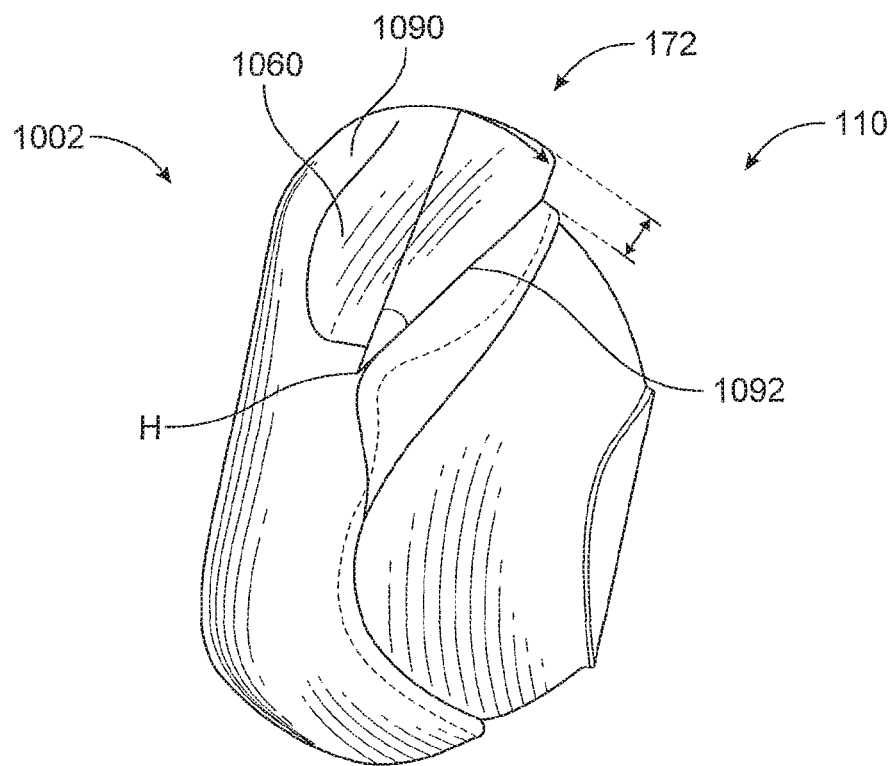
FIG. 21 is a side view of a cushion module having a deformable upper portion.
Figure 22:
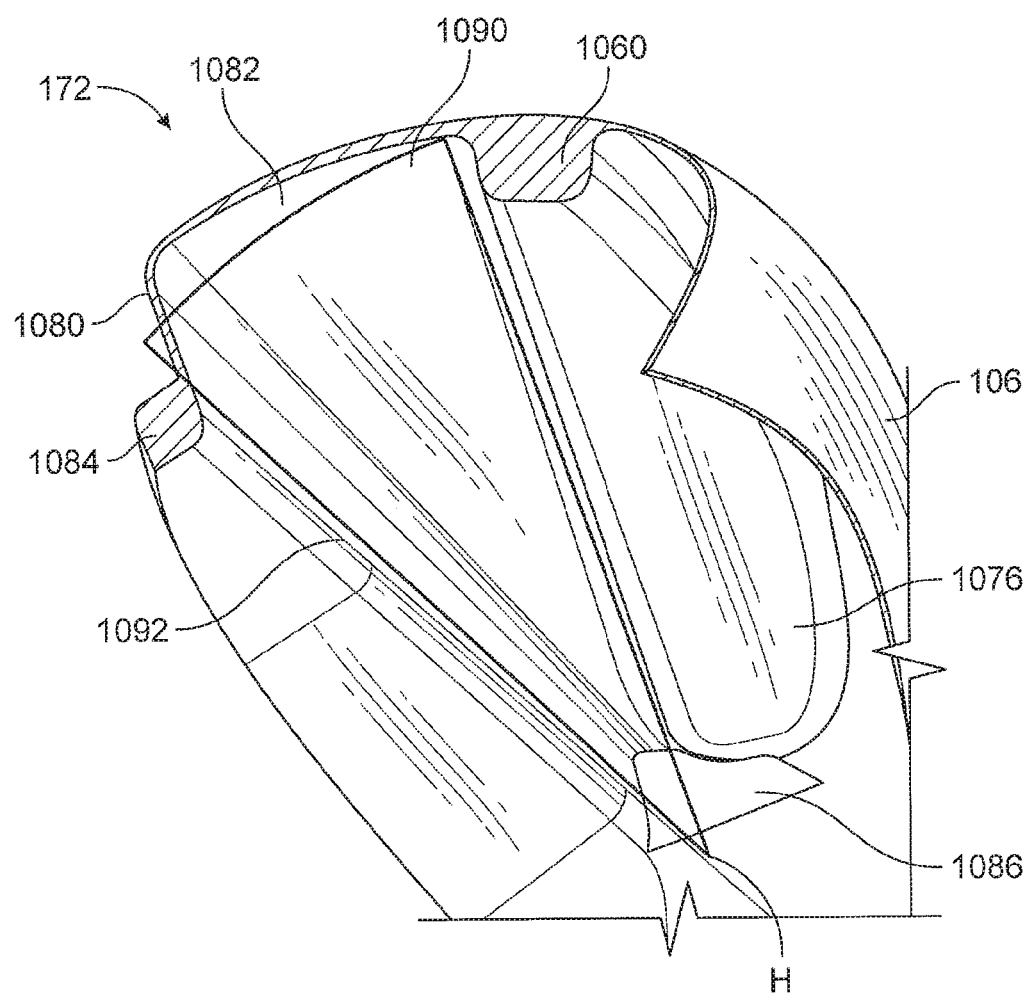
FIG. 22 is sectional view of an interior surface of the upper portion of a seal of a cushion module having a deformable upper portion.

With reference to FIGS. 21 and 22, to reduce the prevalence of ballooning in the upper portion 1002 and to provide enhanced structure in the upper portion 1002 to facilitate rolling in a desired portion of the seal 180, a reinforcing component or components, such as a band 1060, can be positioned along at least a portion of the upper portion 1002. The band 1060 can be a component formed of a material that is more rigid than, or that features increased stiffness relative to, the silicone or other material forming the seal 180. For example, a region of significantly increased thickness relative to the region of reduced stiffness 172, where the region is formed of the same material forming the seal 180, can be used to increase the stiffness of the reinforcing component or components.

In some configurations, the band 1060 can be a separately formed component that is at least partially encased by the material of the seal 180. For example, the band 1060 can be a comolded plastic component or the seal 180 can be overmolded onto the band 1060. In some configurations, the band 1060 can be defined by a portion of the upper portion 1002 that has enhanced stiffness relative to surrounding regions. For example, but without limitation, the band 1060 can be defined by a portion of increased thickness, a portion of differing materials or material properties that result in increased stiffness or the like. In the illustrated arrangement, the band 1060 comprises a region of increased thickness of the base material of the seal 180, similar to the differing regions of thickness described above with reference to FIG. 17.

In some configurations, the band 1060 extends along at least a portion of the upper portion 1002 of the seal 180. The upper portion 1002 of the seal 180 comprises an apex 1070 (FIG. 8) when viewed from the front. The apex 1070 can be defined as a tip, a top and an angular summit of the seal 180, which apex 1070 is positioned in proximity to the nose of the user when in use. A first side wall 1072 and a second side wall 1074 converge at the apex 1070 in the illustrated configuration. The first side wall 1072 and the second side wall 1074 extend along at least a portion of the upper portion 1002 of the seal 180. In some configurations, the first side wall 1072 and the second side wall 1074 extend below the upper portion 1002 into the lower portion 1004 of the seal 180.

In some configurations, at least a portion of the first side wall 1072 and at least a portion of the second side wall 1074 are reinforced by the band 1060. In the illustrated configuration, the band 1060 reinforces at least a portion of the first wall 1072 and at least a portion of the second wall 1074. In some configurations, the band 1060 reinforces at least a portion of the first wall 1072, at least a portion of the second wall 1074 and the apex 1070.

With reference to FIGS. 18 and 22, the illustrated band 1060 has a first end 1076 and a second end (not shown) that is opposite to the first end 1076. The illustrated band 1060, as well as the seal 180, is symmetrical about a center line or mid-plane of the seal 180. Accordingly, the opposite side of the band 1060 including the second end is a mirror image of the illustrated side including the first end 1076. The first end 1076 and the second end can be located at or near a bottom end of the nose pads 1032, as illustrated in FIG. 18. The first end 1076 and the second end could be located relatively higher or relatively lower to make the band 1060 shorter or longer, respectively, depending on the amount of reinforcement desired. The illustrated band 1060 flares outwardly at the ends 1076 and is narrower in a forward-rearward direction in the center. However, other shapes are also possible.

With reference to FIGS. 21 and 22, the illustrated region of reduced stiffness 172 comprises a first or front wall portion (hereinafter, front wall 1080) and a second or top wall portion (hereinafter, top wall 1082). In the illustrated arrangement, the front wall 1080 is a relatively vertical wall that extends upwardly from a connection portion 1084 between the seal 180 and the seal housing 190. The top wall 1082 is a relatively horizontal wall that extends rearwardly from an upper end of the front wall 1080 towards or to the band 1060. The illustrated front wall 1080 and the top wall 1082 are generally L-shaped in cross-section to form an angle (e.g., an approximately 90 degree angle) therebetween in a neutral or unloaded condition of the upper portion 1002 of the seal 180. However, in other configurations, the reduced stiffness region 172 could have a rounded or curved profile defined by a single wall or in which a distinction between a first wall portion and a second wall portion is less apparent.

The front wall 1080 and the top wall 1082 extend downwardly from the apex 1070 along the first and second walls 1072, 1074 (FIG. 8). In the illustrated arrangement, the front wall 1080 and top wall 1082 extend to and terminate at an inwardly-projecting shelf portion 1086 on each side of the seal 180. In the illustrated arrangement, each of the shelf portions 1086 is located just below the ends 1076 of the band 1060. The shelf portions 1086 help to influence the portion of the seal 180 that deforms along with the reduced stiffness region 172 when the upper portion 1002 of the seal 180 moves forward. In some configurations, the shelf portions 1086 contain or substantially contain the deformation of the seal 180 resulting from forward movement of the upper portion 1002 to the reduced stiffness region 172.

In some configurations, the connection portion 1084 and a forward edge of the band 1060 converge in a direction from the apex 1070 to the shelf 1086. In the illustrated arrangement, the connection portion 1084 and the forward edge of the band 1060 remain somewhat spaced from one another at or near the shelf 1086. From a side profile view, the reduced stiffness region 172 defines a generally triangular or wedge shape, as illustrated in FIGS. 21 and 22, for example.

In some configurations, the region of reduced stiffness or rolling portion 172 is located between and can be bounded by a first boundary 1090 and a second boundary 1092, wherein the first boundary 1090 and the second boundary 1092 have an increased stiffness relative to the region of reduced stiffness 172. In the illustrated configuration, for example, the first boundary 1090 is defined by or alongside a portion of the band 1060 (e.g., the forward edge of the band 1060) while the second boundary 1092 is defined by or alongside the connecting portion 1084 (e.g., origination of the front wall 1080) or a bend or transition between the front wall 1080 and the top wall 1082. In some configurations, the second boundary 1092 can be defined by or alongside an edge of the more rigid seal housing 190. In some configurations, the second boundary 1092 can be defined along a portion of the seal 180 positioned between the seal housing 190 and the region of reduced stiffness 172. A hinge axis H for movement of the upper portion 1002 of the seal 180 is defined by or is located near an intersection of the first boundary 1090 and the second boundary 1092, or projections thereof.

Figure 28:
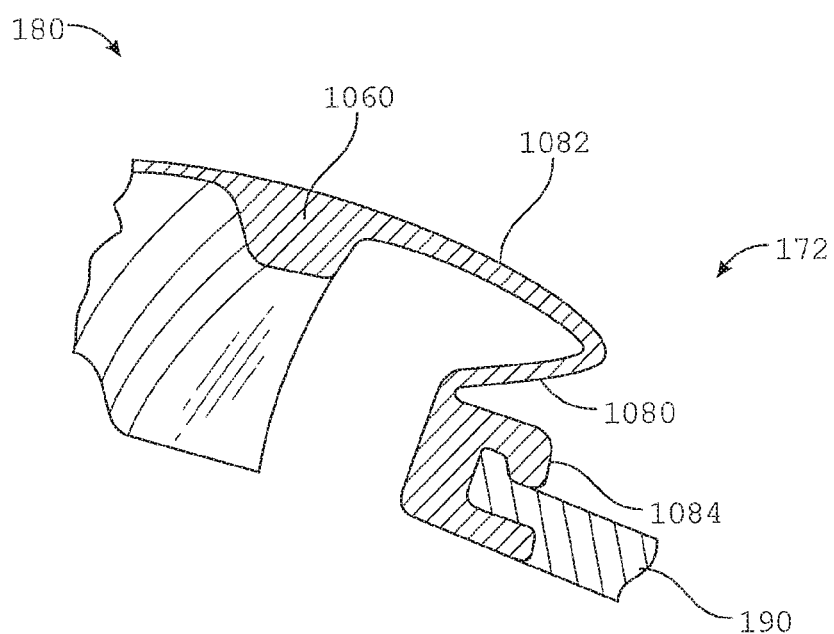
FIG. 28 is a sectional view of an upper portion of a seal deflected in a forward direction.
Figure 29A:
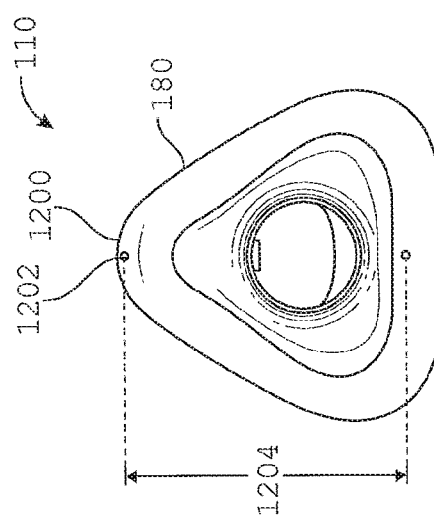
FIGS. 29A to 29F illustrate several views of a cushion module having a seal in accordance with one or more embodiments disclosed herein in a neutral position and a depressed position. A Simplus® cushion module is illustrated in similar positions for the sake of comparison.
Figure 29B:
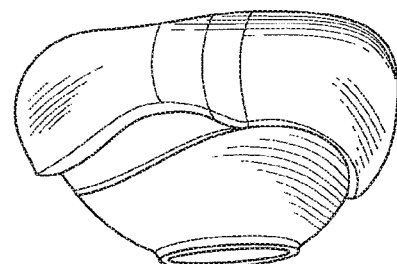
Figure 29C:
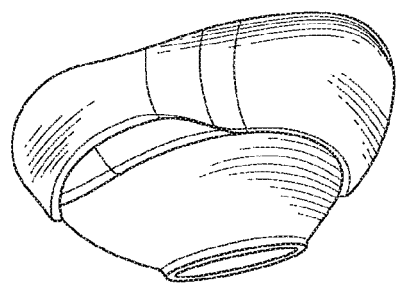
Figure 29D:
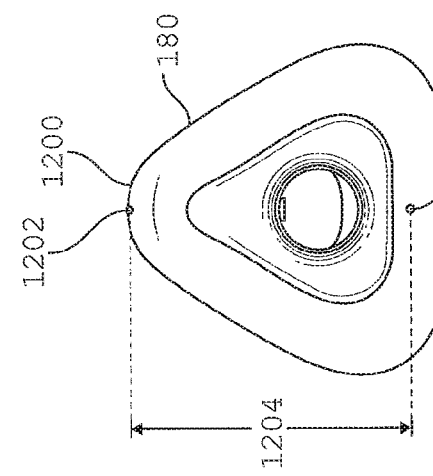
Figure 29E:
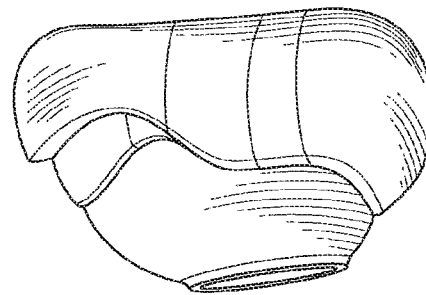
Figure 29F:
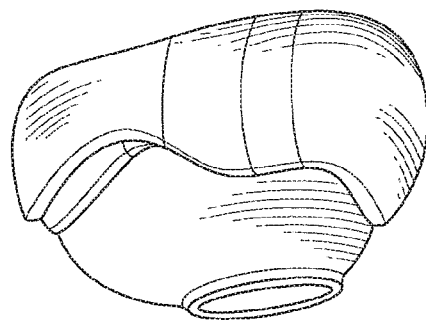

With reference to FIG. 28, as the upper portion 1002 of the seal 180 is displaced about the hinge axis H, the roll increases in size. In other words, as the first boundary 1090 initially moves toward the second boundary 1092, a roll is formed in the seal 180. As the first boundary 1090 continues to move toward the second boundary 1092, the roll continues to increase in size. Thus, in at least some configurations, the roll defined in the upper portion 1002 starts at nothing and progressively increases during displacement of the upper portion 1002. Preferably, the rolling between the first boundary 1090 and the second boundary 1092 creates a single bend or inflection between the first boundary 1090 and the second boundary 1092. The single bend results in legs approaching the bend location that increase in size as the first boundary 1090 moves toward the second boundary 1092. In other words, the rolling created by movement of the first boundary 1090 toward the second boundary 1092 preferably does not result in a fan-folding appearance, such as a pleated configuration.

In at least some configurations in which multiple size cushion modules 110 or seal 180 are provided, it can be desirable for the regions of reduced stiffness 172 of the different sizes to have different arrangements, properties or dimensions from one another. For example, the regions of reduced stiffness 172 can define different angles between the boundaries 1090, 1092 in a relaxed position between the various sizes. In addition, or in the alternative, the regions of reduced stiffness 172 can define different heights of the front wall 1080 (or different total lengths of the front wall 1080 and the top wall 1082) between the various sizes. FIGS. 23-26 illustrate different angles and different front wall 1080 heights between several sizes of a cushion module 110 or seal 180.

Figure 23:
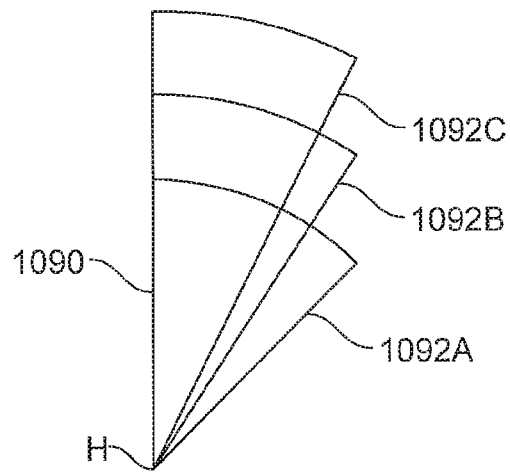
FIG. 23 illustrates a relationship between a deflection angle and forward movement of an upper portion of a seal.
Figure 24:
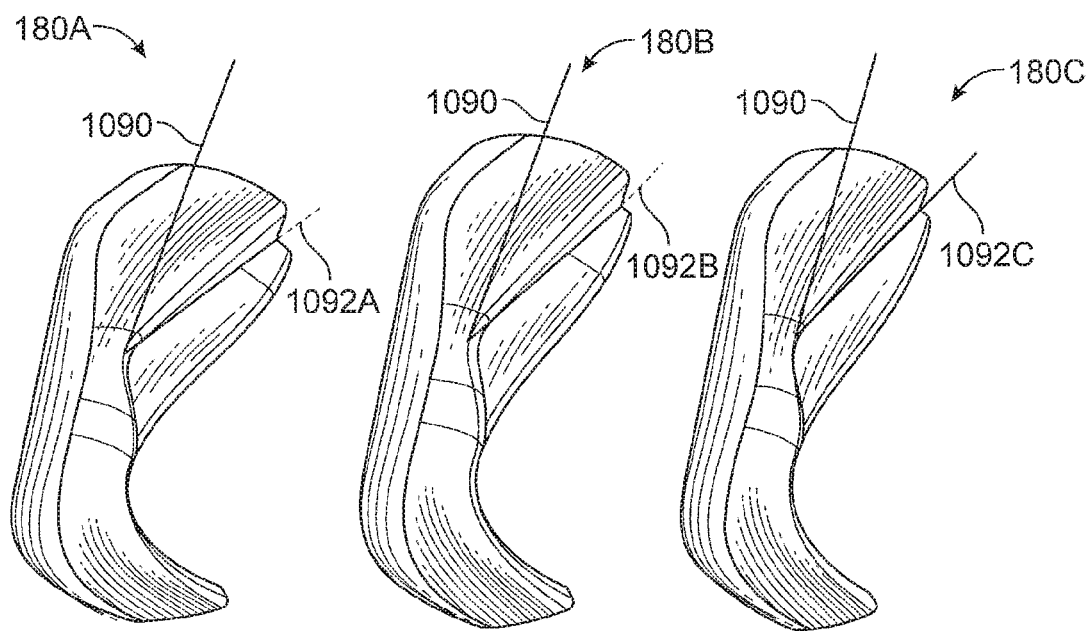
FIG. 24 illustrates several seals of different sizes having different available deflection angles.

With reference to FIGS. 23 and 24, three different sizes of seals 180A, 180B, 180C are illustrated. The seals 180A, 180B, 180C can be the seals of the three cushions modules 110A, 110B, 110C of FIGS. 8 and 9, for example. FIG. 23 illustrates a relationship between a length of the boundaries 1090, 1092 and a maximum forward displacement of the upper portion 1002. Assuming that a length of the upper portion 1002 increases or decreases along with an increase or decrease in a length of the seal 180, a length of the boundaries 1090, 1092 also increases or decreases. If the available deflection angle between the boundaries 1090, 1092 is held constant between the seal 180 sizes, the available maximum forward displacement of the upper portion 1002 is relatively less in smaller seal 180 sizes and relatively greater in larger seal 180 sizes.

For example, FIG. 23 illustrates first boundaries 1090 and second boundaries 1092A, 1092B, 1092C for three sizes of a seal 180. Assuming that all three illustrated seal 180 sizes are provided with a maximum available deflection angle (e.g., angle between the boundaries 1090 and 1092) that is equal to the maximum deflection angle of the large seal 180C, the maximum available forward displacements of the upper portions 1002 of the seals 180A and 180B are illustrated by the intersection between boundary 1092C and the arc lines of boundaries 1092A and 1092B. FIG. 23 illustrates that by increasing the angle between the boundaries 1090, 1092 in the smaller sizes, the maximum available forward displacement of the upper portions 1002 can be the same or similar between the several sized seals 180A, 180B, 180C. Thus, preferably, the angle between the boundaries 1090, 1092 is greatest in the smallest size seal 180A and smallest in the largest size seal 180C. However, in other configurations, the smallest size seal can have an angle that is greater than at least one of the larger sizes. Similarly, the largest size seal can have an angle that is less than at least one of the smaller sizes.

In some configurations, the small seal 180A defines an angle between the boundaries 1090, 1092A at a relaxed position of the upper portion 1002 of at least about 30 degrees. In some configurations, the angle is about 34 degrees. In some configurations, the medium seal 180B defines an angle between the boundaries 1090, 1092B at a relaxed position of the upper portion 1002 of between about 25 degrees and about 35 degrees. In some configurations, the angle is about 29 degrees. In some configurations, the large seal 180C defines an angle between the boundaries 1090, 1092C at a relaxed position of the upper portion 1002 of between about 20 degrees and about 30 degrees. In some configurations, the angle is about 27 degrees. However, other configurations are also possible. By way of comparison, the angle of the Simplus® seal is approximately 16 degrees for all seal sizes.

Figure 25:
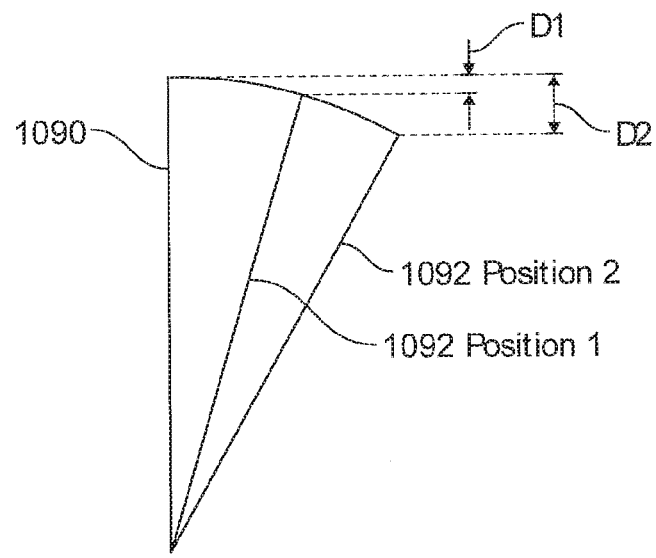
FIG. 25 illustrates a relationship between deflection angle and downward movement of an upper portion of a seal.
Figure 26:
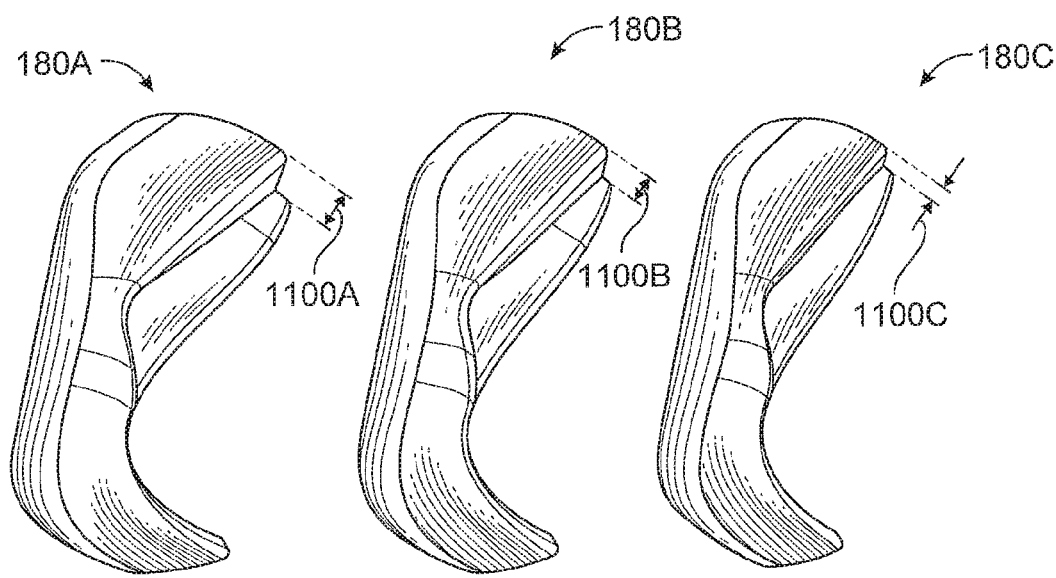
FIG. 26 illustrates several seals of different sizes having different heights of an upper portion of the seal.
Figure 27:
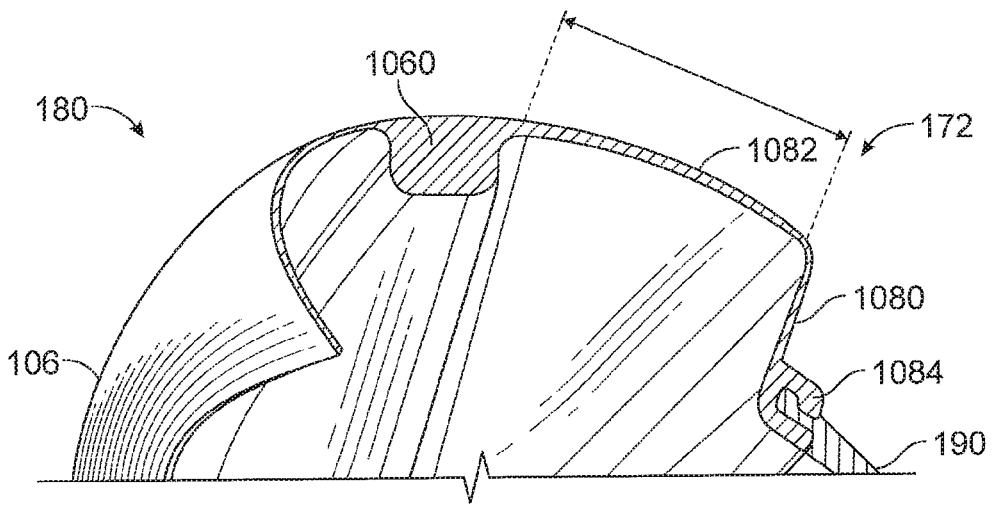
FIG. 27 is a sectional view of an upper portion of a seal, which has a progressively varying thickness in a front wall and a top wall.

FIGS. 25 and 26 illustrate differences in a height of the front wall 1080 between various seal sizes. As the angle of rotation of the upper portion 1002 of the seal 180 increases, the downward movement of the band 1060 or other boundary 1090 increases. For example, FIG. 25 illustrates a difference in downward movement D1 and D2 between a first available maximum deflection angle (represented by 1092 position 1) and a second available maximum deflection angle (represented by 1092 position 2) wherein the second angle is greater than the first angle. The downward movement D2 resulting from the greater maximum deflection angle is substantially greater than the downward movement D1 resulting from the smaller maximum deflection angle. Accordingly, the height of the front wall 1080 in the seal 180 preferably is greater than a height of the front wall in the Simplus® seal. In some configurations, a total length of the reduced stiffness region 172 is also greater in the seal 180 compared to the Simplus® seal.

FIG. 26 illustrates three different sizes of seals 180A, 180B, 180C, which can be the seals of the three cushions modules 110A, 110B, 110C of FIGS. 8 and 9, for example. The seals 180A, 180B, 180C each define a height 1100A, 1100B, 1100C, respectively, of the front walls 1080. The height 1100 can be defined by a distance between the apex 1070 and the uppermost surface of the seal housing 190 or the connecting portion 1084. In some configurations, the heights 1100A, 1100B, 1100C are greater than about 5 mm or greater than about 6 mm. In some configurations, the heights 1100A, 1100B, 1100C are greater than about 7 mm. In some configurations, at least one of the heights 1100A, 1100B, 1100C is greater than about 7.5 mm. In some configurations, the height 1100A is less than one or both of the heights 1100B, 1100C. In some configurations, the height 1100C is greater than one or both of the heights 1100A, 1100B. In some configurations, the height 1100A is smaller than 1100B and the height 1100C is greater than 1100B. In some configurations, the height 1100A is about 7.3 mm. In some configurations, the height 1100B is about 7.6 mm. In some configurations, the height 1100C is about 7.7 mm. For the sake of comparison, a comparable height of the Simplus® seal is about 4.4 mm.

The reduced stiffness region 172 and/or upper portion 1002 of the seal 180 can comprise features that facilitate desirable rolling of the upper portion 1002 of the seal 180. For example, with reference to FIG. 27, at least a portion of the reduced stiffness region 172 comprises a gradually or progressively varying thickness, which preferably increases in a direction from the forward boundary 1092 to the rearward boundary 1090. Preferably, within the progressively varying thickness portion, the thickness is lowest at or toward a forward end of the reduced stiffness region 172 and greatest at or toward a rearward end of the reduced stiffness region 172.

In some configurations, the thickness of one or both of the front wall 1080 and the top wall 1082 gradually or progressively increases in a direction from the connecting portion 1084 toward the band 1060. In the illustrated arrangement, the wall thickness increases progressively from at or near a lower end of the front wall 1080 or the connection portion 1084 to at or near the band 1060 in both the front wall 1080 and the top wall 1082. That is, the rate of change in the wall thickness is consistent between the front wall 1080 and the top wall 1082, despite the transition from one to the other. Such an arrangement allows controlled deformation of the reduced stiffness region 172, such as by allowing the bend point to move in a forward to backward direction as thinner material buckles or bends prior to thicker material buckling or bending. In other configurations, the thickness increase is different between the front wall 1080 and the top wall 1082. For example, the thickness could progressively increase in the front wall 1080 and remain constant or increase at a different rate in the top wall 1082. In other configurations, the thickness of the top wall 1082 could progressively increase and the thickness of the front wall 1080 could be constant or could increase at a different rate than the top wall 1082.

With reference to FIG. 21, an amount of overlap between the seal 180 and the seal housing 190 can vary along a perimeter of or a junction between the seal 180 and the seal housing 190. The dashed line in FIG. 21 indicates an edge of the seal housing 190. The solid line forward (to the right) of the dashed line indicates an edge of the seal 180. The seal 180 edge defines a relatively smoothly curved shape and the seal housing 190 edge defines a less smoothly curved shape. The overlap between the seal 180 and the seal housing 190 can be greater at or near a midsection of the cushion module 110 in a vertical direction relative to other portions of the cushion module 110. The variation in overlap can be to increase the retention of the seal 180 to the seal housing 190 or can simply allow the seal 180 edge to have a desirable aesthetic shape. In some configurations, the portions of increased or relatively large overlap can inhibit or prevent the seal 180 from expanding in a laterally outward direction in response to headgear forces or forces caused by gas pressure within the seal 180. In addition, in at least some configurations, the increased or relatively large overlap and/or the location of the seal housing 190 edge near the hinge axis H provides rigidity at or near the hinge axis H, which can improve the rolling or hinging motion about the hinge axis H.

With reference to FIGS. 29A-29F, the cushion module 110 is illustrated in a rear plan view, a side view in a first (e.g., neutral) position and a side view in a second (e.g., depressed or fully depressed) position. Similarly, a Simplus® cushion module is illustrated in a rear plan view, a side view in a neutral position and a side view in a depressed position. The rear plan views of FIGS. 29A-29F illustrate measuring points at a top of the seal 180 and a bottom of the seal 180 on a vertical center line. In some configurations, a height of the seal 180 is measured between two points located at a mid-point of the sealing surface on the vertical center line. The first point 1200 is located at the nasal bridge region of the seal 180 and the second point 1202 is located at the chin region of the seal 180. The points 1200, 1202 generally correspond to the location on the nasal bridge and chin of the user at which the seal 180 contacts and forms a substantially air tight seal.

A vertical distance or dimension 1204 between the points 1200, 1202 is a significant factor in determining fit of the seal 180 or cushion module 110 to a user. For example, the dimension 1204 is closely related to the Sublabiale-Sellion (SS) dimensions or lengths of the users for which the seal 180 or cushion module 110 will provide an appropriate or desirable fit. In at least some configurations, a substantial difference exists between the dimension 1204 of the seal 180 in the neutral position and the depressed position, which can be a fully depressed position. For example, the dimension 1204 can vary by more than 2 mm between the neutral and the depressed position. In some configurations, the dimension 1204 varies by at least about 4 mm, at least about 5 mm or at least about 6 mm between the neutral and the depressed position. In at least one size or embodiment of the seal 180, the dimension 1204 can vary from about 90 mm to about 84 mm between the neutral and the depressed positions. In other words, the variation of the dimension 1204 is about 6 mm. For the sake of comparison, the Simplus® cushion module varies by 2 mm between a neutral position and a fully depressed position (from about 91 mm to about 89 mm, respectively).

The variation in the dimension 1204 can allow a particular size or embodiment of the seal 180 (or cushion module 110) to fit a wider range of users. For example, the variation in the dimension 1204 can allow a particular size or embodiment of the seal 180 (or cushion module 110) to be deformed or depressed until the dimension 1204 is appropriately sized for the particular user's facial geometry (e.g., SS length). The increased variation in the dimension 1204 can be provided by the greater angular displacement of the upper portion 1002 of the seal 180 as a result of the above-described rolling action, by the increased height of the front wall 1080 or increased length of the reduced stiffness region 172, by other factors or by any combination thereof. In some configurations, a greater variation in the dimension 1204 can be provided, such as at least about 8 mm, at least about 10 mm, at least about 12 mm or more. In some cases, a greater variation is preferred, so long as other performance criteria are not impacted to an undesirable degree. In some configurations, the variation can depend on or vary with the size of the seal 180 or cushion module 110, such as with larger sizes having a greater variation in the dimension 1204 than smaller sizes. For example, the variation can be a percentage of the dimension 1204, such as any percentage covered by the values or ranges disclosed above. In some configurations, the variation in the dimension 1204 can be at least about 5 percent, at least about 6 percent, at least about 6 and ⅔ percent, at least about 8 percent, at least about 10 percent or more between the neutral position and the depressed position.

Figure 30:
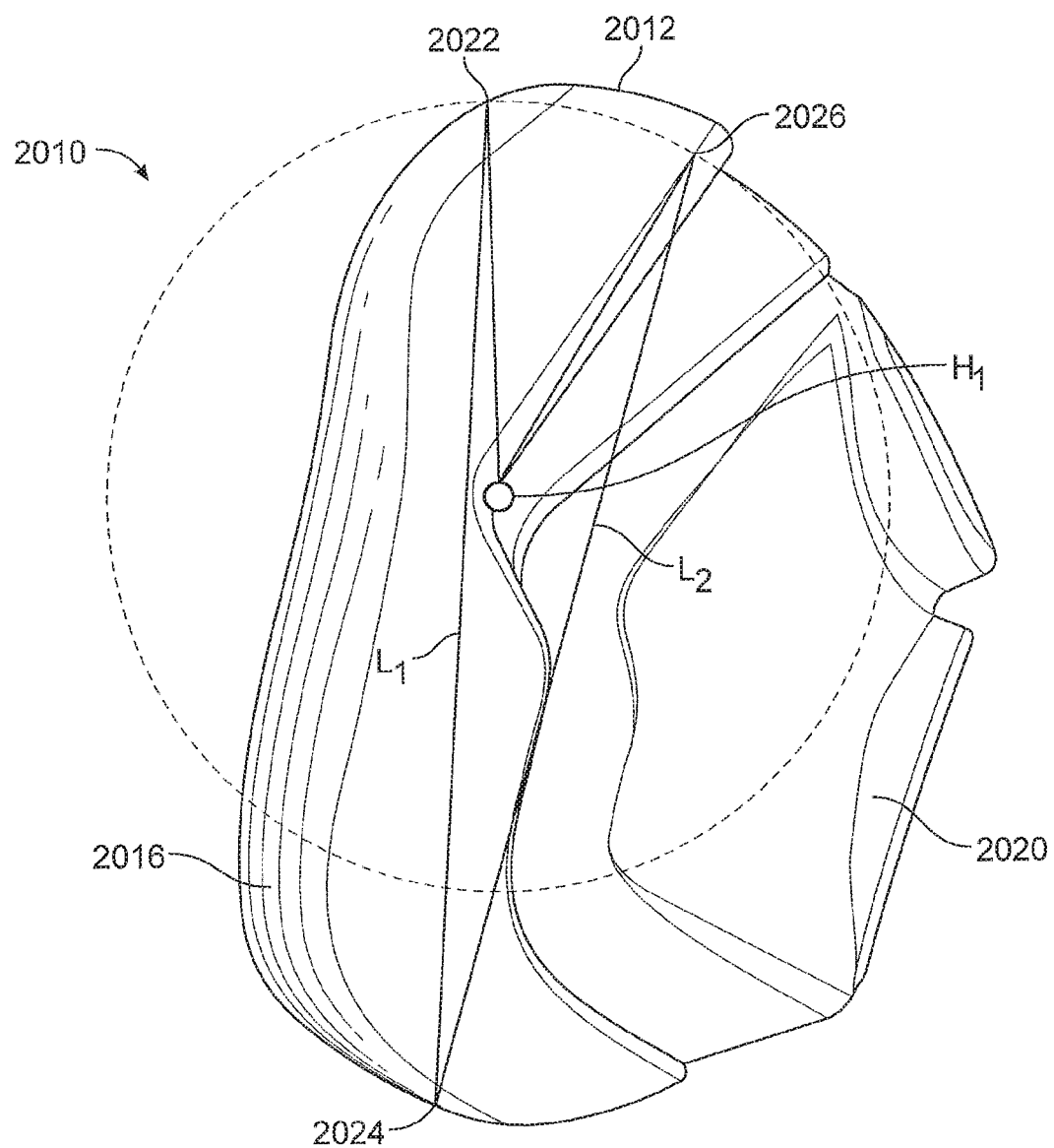
FIG. 30 illustrates a side view of a cushion module having a single rolling portion for sake of comparison.

In an alternative embodiment, the cushion module 2010 may include multiple rolling portions to accommodate differing facial geometries. For comparison, FIG. 30 illustrates a cushion module 2010 having a single rolling bridge 2012. The single rolling bridge 2012 allows a nasal contact point 2014 to rotate closer to the housing 2020 about a hinge point $H_1$ in order to allow the cushion module 2010 accommodate differing sublabiale-sellion lengths between users of different size and facial geometry. The length of the seal 2016 between the nasal contact point 2022 and the chin contact point 2024 can generally corresponds to the sublabiale-sellion length of a user's face. Accordingly, a seal length $L_1$ when the single rolling bridge 2012 is not rolled is greater than a seal length $L_2$ when the rolling bridge 2012 is rolled to a displaced nasal contact point 2026. The difference between $L_1$ and $L_2$ allows the single rolling bridge 2012 to fit a range of sublabiale-sellion lengths. The cushion module 2010 may be provided in 3 mask sizes (i.e., small, medium and large) to fit a range of sublabiale-sellion lengths. However, the number of mask sizes may be reduced while accommodating a similar range of sublabiale-sellion lengths by further rotating the single rolling bridge 2012 about the hinge point $H_1$ to provide a greater displacement of the nasal contact point 2022 (i.e., reducing the length $L_2$ when the rolling bridge is rolled).

Figure 31C:
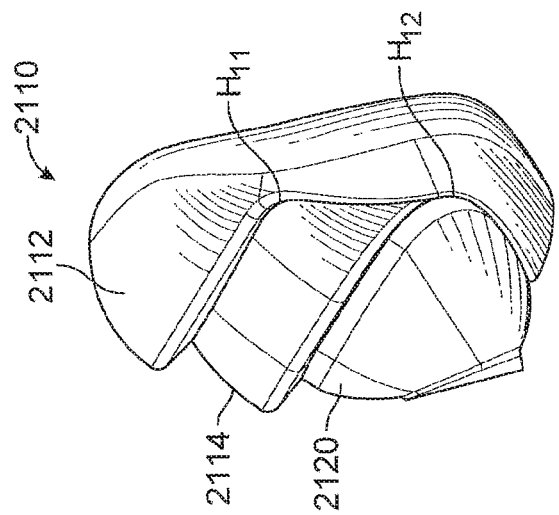
FIG. 31A to 31C illustrate various views of a cushion module with multiple rolling portions.
Figure 31B:
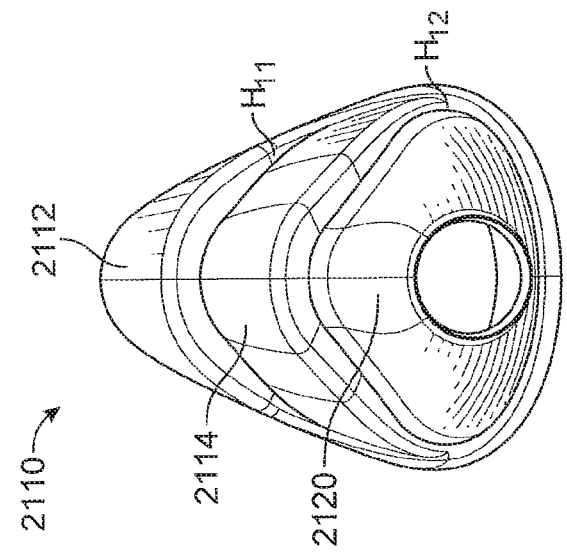
Figure 31A:
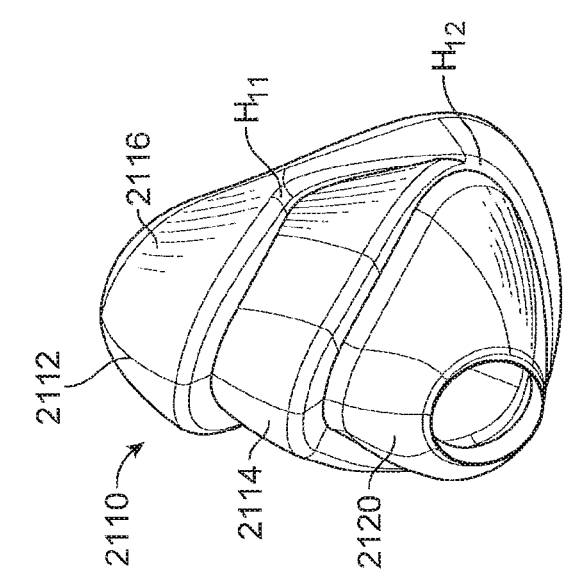
Figure 32B:
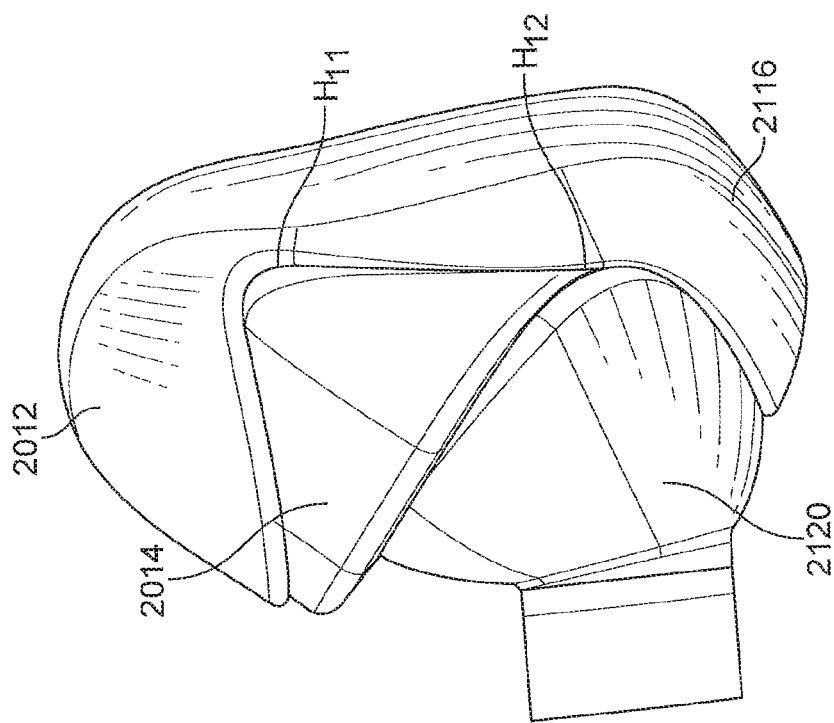
FIGS. 32A and 32B illustrates side view of the cushion module with multiple rolling portions in unrolled and fully rolled positions, respectively.
Figure 32A:
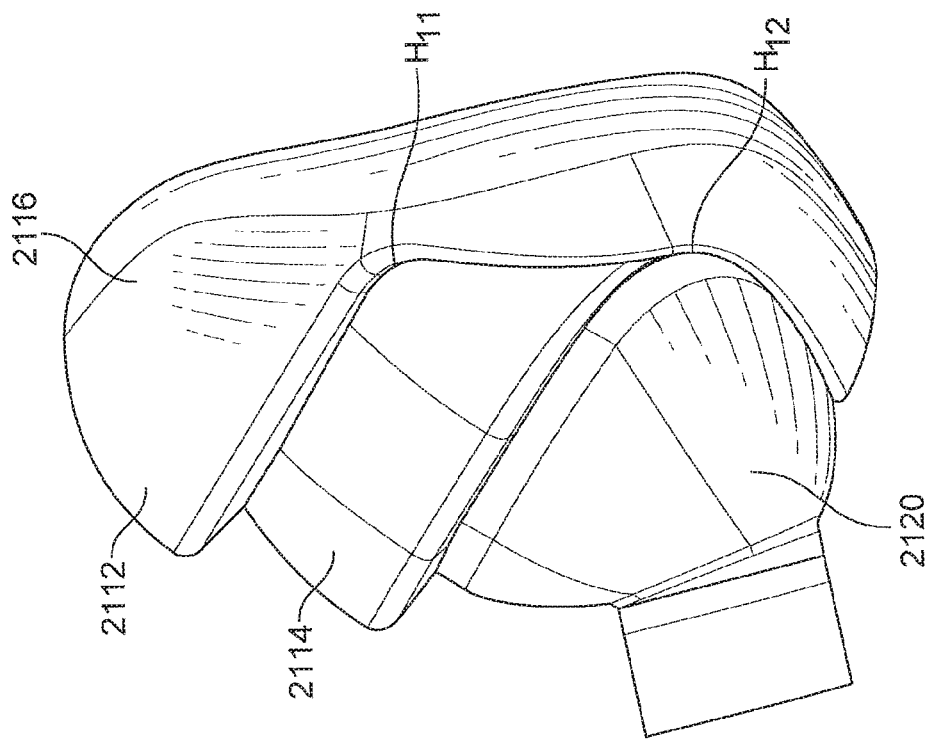
Figure 33:
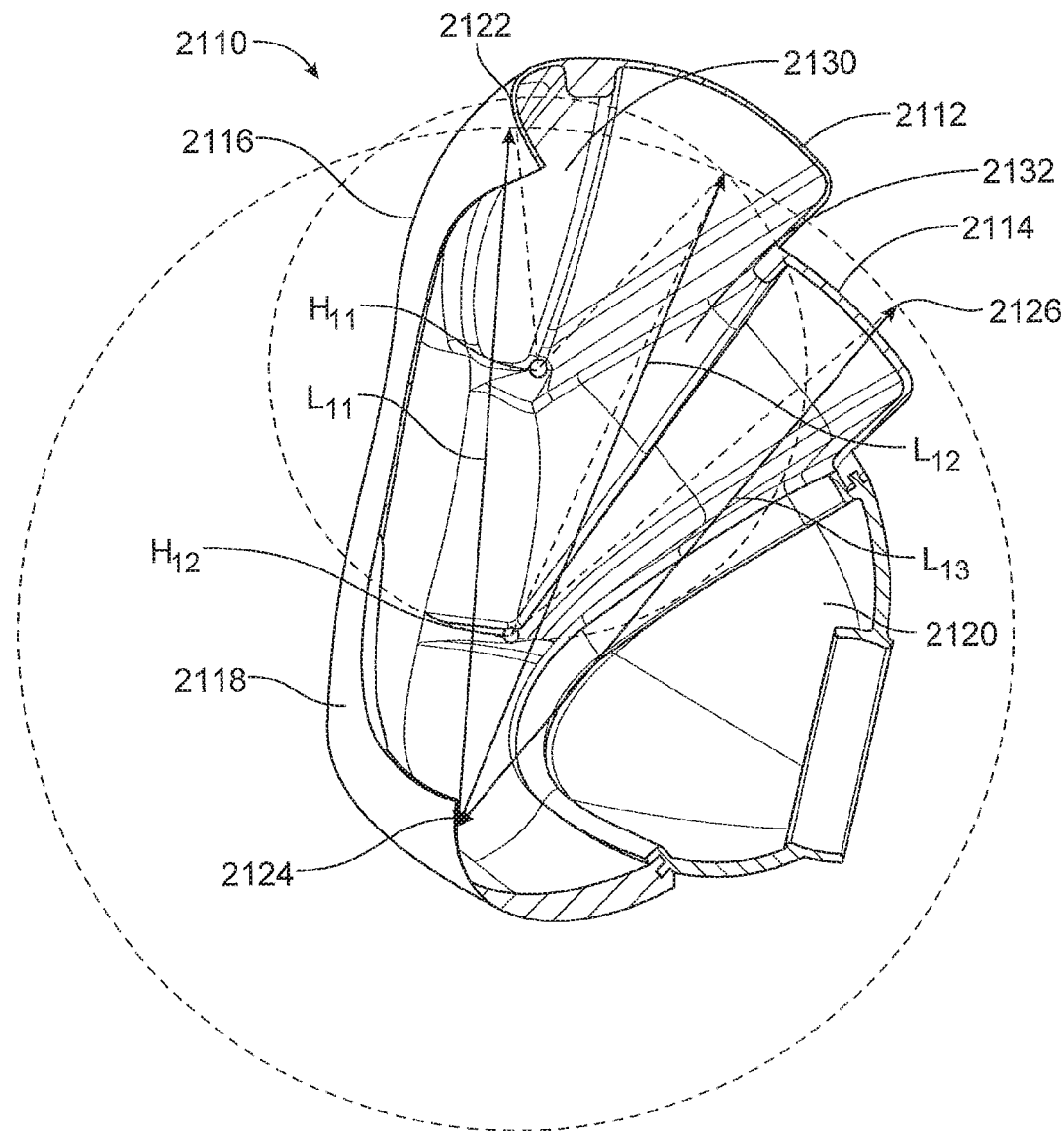
FIG. 33 illustrates a side cross-sectional view of the cushion module with multiple rolling portions.

In contrast, FIGS. 31-33 illustrates a cushion module 2110 having a first rolling portion 2112 and a second rolling portion 2114. The first rolling portion 2112 rotates about a hinge point $H_{11}$ and the second rolling portion rotates about a hinge point $H_{12}$. The second rolling portion 2114 is positioned below the first rolling portion. The first rolling portion 2112 is substantially the same as the single rolling portion 2012 in FIG. 30. However, the housing 2120 is reduced in height relative to the housing 2020 in FIG. 30 to allow for the additional rolling portion.

FIGS. 32A and 32B illustrate the cushion module 2110 in unrolled and rolled form, respectively. The first rolling portion 2112 is configured to roll over the top of the second rolling portion 2114. In use, the first and second rolling portions 2112, 2114 roll simultaneously as a result or having similar geometries that provide a similar resistance to rolling. As a result, the first rolling portion 2112 is unlikely to be fully rolled without the second portion 2114 being fully rolled.

As illustrated in FIG. 33, $L_{11}$ is a length of the seal 2116 between the nasal contact point 2122 and the chin contact point 2124 when the first and second rolling portions 2112, 2114 are not rolled. $L_{12}$ is the seal length when only the first rolling portion 2112 is fully rolled in isolation to the second rolling portion 2114. $L_{12}$ is shorter than $L_{11}$. $L_{13}$ is the seal length when both the first and second rolling portions 2112, 2114 are fully rolled to a displaced nasal contact point 2126. $L_{13}$ is shorter than both $L_{11}$ and $L_{12}$. The difference between $L_{11}$ and $L_{13}$ is greater than the difference between $L_{11}$ and $L_{12}$ and therefore allows the cushion module 2110 to fit a wider range of sublabiale-sellion lengths than the cushion module 2010 having the single rolling bridge 2012 in FIG. 30. In a preferred embodiment, $L_{11}$ has a length of approximately 102 mm and $L_{13}$ has a length of approximately 85 mm to provide a total range of approximately 17 mm.

The cushion module 2110 has a first thickened region 2130 which defines the intersection between the first rolling portion 2112 and an upper portion of a sealing surface 2118. A second thickened region 2132 defines the intersection between the first and second rolling portions 2112, 2114. The first and second thickened regions 2130, 2132 provide reinforcing structure to prevent the first and second rolling portions 2112, 2114 from collapsing when rolled. Accordingly, the first thickened region 2130 isolates the sealing surface 2118 from the rolling portions 2112, 2114 to substantially inhibit or prevent leaks from occurring when the seal is rolled.

Figure 34:
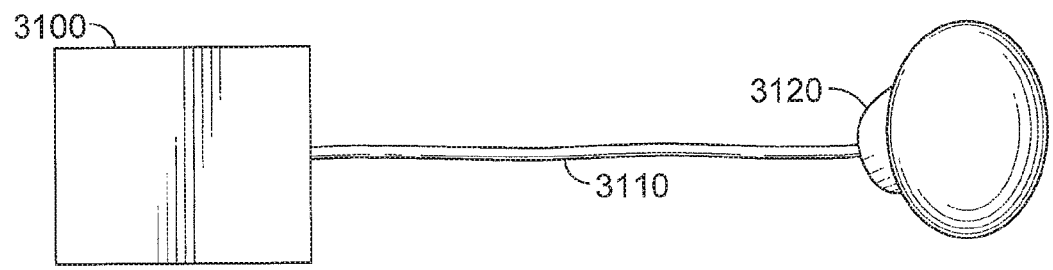
FIG. 34 shows a schematic view of a system that provides CPAP therapy to a user.

FIG. 34 shows a system for the provision of CPAP therapy to a user. The system comprises a CPAP machine 3100 configured to provide a source of pressurized breathable gases (air), an air supply hose 3110 and a respiratory mask 3120. The air supply hose 3110 is configured to provide a flow path through which pressurized air is supplied to the respiratory mask 3120 and thus a user U. Respiratory masks are available in a variety of configurations including, but not limited to, full-face, nasal and direct nasal. Typically, full-face masks are configured to substantially surround a user's nose and mouth, nasal masks generally surround the nose and direct nasal masks include pillow or prong elements that are configured to seal inside the user's nares.

The following disclosure is described in relation to nasal or direct nasal masks; however, it is to be understood that alternative embodiments are possible for other mask configurations. It is known that some direct nasal masks include a short tube component that forms a flexible intermediate connection between the respiratory mask 3120 and an air supply hose 3110, such as the Pilairo™ by Fisher & Paykel Healthcare Ltd. This tube provides a means of at least partially decoupling any forces that the air supply hose 3110 may apply to the respiratory mask 3120. The tube is generally much lighter and more flexible than the air supply hose 3110 and thus applies lower forces to the respiratory mask 3120. This can be particularly beneficial for direct nasal, and in some cases nasal, masks, because they are generally smaller and lighter, thereby making them more likely to be dislodged from a user's face if a force is applied to them. Dislodgement of the respiratory mask 3120 from the user's face may result in the efficacy of the therapy being compromised. The inclusion of a tube between the air supply hose 3110 and the respiratory mask 3120 means that forces induced by the air supply hose 3110 have to be translated through the tube in order to affect the interaction between the respiratory mask 3120 and the user. An intermediary tube such as this is utilized as a component of the bias flow venting system of the present disclosure.

Figure 35:
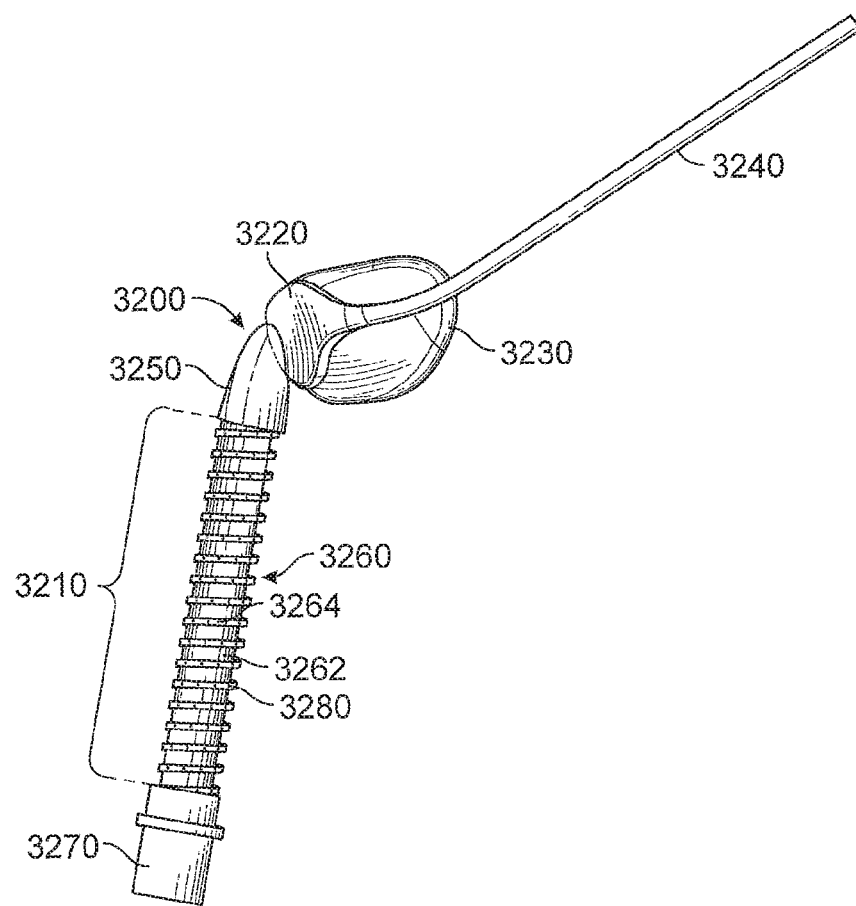
FIG. 35 shows a side view of a respiratory mask that incorporates the bias flow venting system of the present disclosure.

FIG. 35 shows a respiratory mask 3200 comprising the bias flow venting system 3210 of the present disclosure. The respiratory mask 3200 also comprises a mask frame 3220, a seal 3230, a head strap 3240, an elbow 3250, a tube 3260, and a swivel 3270.

Figure 36:
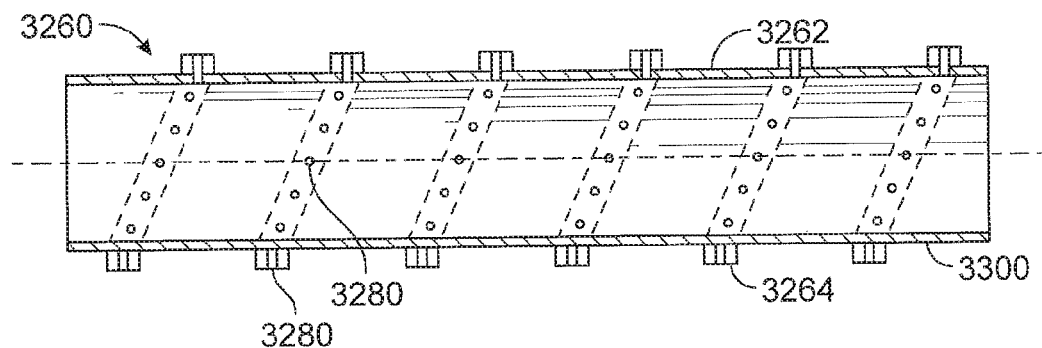
FIG. 36 shows a cross-sectional view of the bias flow venting system of the present disclosure.

The bias flow venting system 3210 comprises the tube 3260 and an annular array of radially aligned exhaust holes 3280. The tube 3260 comprises wall 3262 and a bead 3264. The wall 3262 is configured to be substantially cylindrical and comprises a thin and flexible film that can be made from any suitable thermoplastic, such as but not limited to polyurethane Elastollan 1180A. The bead 3264 is configured to provide structure to the wall 3262 that reduces or eliminates the likelihood of crushing and occlusion of the tube 3260. The bead 3264 extends along the length of the tube 3260 in a helical configuration and has a cross-sectional profile that is raised from the outer surface 3300 of the wall 3262, as shown in FIG. 36. The cross-section of the bead 3264 is substantially rectangular and may have rounded edges (not shown). In alternative embodiments, the bead 3264 may have any other suitable geometry, such as, but not limited to, semi-circular, elliptical, polygonal or asymmetric. The cross-sectional geometry of the bead 3264 in combination with material selection determines the rigidity of the bead 3264 and, thus, the structural support provided to the wall 3262. The bead 3264 is made from a material, such as, but not limited to, polyurethane Elastollan 1174D, which is substantially more rigid than the material of the wall 3262. The flexibility of the wall 3262 in comparison to the bead 3264 is such that tube 3260 can be compressed along a central axis in a spring-like manner, wherein the wall 3262 folds or deforms to allow pitch of the bead 3264 to be reduced. In alternative embodiments (not shown), the pitch of the bead 3264 may be varied along the length of the tube 3260 such that the amount of deformation along different portions along the length of the tube 3260 may vary. Even further, the pitch of the bead 3264 may be varied along portions of the tube 3260 such that the tube 3260 may have a curved shaped.

Figure 37:
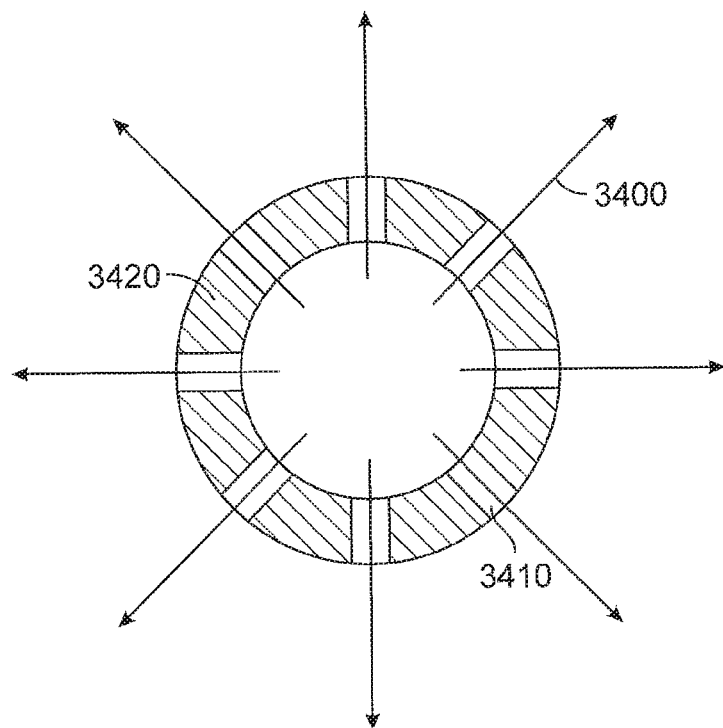
FIG. 37 shows a cross-sectional view of a cylindrical conduit with radial exhaust holes.

The exhaust holes 3280 are formed within the bead 3264 and are spaced radially or helically around the perimeter of the tube 3260 at regular intervals. The exhaust holes 3280 are configured to provide a path for air to be exhausted from within the respiratory mask 3200. The exhaustion of air from within the mask 3200 allows $CO_2$ to be flushed, thus preventing rebreathing of the $CO_2$ by the user. The radial alignment of the exhaust holes 3280 allows exhausted air to be dispersed over a range of 360°. FIG. 37 displays an example of how exhausted air 3400 can be dispersed over a wide area (360°) by radially aligned holes 3410 within a cylindrical conduit 3420. The radially aligned holes 3410 or exhaust holes 3280 result in the flow paths for exhausted air being divergent, which minimizes the air flow that can be detected in any one position relative to the cylindrical conduit 3420 or tube 3260. The radial arrangement and spacing of exhaust holes 3280 in the helical bead 3264 may help to minimize any entrainment of air, which may cause greater draft to be detected by users. The formation of the exhaust holes 3280 on the helical bead results in the individual exhaust holes being offset longitudinally from each other. This further increases the dispersion of exhausted air. The location of the exhaust holes 3280 within the bead 3264 is desirable as it reduces or eliminates the likelihood of the holes being crushed or blocked by deformation of the tube 3260. In alternative embodiments (not shown), the exhaust holes 3280 may only be spaced around a portion of the perimeter of the tube 3260 (e.g., 180°) or may be formed in a tube wall rather than a bead. For example, the exhaust holes 3280 may be positioned on only outward facing portions of the tube 3260 relative to the user such that the exhausted air exits the tube 3260 away from the user. In other alternative embodiments (not shown), the exhaust holes 3280 may be angled relative the axial length of the tube 3260. For example, the exhaust holes 3280 may be positioned at a non-orthogonal angle that extends away from the respiratory mask along the axial direction. Accordingly, exhausted air will be directed away from the user.

The exhaust holes 3280 can have any suitable cross-sectional geometry, including, but not limited to, circular, elliptical, polygonal or asymmetric. In an embodiment where the exhaust holes 3280 are circular, the hole diameter can be at least approximately 0.1 mm and/or less than or equal to approximately 1.5 mm. Diameters of less than 0.5 mm may be advantageous in reducing noise generated by any exhausted air. In a preferred embodiment, the exhaust holes 3280 have a diameter of approximately 0.4 mm. The exhaust holes 3280 are formed by laser drilling or cutting, which allows for the radial alignment of the exhaust holes and the formation of holes with small diameters (i.e. less than 0.5 mm). The diameter and spacing of the exhaust holes 3280 may be dependent on the total number of holes required to effectively flush $CO_2$ from within the respiratory mask 3200. The exhaust holes 3280 can be spaced at a maximum distance from each other that allows the total number of required exhaust holes to fit within the tube 3260. In some embodiments (not shown), the exhaust holes 3280 may be spaced along only a portion of the tube length. For example, the exhaust holes 3280 may only be positioned on a bottom portion of the tube 3260 such that the exhausted air exits the tube 3260 away from the head of the user. Accordingly, noise from exhausted air is less likely to disturb the user due to the increased distance between the user's head and the exhaust holes 3280. In some such embodiments (not shown), the exhaust holes 3280 can be spaced at a maximum distance from each other that allows the total number of exhaust holes to fit within the portion of the length of the tube. In other alternative embodiments (not shown), the exhaust holes may be spaced along a length of the tube 3260 at irregular intervals. For example, the spacing between the exhaust holes 3280 may increase or decrease along the length of the tube 3260 depending on airflow and noise requirements.

In alternative embodiments (not shown), variations of the presently disclosed bias flow venting system may be incorporated into tubes of different configurations. A wide range of plastic tube configurations are available in industry, including but not limited to plane cylindrical tubes and corrugated tubes. Exhaust holes may be incorporated into any appropriate part of the tube structure.

Figure 38:
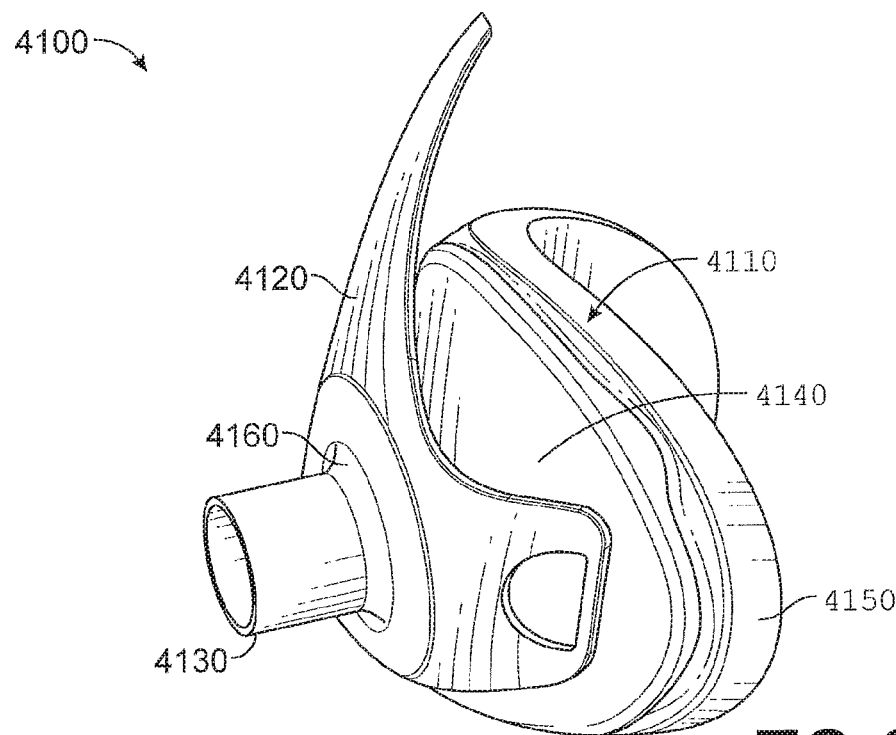
FIG. 38 shows a perspective view of a respiratory mask comprising the bias-flow venting system of the present disclosure.

FIG. 38 shows a bias-flow venting system for use in expelling exhausted air from within a respiratory mask. The venting system generally provides a path through which air, which is exhaled by a user, may be exhausted to atmosphere.

As shown in FIG. 38, a respiratory mask 4100 incorporates a bias-flow venting system as per the presently disclosed subject matter. The respiratory mask 4100 includes a cushion module 4110, a mask frame 4120, and an air supply connection 4130. The cushion module 4110 comprises a seal housing 4140 and a seal 4150. The mask frame 4120 comprises a shroud 4160.

Figure 39:
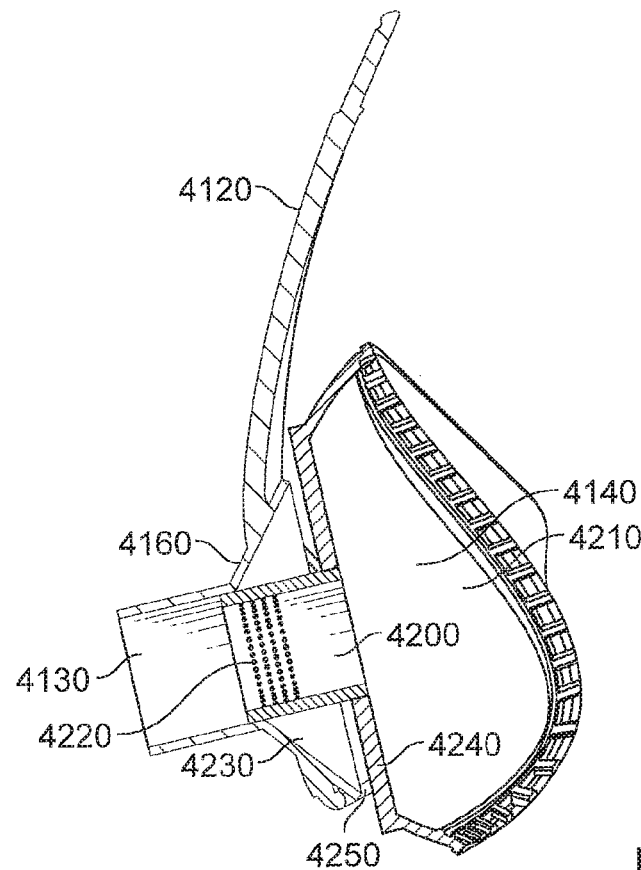
FIG. 39 shows a cross-sectional view of the respiratory mask and bias-flow venting system of the present disclosure.

As shown in FIG. 39, there is an annular component 4200 extending from a front wall 4240 of the seal housing 4140. The annular component is connected to the mask frame 4120 forming a fluid connection between the cushion module 4110 and the air supply connector 4130. The connection between the annular component 4200 and the mask frame 4120 may be configured to include a snap-fit connection that enables the two components to be disassembled for cleaning. Alternatively, the connection can be permanent and the components may be fixed together by any suitable means known in the art, such as gluing or welding. The air supply connector 4130 and the annular component 4200 can be aligned and/or connected such that any air supplied to the mask via the air supply connector 4130 passes through the annular component 4200 and into the breathing chamber 4210 formed by the seal housing 4140.

The annular component 4200 may be formed as a separate component and then attached to an aperture in the seal housing 4140. The connection between the annular component 4200 and the seal housing 4140 may be achieved by an interference type snap-fit geometry, gluing, welding or any other appropriate connection process. An interference type snap-fit may be configured to allow adjustability between the annular component 4200 and the seal housing 4140 by providing discrete positions of adjustment. Alternatively, the annular component 4200 and the seal housing 4140 can be molded as an integral component. Alternatively, the mask frame 4120 may be a common size in which cushion modules 4110 of various sizes (e.g., small, medium, large) may be connected.

The annular component 4200 is configured to include an array of exhaust holes 4220. The exhaust holes 4220 can be radially spaced around the perimeter of the annular component 4200. The radial placement of the exhaust holes results in the exhausted air being dispersed around 360° of the annular component 4200, as can be seen in FIG. 40.

Figure 40:
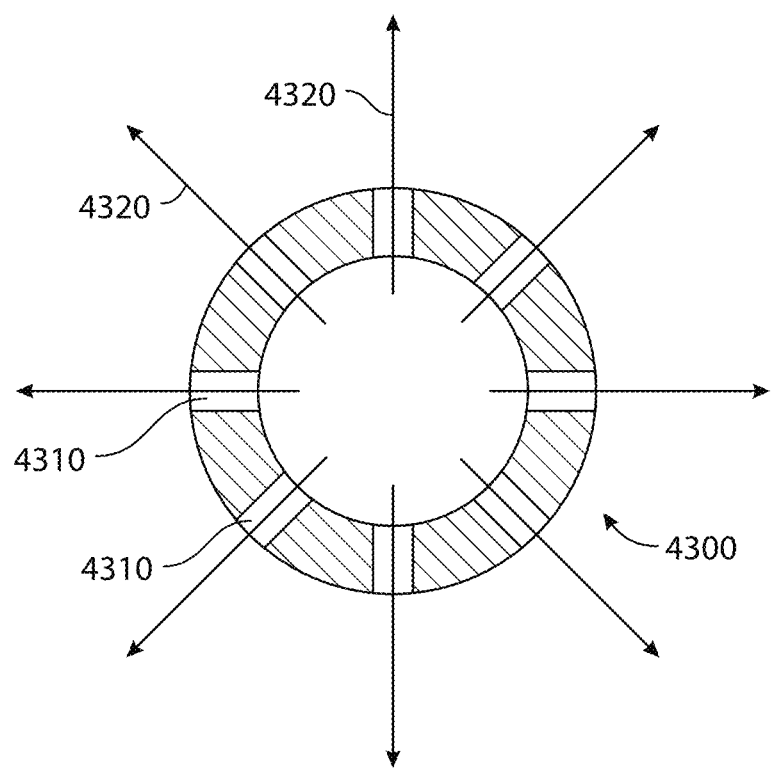
FIG. 40 shows a cross-sectional view of an annular component with radial exhaust holes.

FIG. 40 shows an exemplary cross-sectional view of a cylindrical or annular component 4300 that has radial exhaust holes 4310. The arrows shown in FIG. 40 demonstrate how exhausted air 4320 is dispersed through the holes 4310. This dispersion is beneficial because it reduces the draft that can be detected in any one position relative to the annular component 4200 by dispersing the exhausted air 4320 over a greater area. The radial arrangement of the holes and the spacing between holes may minimize entrainment of atmospheric air, which may cause increased drafts to be detected by users.

In one non-limiting exemplary embodiment, the exhaust holes are preferably formed by laser drilling. Laser drilling allows the radial hole arrangement and a small hole diameter be formed. The hole diameter may be approximately 0.4 mm. As used herein in connection with dimensions, the term approximately should be understood to mean within standard manufacturing tolerances or deviations that result and/or can be expected during manufacturing. In addition, the term approximately can extend up to and including dimensions that would round to the stated value. With this said, laser drilling the holes may provide a tighter tolerance on the hole diameter than traditional forming methods, such as molding. Small hole diameters may be beneficial to reduce draft and noise. Alternatively, traditional molding techniques can be used to form the exhaust holes 4220 in the annular component 4200. The number of holes can be determined by the flow rate desired to effectively flush $CO_2$ from within the breathing chamber 4210 of the mask.

The annular component 4200 and the exhaust holes 4220 can be surrounded by a shroud 4160. The shroud 4160 can be an integrally formed portion of the mask frame 4120 and can extend radially from the user end (in use) of the air supply connector 4130. The shroud 4160 has a substantially conical geometry. The shroud 4160 creates a plenum chamber 4230 between the mask frame 4120 and the front wall 4240 of the seal housing 4140. A radial vent path 4250 can be formed between the outer perimeter of the shroud 4160 and the front wall 4240. The radial vent path 4250 allows the exhausted air to remain dispersed over 360°, which can reduce detectable draft.

Air can be exhausted through the exhaust holes 4220 into the plenum chamber 4230 formed by the shroud 4160, the annular component 4200, and the front wall 4240 of the seal housing 4140. As the exhausted air passes through the exhaust holes 4220, the exhausted air is accelerated. However, routing of the exhausted air into the plenum chamber 4230 prior to exiting through the vent path 4250 causes the exhausted air to be slowed down and redirected. The space of the plenum chamber forms an expansion chamber that allows the energy present in the exhausted air to dissipate before it exits the shroud 4160 via the vent path 4250. This enables the fluid velocity of air passing through the exhaust holes 4220 to be reduced and the fluid pressure to be increased, which results in the reduction or prevention of entrainment of atmospheric air. The reduction in fluid velocity and entrainment substantially reduces or prevents detection of drafts by the user.

Figure 41:
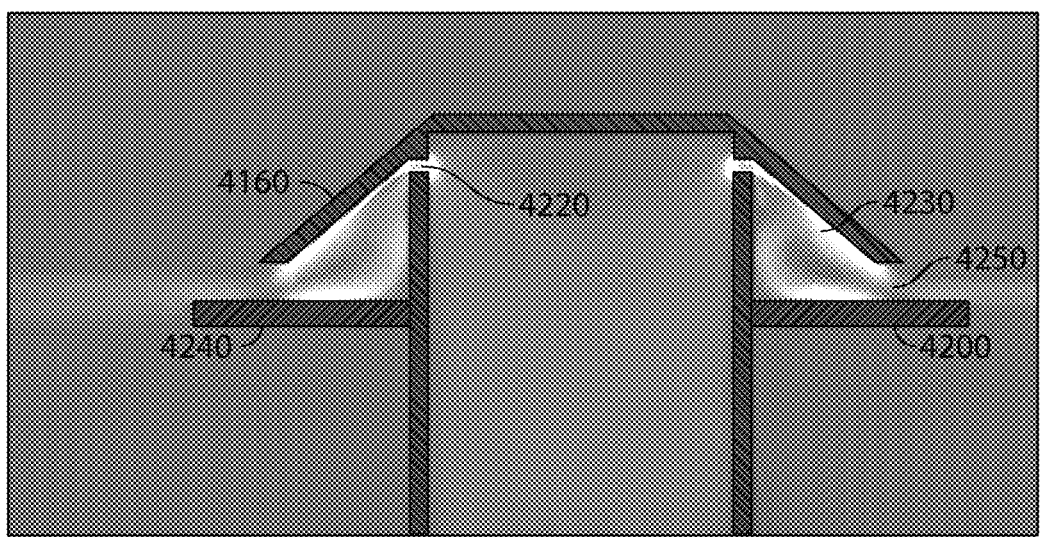
FIG. 41 shows a computational fluid dynamics (CFD) analysis diagram of the exhaust hole and shroud geometry of the present disclosure.

FIG. 41 shows a screen shot of a computational fluid dynamics (CFD) analysis of the exhaust hole 4220 and shroud 4160 geometry. It can be seen from the cross-sectional view that the fluid velocity is substantially reduced where the air exits via the vent path 4250. It can also be seen that the geometry of the shroud 4160 and plenum chamber 4230 results in a re-circulation of the exhausted air. This can be seen by the higher velocities (i.e., lighter regions) adjacent the front wall 4240 and annular component 4200. This recirculation allows the energy within the exhausted air to be dissipated before it exits the vent path, which further reduces drafts and noise.

The exhaust flow rate from the mask is determined by the size and number of exhaust holes 4220 rather than the cross-sectional area of the vent path 4250. The size of the vent path can be altered to affect the velocity of exhausted air and thus the draft and noise generated by the exhausted air. For example, the vent path 4250 may be widened or narrowed by adjusting the position of the annular component 4200 with respect to the seal housing 4140 to vary the distance between the front wall and the shroud 4160. As mentioned above, discrete positions of adjustment may be provided by the interference type snap-fit between the annular component 4200 and the seal housing 4140 such that the size of the vent path 4250 may be altered.

Figure 42A:
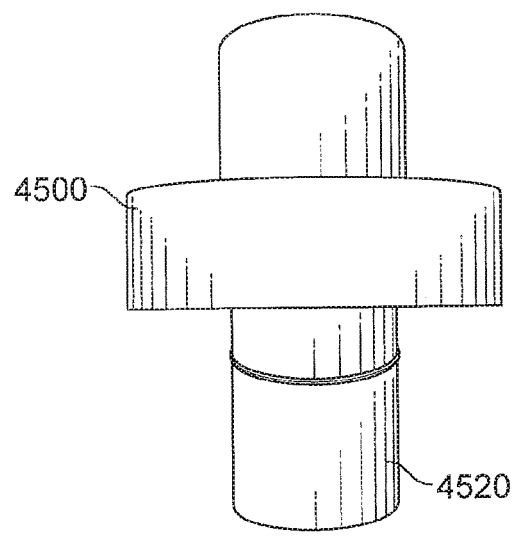
FIGS. 42A and 42B show alternative embodiments of shroud geometry.
Figure 42B:
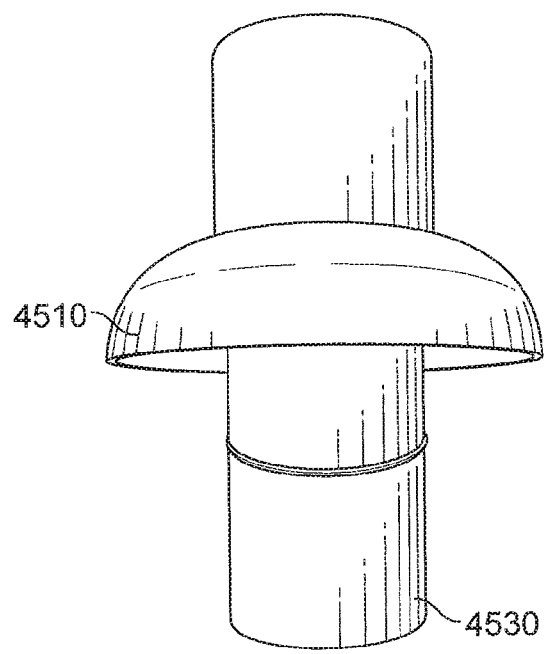

Additional non-limiting exemplary embodiments of shroud geometry can be seen in FIGS. 42A and 42B. The figures show shrouds 4500, 4510 with rectangular and arcuate cross-sections respectively surrounding annular components 4520, 4530. As in the embodiment of FIGS. 38 and 39, the shroud creates a plenum chamber adjacent to the annular component 4520, 4530. Even further, the plenum chamber may include flow directors such as fins, vanes, and/or baffles (not shown) positioned within the plenum chamber. For example, fins and vanes may guide exhaust air through the plenum chamber to the vent path 4250. Baffles may be used to dissipate energy from the flow of exhausted air. Yet further, the size, shape, number, position and/or arrangement of the exhaust holes may be varied around the perimeter or along the axial length of the annular component 4200. In other words, the exhaust holes 4220 are not limited to a uniform size and arrangement along the annular component 4200. In combination with the shroud geometry, the size, number, position and/or arrangement of the exhaust holes may be varied around the perimeter or along the axial length of the annular component 4200 to allow the velocity of the exhausted air to be varied within the shroud 4160. For example, the diameter or number of the exhaust holes may decrease along the axial length such that the velocity of the exhausted air is higher closest to shroud 4160. Accordingly, the flow of exhausted air may vary depending upon the position of the exhaust hole relative to the shroud 4160 which may allow recirculation, noise and turbulence to be optimized.

Figure 43A:
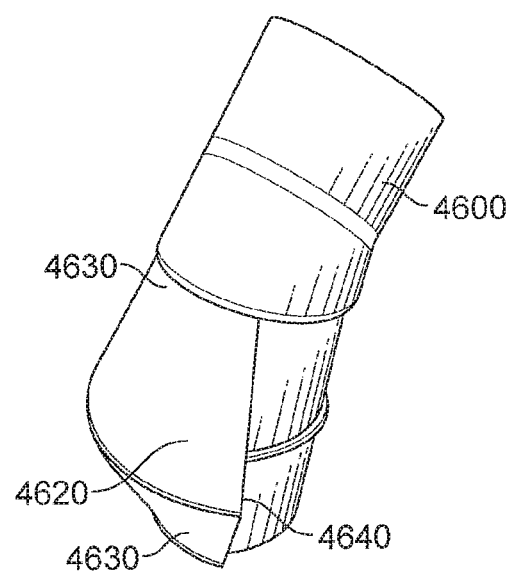
FIGS. 43A and 43B show an embodiment of the bias-flow venting system as applied to an elbow.
Figure 43B:
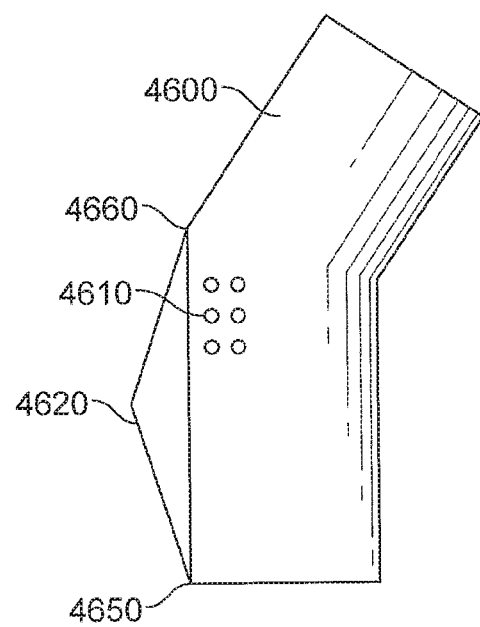

In other non-limiting exemplary embodiments of the present disclosure the exhaust holes and shroud may be positioned on different parts of a respiratory mask. For example the holes and shroud may be part of an elbow or swivel conduit connector. Elbows and/or swivels are commonly used in respiratory masks to provide an intermediate connection between an air supply conduit and the mask. In the non-limiting exemplary embodiment of FIGS. 43A and 43B, the exhaust holes and shroud are located on an elbow. FIG. 43B shows a simplified cross-sectional view of the embodiment of the present disclosure. The embodiment comprises a cylindrical elbow 4600, exhaust holes 4610 (not shown in FIG. 43A) and a shroud 4620.

Like the previous embodiment, the exhaust holes 4610 can be positioned radially on an annular surface. The exhaust holes 4610 and shroud 4620 extend only part way around the surface of the elbow. The holes can be arranged to disperse the exhausted air over an angle of around 120°. The shroud 4620 extends slightly beyond the edges of the outer holes. The shroud 4620 can have a partially biconical geometry, wherein the shroud forms a segment of a bicone that has been truncated at both of the apexes. The truncated edges 4630 of the biconical shroud 4620 are attached to the cylindrical elbow 4600 on either side of the exhaust holes 4610 at both the first end 4650 and the bend 4660 in the cylindrical elbow 4600. The shroud edges 4640 are open and not connected to anything. The open shroud edges 4640 provide a path through which exhausted air is vented to atmosphere.

The size and number of holes can be similar to the previous embodiment and can be based on the exhaust flow rate desired to flush $CO_2$ from within the mask. In other variations of this embodiment, the shroud 4620 may be conical rather than biconical and may have one end that is larger than the other. The shroud may also have a square, rounded or any other appropriate geometry as an alternative to the conical geometry.

The inclusion of a shroud component around the exhaust holes in a respiratory mask can take a variety of forms depending upon the configuration of other mask components. It can be desirable for a respiratory mask to have a ball and socket connection between an elbow and a mask frame or seal housing. This can reduce hose drag on the mask. In masks with this elbow configuration, the exhaust holes and shroud can be incorporated into the ball socket for the elbow. Several non-limiting exemplary embodiments of this are shown in FIGS. 44A to 44D and 45.

Figure 44A:
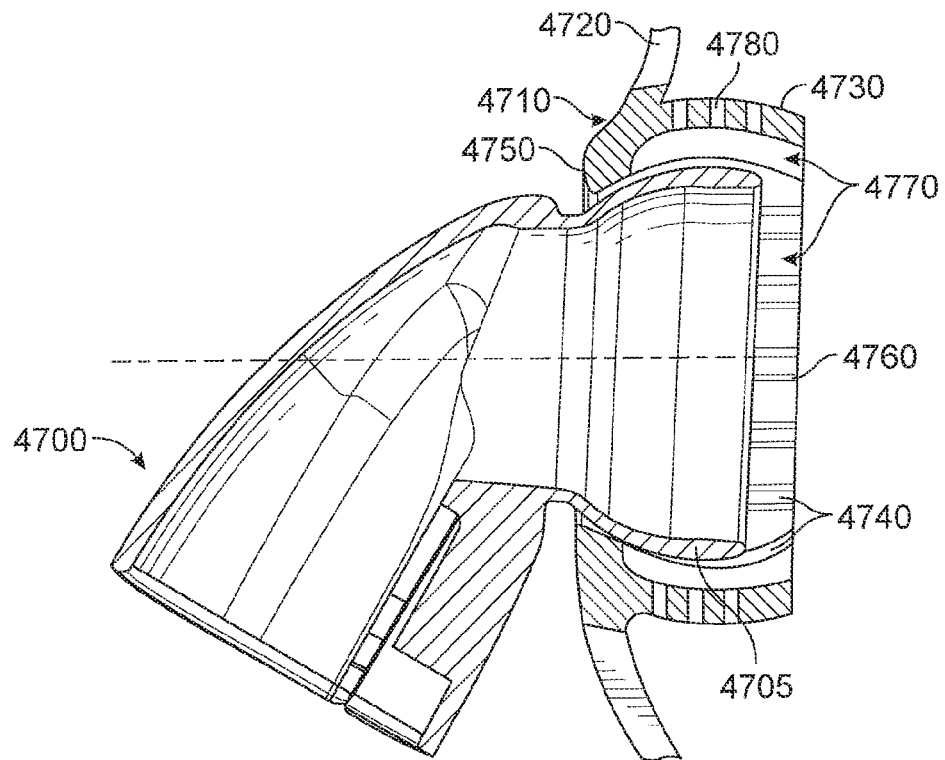
FIGS. 44A to 44E show various views of a bias-flow venting system that incorporates a ball and socket joint.
Figure 44B:
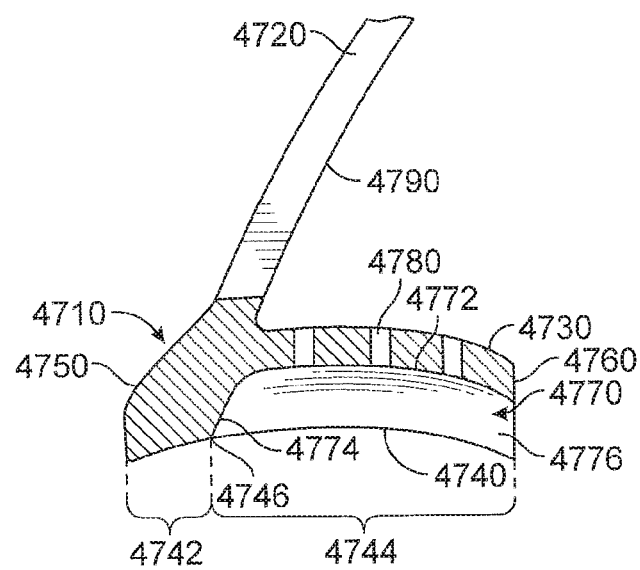

FIG. 44A shows a non-limiting exemplary embodiment, wherein a bias-flow venting system is incorporated into a respiratory mask that has an air supply connection comprising an elbow conduit 4700. The elbow 4700 includes a ball joint 4705, which is configured to connect to a corresponding socket, which can be defined by a socket insert 4710. The socket insert 4710 is configured to provide a connection between a mask frame 4720 and a seal housing (not shown). The connections between the socket insert 4710, the mask frame 4720, and the seal housing can be achieved by any connection mechanism known in the art, including, but not limited to, 'snap fit' and/or press-fit mechanical connections, welding and adhesives, or can be integral and unitary.

Figure 44C:
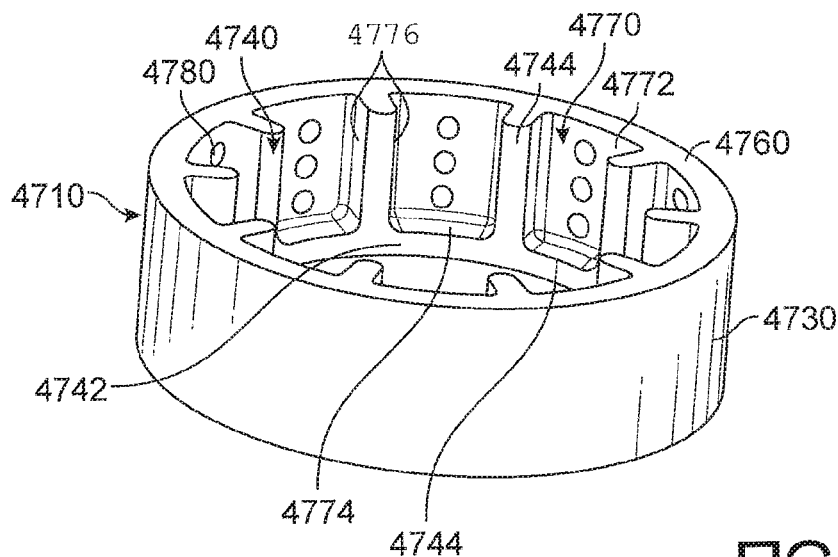

FIGS. 44B to 44E show more detailed views of the socket insert 4710. The socket insert 4710 is substantially tubular (as shown in FIG. 44C) and comprises an outer perimeter 4730, an inner perimeter 4740, and front and rear insert surfaces 4750 and 4760. The outer perimeter 4730 is configured to provide a connection between the socket insert 4710 and the mask frame 4720. The inner perimeter 4740 comprises a front bearing surface 4742 and a rear bearing surface 4744. The front and rear bearing surfaces 4742, 4744 are substantially spherical and match the geometry of the ball joint 4705. The front bearing surface 4742 comprises a continuous surface that forms a substantially airtight seal with the ball joint 4705. The rear bearing surface 4744 comprises a series of intermittent surfaces separated by recesses 4770. In other words, the intermittent surfaces are spaced a distance apart in a circumferential direction by the recesses 4770. The rear bearing surfaces 4744 connect to and extend rearwardly from the front bearing surface 4742. The substantially spherical bearing surfaces 4742, 4744 are configured to provide a retaining connection between the socket insert 4710 and the ball joint 4705, wherein translational movement of the ball from front to rear is restricted but the ball joint can rotate freely within the socket.

Figure 44D:
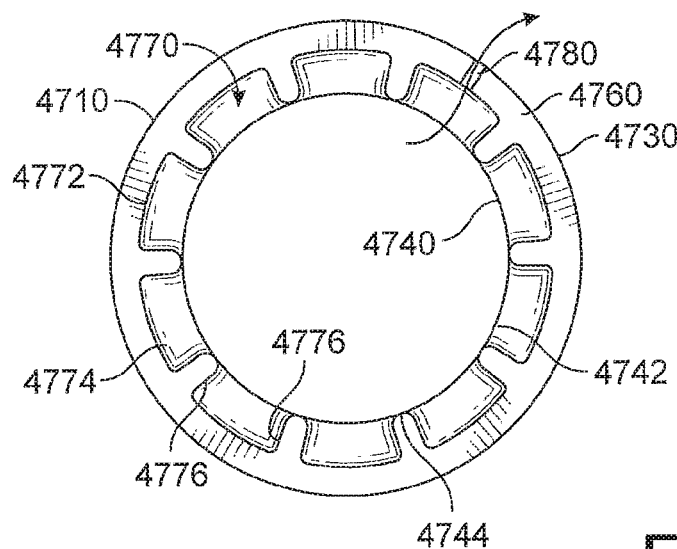
Figure 44E:
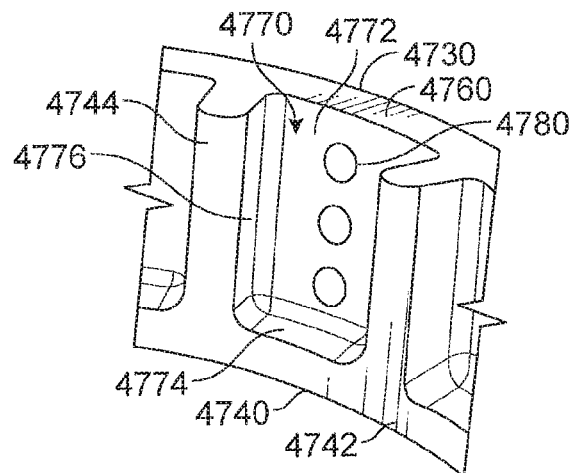

As shown in FIGS. 44C and 44D, a plurality of recesses 4770 are spaced radially around the inner perimeter 4740. The recesses 4770 have a substantially rectangular profile (as shown in FIGS. 44C and 44E) and comprise an outer recess wall 4772, a front recess wall 4774 and side walls 4776. The outer recess wall 4772 is configured to be offset between the inner perimeter 4740 and the outer perimeter 4730 and is substantially spherical. The outer recess wall 4772 is connected to the front bearing surface 4742 by the front recess wall 4774 and the rear bearing surfaces 4744 by the side walls 4776. The front recess wall 4774 extends at an obtuse angle between the rear edge 4746 of the front bearing surface 4742 and the outer recess wall 4772. The side walls 4776 extend between the rear bearing surfaces 4744 and the outer recess wall 4772 at an obtuse angle.

The recess 4770 has an open end that forms a toothed-like geometry in the rear insert surface 4760. The open end creates a path between the socket insert 4710 and the ball joint 4705 through which exhaled air can pass. Exhaust holes 4780 extend radially between the outer recess wall 4772 and the outer perimeter 4730. The exhaust holes 4780 allow exhaled air to pass through the recesses 4770 and be exhausted to atmosphere. The embodiment of the present disclosure includes three exhaust holes 4780 within each recess 4770; however, other embodiments may have more or less holes. The number of holes can be determined by the diameter of the holes and the flow rate through the holes required to flush $CO_2$ from within the mask. The exhaust holes 4780 are preferably formed via laser drilling; however, other known hole forming techniques (such as in-mold formation) may be used.

As shown in FIG. 44A, the mask frame 4720 forms a shroud 4790 in front of the exhaust holes 4780. In some embodiments, the shroud 4790, in combination with a seal housing (not shown), can form a plenum chamber and vent path, which may reduce draft generated by the exhausted air. The illustrated shroud 4790 has a substantially conical structure. There can be a gap between the mask frame 4720 and the seal housing that provides a vent path for exhausted air to pass through.

In some embodiments (not shown), the connection between the socket insert 4710 and a seal housing can be located on the outer perimeter 4730. Alternatively, the connection can be located on the rear insert surface 4760 or any other appropriate location.

In alternative embodiments, the geometry of the recesses 4770 may vary. The profile of the recesses 4770 may not be rectangular. In some embodiments, it may be triangular, asymmetric or any other suitable geometry that provides a path through which exhausted air can pass. In further embodiments, the recesses 4770 may not have defined front, outer and side walls 4772, 4774, 4776. The recesses may comprise a continuous contoured surface.

Figure 45:
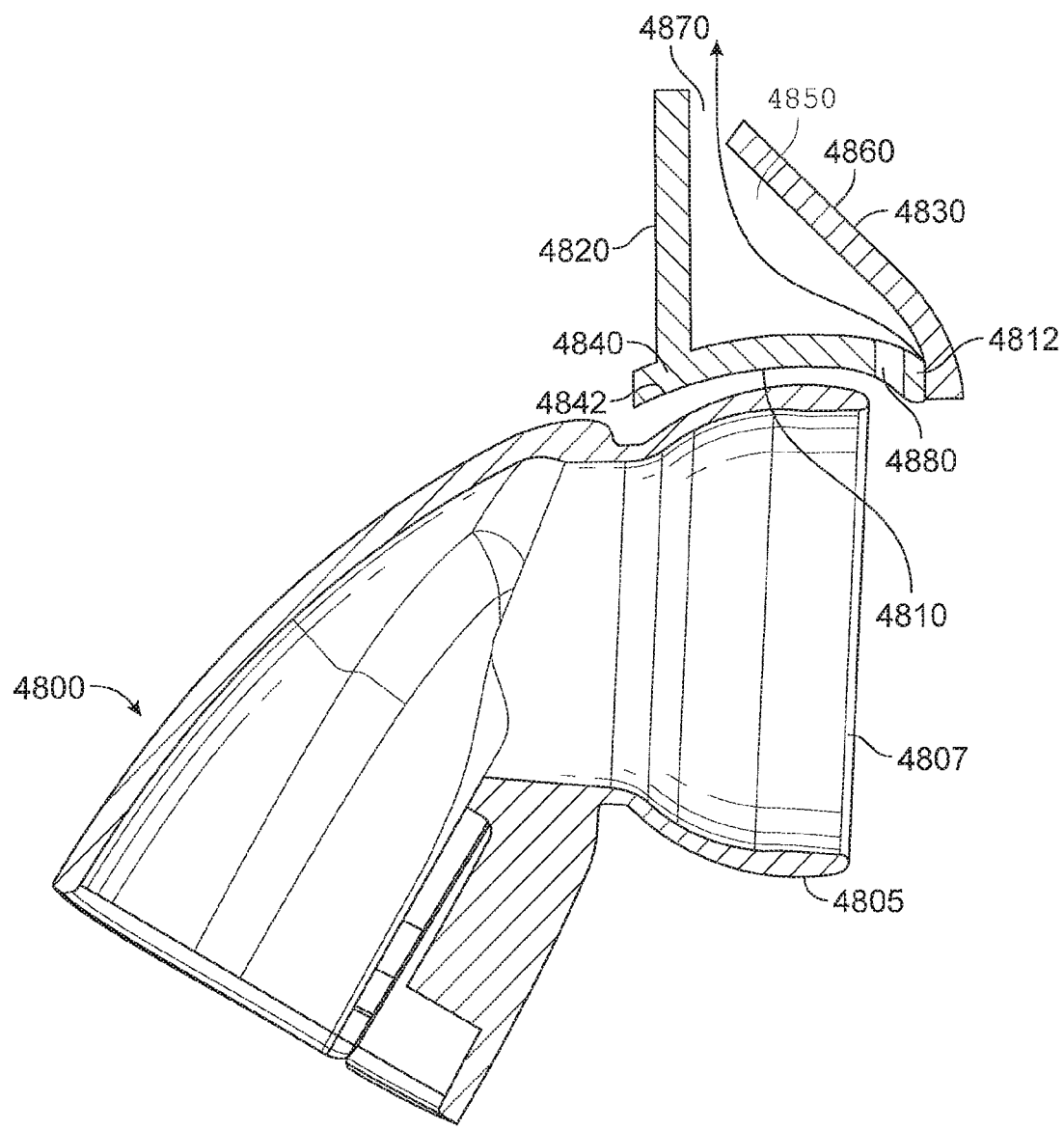
FIG. 45 shows a cross-sectional view of a further bias-flow venting system configuration.

FIGS. 45 to 48 show a range of non-limiting exemplary embodiments of different socket insert configurations. FIG. 45 shows an embodiment similar to the previously described embodiment. It comprises an elbow 4800 with a ball joint 4805, wherein the ball joint 4805 is configured to connect to a socket insert 4810. The socket insert 4810 is configured to be connected between a mask frame 4820 and a seal housing 4830. The socket insert 4810 varies from the previous embodiment in that it has an inner perimeter 4840 that forms a single bearing surface 4842 without any recesses. The bearing surface 4842 can be spherical, as in the previous embodiment. The socket insert 4810 comprises a rear lip 4812 that is configured to extend rearward of the ball joint opening 4807. The socket insert includes a series of radially spaced exhaust holes 4880 that are located within the rear lip 4812, such that the holes are substantially clear from obstruction. The distance that the rear lip 4812 extends from the ball joint opening 4807 can be defined such that when the ball joint 4805 rotates within the socket insert 4810 the exhaust holes 4880 are not completely obstructed by the ball joint.

In this embodiment, the exhausted air passes through the exhaust holes 4880 in the socket insert 4810 and into a plenum chamber 4850. The plenum chamber 4850 is formed by the mask frame 4820 and the seal housing 4830. This embodiment differs from the previous embodiment in that the seal housing 4830 is configured to provide a substantially conical shroud 4860, rather than the mask frame 4820. This may be beneficial in reducing the size of the mask frame and, therefore, the dead space within the seal chamber 4830. The exhausted air exits the plenum chamber 4850 via an at least partially annular exhaust vent 4870, which is formed by a gap between the mask frame 4820 and the seal housing 4830.

Figure 46:
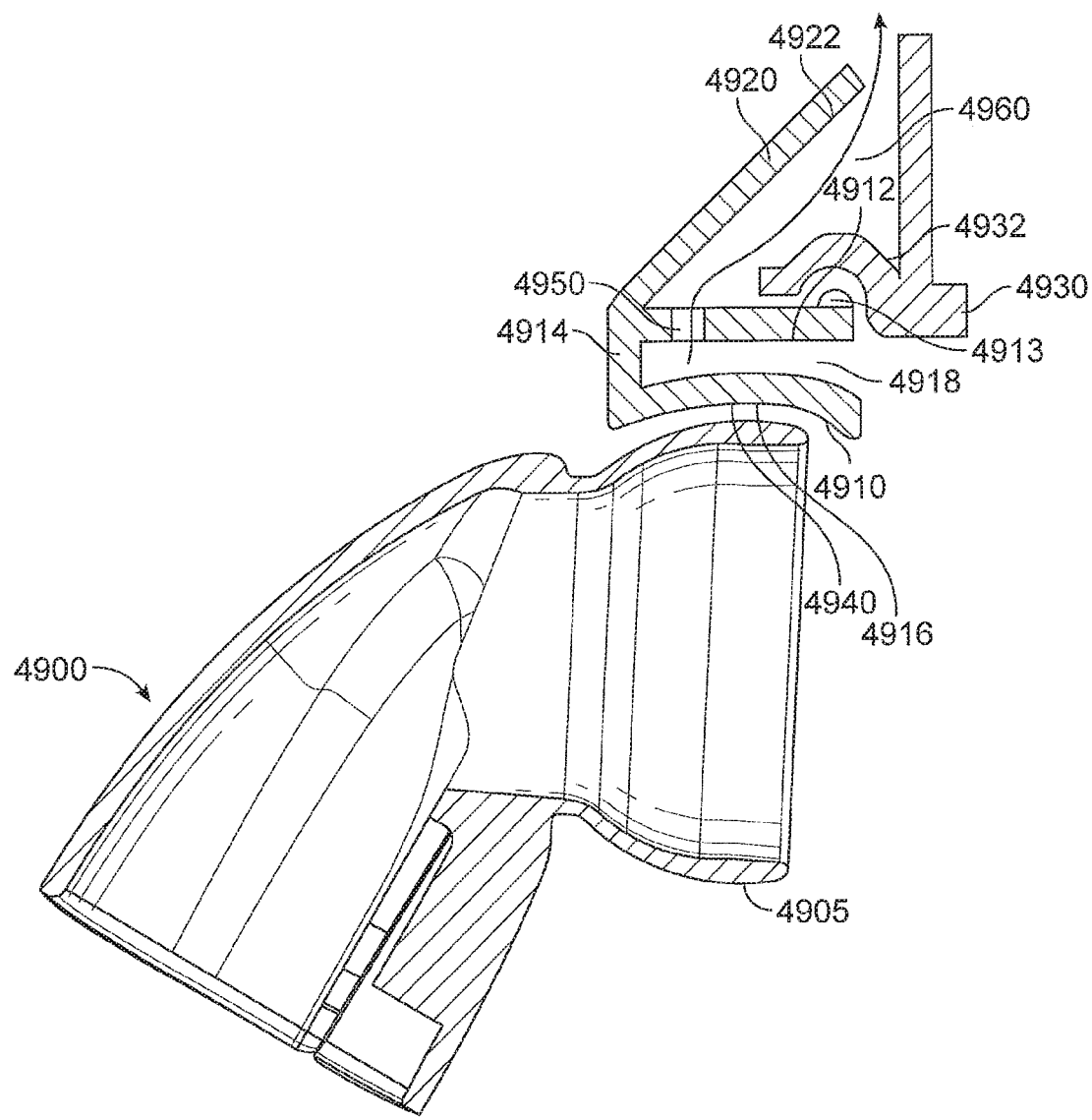
FIG. 46 shows a cross-sectional view of a further bias-flow venting system configuration.

The embodiment of FIG. 46 is similar to that of FIGS. 44A to 44E. It comprises an elbow 4900, a socket insert 4910, a mask frame 4920 and a seal housing 4930. As in the previous embodiments, the elbow comprises a ball joint 4905. The socket insert 4910 is configured to have a substantially 'c' shaped cross-sectional profile (viewed at one circumferential location) and comprises an outer perimeter wall 4912, a front wall 4914 and a bearing surface wall 4916 that form an annular channel 4918. The outer perimeter wall 4912 and the bearing surface wall 4916 are connected and offset from one another by the front wall 4914. The bearing surface wall 4916 has an inner surface and an outer surface, wherein the inner surface comprises a bearing surface 4940. The bearing surface 4940 is configured to restrict translational movement of the ball joint 4905, whilst allowing rotation.

The outer perimeter wall 4912 is configured to provide a connection between the mask frame 4920 and seal housing 4930. The mask frame 4920 is connected to the front of the outer perimeter wall 4912 and the seal housing 4930 is connected to the rear. The outer perimeter wall comprises a snap fit bump 4913 that interlocks with a snap fit connector 4932 that forms part of the seal housing 4930. In alternative embodiments, the connections between the mask frame 4920, the socket insert 4910, and the seal housing 4930 may be provided by any suitable means known in the art.

An array of exhaust holes 4950 is positioned radially within the outer perimeter wall 4912. The exhaust holes provide a path for exhausted air to flow from within the mask, through the annular channel 4918, and out to atmosphere. The number and size of the exhaust holes will be defined based on the required flow rate to flush $CO_2$ from within the mask. The exhausted air passes through the exhaust holes 4950 and into a plenum chamber 4960. The plenum chamber 4960 is formed between the mask frame 4920 and the seal housing 4930. The mask frame 4920 comprises a substantially conical shroud 4922, similar to those described in previous embodiments.

Figure 47:
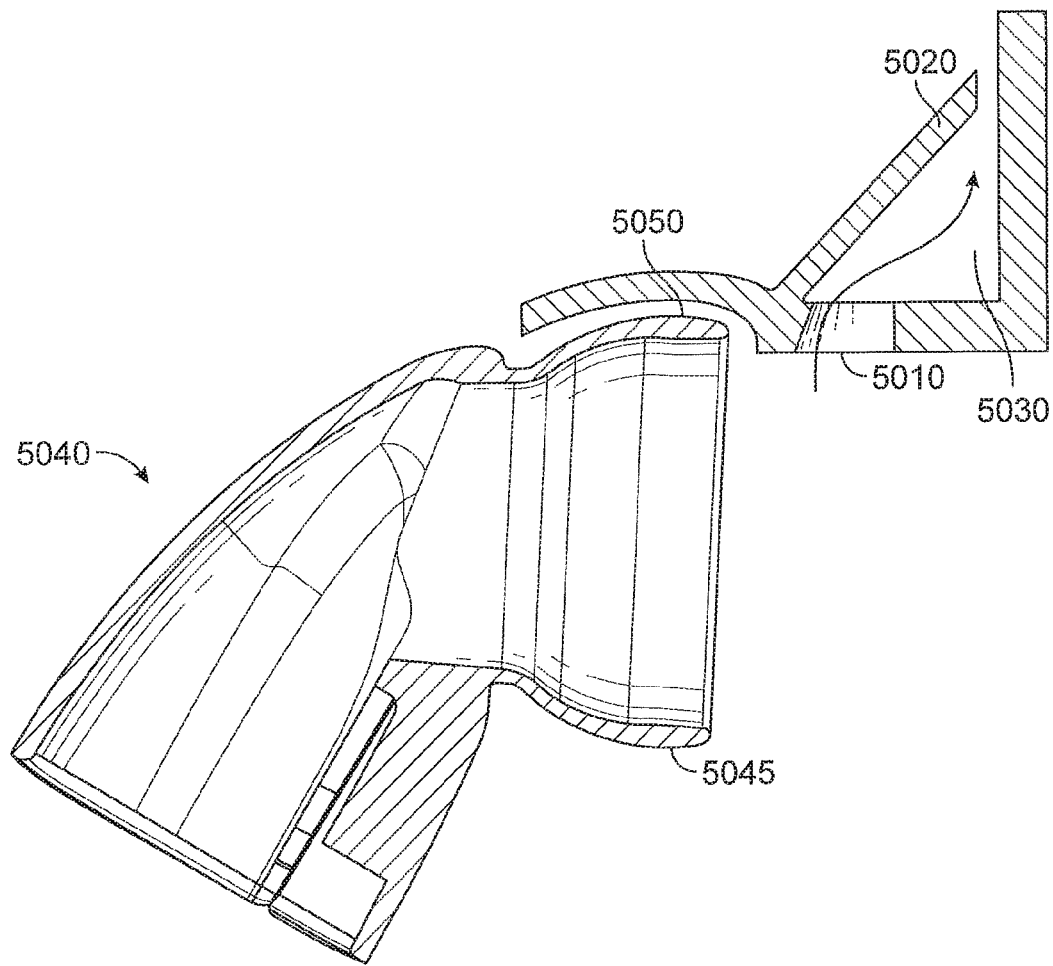
FIG. 47 shows a cross-sectional view of a further bias-flow venting system configuration.

FIG. 47 shows an embodiment where the exhaust holes 5010, the shroud 5020 and the plenum chamber 5030 are rearward of the elbow 5040 and ball joint 5045. The ball socket 5050 may form part of a mask frame or may be a separate insert component.

Figure 48:
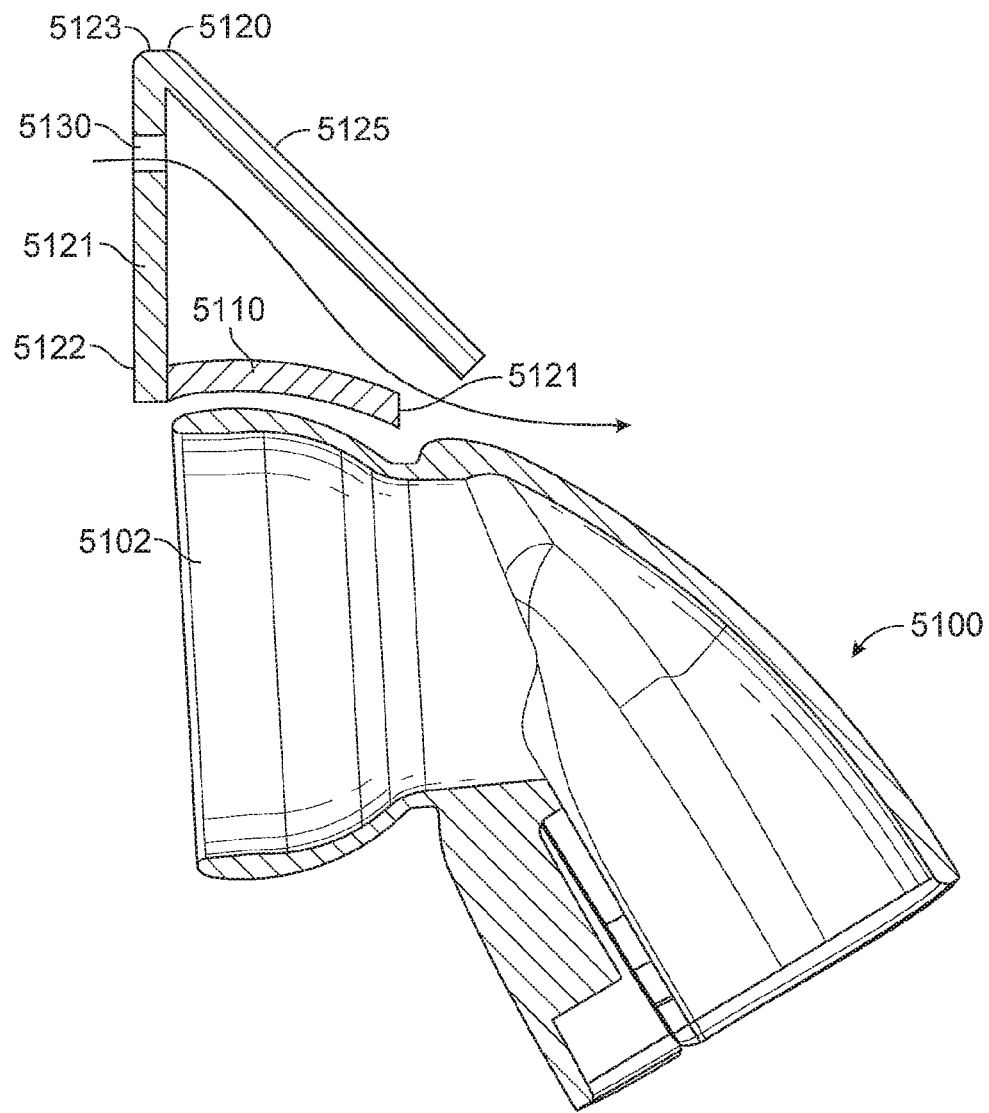
FIG. 48 shows a cross-sectional view of a further bias-flow venting system configuration.

FIG. 48 shows a further embodiment of a bias-flow venting system configuration that may be used to diffuse exhausted air towards an elbow, as opposed to away from an elbow (as in previous embodiments). The components of this embodiment are shown in isolation from other components of a respiratory mask, such as a mask frame and a seal chamber. As such, the components may be incorporated into other components of a mask in a variety of ways. Similarly, FIGS. 45-48 show only an upper portion of the socket insert, but preferably the socket insert surrounds the ball joint of the elbow. This embodiment comprises an elbow 5100 with a ball joint 5102, a socket member 5110 and a shroud member 5120. The socket member 5110 comprises a spherical wall section configured to rotatably connect to the ball joint 5102.

The socket member 5110 may be configured to form a part of a mask frame or a seal housing or, alternatively, may be a separate insert component. The shroud member 5120 comprises a seal housing wall 5121 and a shroud wall 5125. The seal housing wall 5121 is configured to form part of or connect to a seal housing (not shown). It comprises an elbow end 5122 and a distal end 5223, wherein the elbow end connects to the socket member 5110 and the distal end adjoins the shroud wall 5125. The seal housing wall 5121 also comprises an annular array of exhaust holes 5130, which are located proximal to the distal end 5123. The shroud wall 5125 comprises an annular wall section that is angled inwardly towards the elbow 5100. The shroud wall is configured to create a plenum chamber 5140 in combination with the seal housing wall 5121 and the socket member 5110. An exhaust vent 5150 is formed by a gap between the front ends of the socket member 5110 and the shroud wall 5125.

Figure 49:
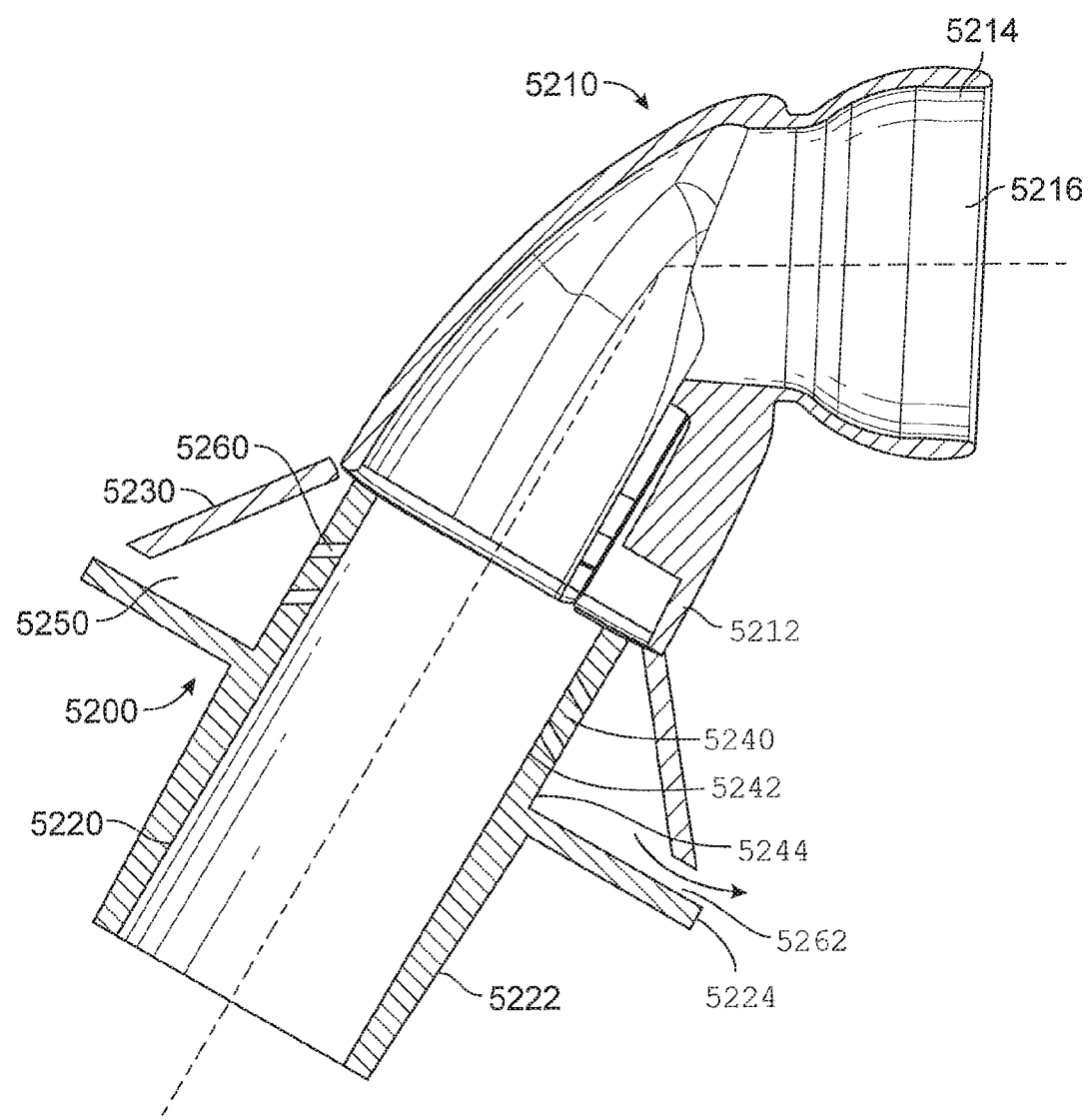
FIG. 49 shows a cross-sectional view of an embodiment where the bias-flow venting system is attached to an elbow.

FIG. 49 shows a non-limiting exemplary embodiment, wherein the bias-flow venting system 5200 is provided to one end of an elbow 5210, wherein the elbow is configured to be connected to and supply air to a respiratory mask. The bias-flow venting system comprises a conduit connector 5220, a shroud 5230 and a cylindrical exhaust member 5240. The elbow comprises an air supply end 5212 and a mask attachment end 5214. In this figure, it is shown that the mask attachment end 5214 comprises a ball joint 5216; however, in other embodiments, it may comprise an annular swivel connection or any other appropriate connection that allows for rotation between the elbow 5210 and a mask. The conduit connector 5220 comprises a cylindrical conduit 5222 and a flange 5224. The cylindrical conduit 5222 is configured to provide a removable connection with an air supply conduit. The flange 5224 extends perpendicularly from the end of the cylindrical conduit 5222 that is proximal to the air supply end 5316 of the elbow 5210. It is configured to form a wall of a plenum chamber 5250. In alternative embodiments, the flange 5224 may be formed at a greater or lesser angle to the cylindrical conduit 5222.

The shroud 5230 and the cylindrical exhaust member 5240 form the remaining walls of the plenum chamber 5250. The cylindrical exhaust member 5240 is configured to provide a connection between the conduit connector 5220 and the air supply end 5212 of the elbow 5210. The connections may be permanent or temporary. The cylindrical exhaust member 5240 comprises internal and external wall surfaces 5242, 5244, and an array of radial exhaust holes 5260 that extend therebetween. The exhaust holes 5260 are angled such that air flow through them is directed away from the elbow; however, in some embodiments the holes may be perpendicular to the cylindrical exhaust member or angled towards the elbow. The shroud 5330 is configured to connect to the air supply end 5212 of the elbow 5210 but, in alternative embodiments, may be connected to the cylindrical exhaust member 5240. The shroud 5230 comprises a substantially conical geometry that is configured to cover the exhaust holes 5260 in manners similar to those described in the previous embodiments. An exhaust vent 5262 is formed by an annular gap between the shroud 5230 and the flange 5224. The exhaust vent 5262 provides a path for exhausted air to exit the plenum chamber 5250.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A cushion module for a respiratory interface, comprising:
    a seal housing constructed from a relatively rigid material, the seal housing defining an aperture configured to allow a breathing gas to enter an interior of the cushion module;
    a seal supported by the seal housing and having an upper portion and a lower portion, the seal further comprising a face contacting surface configured to contact the face of a user and create at least a substantial seal with the face of the user, the face contacting surface having an inner edge defining an opening in the face contacting surface, wherein the upper portion of the seal comprises a reduced stiffness portion defined between a first boundary and a second boundary such that the reduced stiffness portion deforms in response to forward movement of an upper portion of the face contacting surface, wherein an angle defined between the first boundary and the second boundary is at least 20 degrees;
    wherein the reduced stiffness portion comprising a rolling portion configured to roll over onto an outer surface of the cushion module in response to the forward movement of the upper portion of the face contacting surface.

2. The cushion module of claim 1, wherein the angle between the first boundary and the second boundary is at least about 25 degrees.

3. The cushion module of claim 1, wherein the angle between the first boundary and the second boundary is between about 27 degrees and about 34 degrees.

4. The cushion module of claim 1, wherein the angle between the first boundary and the second boundary is one of about 27 degrees, about 29 degrees and about 34 degrees.

5. The cushion module of claim 1, wherein a portion of the seal defining the face contacting surface comprises a pair of nose pads positioned on each side of the opening in the upper portion of the seal, wherein an entirety of each of the nose pads is spaced outwardly from the opening.

6. The cushion module of claim 5, wherein the nose pads are the thickest portions of the portion of the seal defining the face contacting surface.

7. The cushion module of claim 6, further comprising a pair of thickened outer peripheral portions defined by the portion of the seal defining the face contacting surface, wherein at least a portion of the thickened outer peripheral portions are positioned below the nose pads.

8. The cushion module of claim 7, wherein at least a portion of the thickened outer peripheral portions are positioned above the nose pads.

9. The cushion module of claim 1, wherein a continuous portion of the inner edge of the opening defines a thickness of equal to or less than 0.6 mm, wherein the continuous portion of the inner edge extends inwardly from the inner edge at least 1 mm and extends along at least an entirety of the upper portion of the seal.

10. The cushion module of claim 9, wherein a section of the continuous portion of the inner edge located within 0.5 mm of the inner edge is equal to or less than 0.4 mm in thickness.

11. The cushion module of claim 1, wherein the upper portion of the seal defines a nose bridge portion that contacts a bridge of the user's nose, wherein the nose bridge portion of the opening defines a continuously curved portion of the inner edge.

12. The cushion module of claim 11, wherein a width of the nose bridge portion is equal to or less than about 11 mm.

13. The cushion module of claim 11, wherein a vertical dimension of a vertical center of the nose bridge portion is equal to or greater than about 15 mm.

14. The cushion module of claim 11, wherein a depth between a rearmost point of the nose bridge portion and a lower edge of the nose bridge portion on the vertical center of the seal is at least about 4 mm.

15. The cushion module of claim 1, wherein the reduced stiffness portion comprises a front wall having a height of at least about 7 mm.

16. The cushion module of claim 15, wherein the height of the front wall is between about 7.3 mm and about 7.7 mm.

17. The cushion module of claim 15, wherein a thickness of the front wall and a top wall progressively increases from a lower end of the front wall to a rearward end of the top wall.

18. The cushion module of claim 1, wherein a distance between a point on a centerline of the upper portion and a point on a centerline of the lower portion of the face contacting surface of the seal varies by more than 2 mm between a neutral position and a depressed position of the reduced stiffness region.

19. The cushion module of claim 18, wherein the distance between the point on the centerline of the upper portion and the point on the centerline of the lower portion of the face contacting surface of the seal varies by at least about 5 mm, at least about 6 mm, at least about 8 mm, at least about 10 mm or at least about 12 mm between the neutral position and the depressed position of the reduced stiffness region.

20. The cushion module of claim 18, wherein the distance varies between about 90 mm to about 84 mm between the neutral position and the depressed position of the reduced stiffness region.

21. The cushion module of claim 18, wherein the distance varies by at least about 5 percent between the neutral position and the depressed position of the reduced stiffness region.

22. The cushion module of claim 21, wherein the distance varies by at least about 6 and ⅔ percent between the neutral position and the depressed position of the reduced stiffness region.

23. A set of cushion modules comprising a plurality of the cushion modules of claim 1 in at least two different sizes, wherein the angle is different between the sizes.

24. The set of cushion modules of claim 23, comprising a small, medium and large size, wherein the angle of the small size is greater than the angles of one or both of the medium and large sizes.

25. The set of cushion modules of claim 24, wherein the angle of the large size is less than the angles of one or both of the small and medium sizes.

26. The set of cushion modules of claim 25, wherein the angle of the small size is about 34 degrees, the angle of the medium size is about 29 degrees and the angle of the large size is about 27 degrees.

27. The set of cushion modules of claim 25, wherein the angles of the small, medium and large sizes are selected such that a maximum available forward displacement of the upper portion of each of the small, medium and large sizes is the same.

28. The set of cushion modules of claim 24, wherein the angle of the small size is selected such that a maximum available forward displacement of the upper portion of the small size is at least equal to a maximum available forward displacement of the upper portion of one or both of the medium and large sizes.

29. The cushion module of claim 1, wherein a portion of the seal supported by the seal housing overlaps with the seal housing, wherein the overlap is greater at a location nearer a hinge axis of the rolling portion than at a location further from the hinge axis.

* * * * *